United States Patent [19]

Brown et al.

[11] Patent Number: 5,316,667
[45] Date of Patent: May 31, 1994

[54] TIME BASED INTERFACE DETECTION SYSTEMS FOR BLOOD PROCESSING APPARATUS

[75] Inventors: Richard L. Brown, Northbrook; John T. Foley, Wheeling, both of Ill.

[73] Assignee: Baxter International Inc., Deerfield, Ill.

[21] Appl. No.: 109,008

[22] Filed: Aug. 19, 1993

Related U.S. Application Data

[63] Continuation of Ser. No. 965,081, Oct. 22, 1992, abandoned, which is a continuation-in-part of Ser. No. 814,403, Dec. 23, 1991, abandoned, which is a continuation-in-part of Ser. No. 748,244, Aug. 21, 1991, which is a continuation of Ser. No. 514,995, May 26, 1989, Pat. No. 5,104,526, which is a continuation of Ser. No. 9,179, Jan. 30, 1989, Pat. No. 4,834,890.

[51] Int. Cl.$^5$ ............................................. B01D 21/26
[52] U.S. Cl. ........................................ 210/85; 210/94; 210/103; 210/360.1; 210/380.1; 494/10
[58] Field of Search ................ 210/85, 94, 103, 360.1, 210/380.1, 782; 494/3, 10; 604/6; 250/227.14, 231.16; 356/23, 24, 395

[56] References Cited

U.S. PATENT DOCUMENTS

| | | |
|---|---|---|
| Re.29,738 | 8/1978 | Adams .......................... 359/503 |
| 3,244,363 | 4/1966 | Hein . |
| 3,778,171 | 12/1973 | Chervenka ................... 356/246 |
| 3,858,796 | 1/1975 | Unger et al. ................... 494/34 |
| 3,955,755 | 5/1976 | Breillatt, Jr. et al. ............ 494/10 |
| 3,987,961 | 10/1976 | Sinn et al. ..................... 494/45 |
| 4,007,871 | 2/1977 | Jones et al. .................... 494/45 |
| 4,094,461 | 6/1978 | Kellogg et al. ................. 494/81 |
| 4,113,173 | 9/1978 | Lolachi ......................... 494/18 |
| 4,114,802 | 9/1978 | Brown .......................... 494/18 |
| 4,142,670 | 3/1979 | Ishimaru et al. ................ 494/38 |
| 4,146,172 | 3/1979 | Cullis et al. ................... 494/17 |
| 4,164,318 | 8/1979 | Boggs .......................... 494/18 |
| 4,230,263 | 10/1980 | Westberg ...................... 494/45 |
| 4,244,513 | 1/1981 | Fayer et al. ................... 494/10 |
| 4,261,507 | 4/1981 | Baumler ....................... 494/45 |
| 4,266,717 | 5/1981 | Jennings et al. ............... 494/45 |
| 4,278,202 | 7/1981 | Westberg ...................... 494/45 |
| 4,283,004 | 8/1981 | Lamadrid ...................... 494/18 |
| 4,344,560 | 8/1982 | Iriguchi et al. ................ 210/96.1 |
| 4,350,283 | 9/1982 | Leonian ........................ 422/72 |
| 4,386,730 | 6/1983 | Mulzet ......................... 494/81 |
| 4,387,848 | 6/1983 | Kellogg et al. ................. 494/81 |
| 4,402,680 | 9/1983 | Schoendorfer ................. 494/3 |
| 4,409,820 | 10/1983 | Nash ........................... 494/10 |
| 4,421,503 | 12/1983 | Latham, Jr. et al. ............ 494/17 |
| 4,430,072 | 2/1984 | Kellogg et al. ................. 494/45 |
| 4,447,221 | 5/1984 | Mulzet ......................... 494/45 |
| 4,482,342 | 11/1984 | Lueptow et al. ................ 494/21 |
| 4,493,691 | 1/1985 | Calari .......................... 494/10 |
| 4,525,155 | 6/1985 | Nilsson ........................ 494/3 |
| 4,530,691 | 7/1985 | Brown .......................... 494/45 |
| 4,531,932 | 7/1985 | Luppi et al. ................... 604/6 |

(List continued on next page.)

OTHER PUBLICATIONS

"The Physics of Continuous Flow Centrifugal Cell Separation", Artificial Organs, Richard I. Brown, 13(1):4-20, Raven Press 1989.

*Primary Examiner*—Robert A. Dawson
*Assistant Examiner*—Sun Uk Kim
*Attorney, Agent, or Firm*—Bradford R. L. Price; Paul C. Flattery; Daniel D. Ryan

[57] ABSTRACT

A system for monitoring the interface region between cellular constituents and plasma in a blood separation chamber employs a sensor mechanism for emitting upon the interface region energy that is absorbed by the cellular constituents. The sensor mechanism also detects the intensity of the energy that is not absorbed by the interface region to generate an unabsorbed intensity output signal. The system moves the interface region relative to the sensor mechanism during a prescribed time period. A first circuit measures variations in the unabsorbed intensity output signal over the prescribed time period and generates a time based output. A second circuit can derive the physical size of the interface region based upon the time based output.

30 Claims, 33 Drawing Sheets

U.S. PATENT DOCUMENTS

| | | | |
|---|---|---|---|
| 4,557,719 | 12/1985 | Neumann et al. | 494/37 |
| 4,604,086 | 8/1986 | Benko et al. | 494/16 |
| 4,636,193 | 1/1987 | Cullis | 494/45 |
| 4,670,002 | 6/1987 | Koreeda et al. | 494/10 |
| 4,710,161 | 12/1987 | Takabayashi et al. | 494/84 |
| 4,724,317 | 2/1988 | Brown et al. | 494/10 |
| 4,734,089 | 3/1988 | Cullis | 494/27 |
| 4,820,256 | 4/1989 | Nordstrom | 494/3 |
| 4,828,716 | 5/1989 | McEwen et al. | 210/104 |
| 4,834,890 | 5/1989 | Brown et al. | 210/94 |
| 4,846,780 | 6/1989 | Galloway et al. | 494/3 |
| 4,934,995 | 6/1990 | Cullis | 494/45 |
| 4,936,820 | 6/1990 | Dennehey et al. | 494/1 |
| 5,006,103 | 4/1991 | Bacehowski et al. | 494/45 |
| 5,067,938 | 11/1991 | Uchida et al. | 494/12 |
| 5,076,911 | 12/1991 | Brown et al. | 210/94 |
| 5,104,526 | 4/1992 | Brown et al. | 210/94 |
| 5,194,145 | 3/1993 | Schoendorfer | 210/90 |

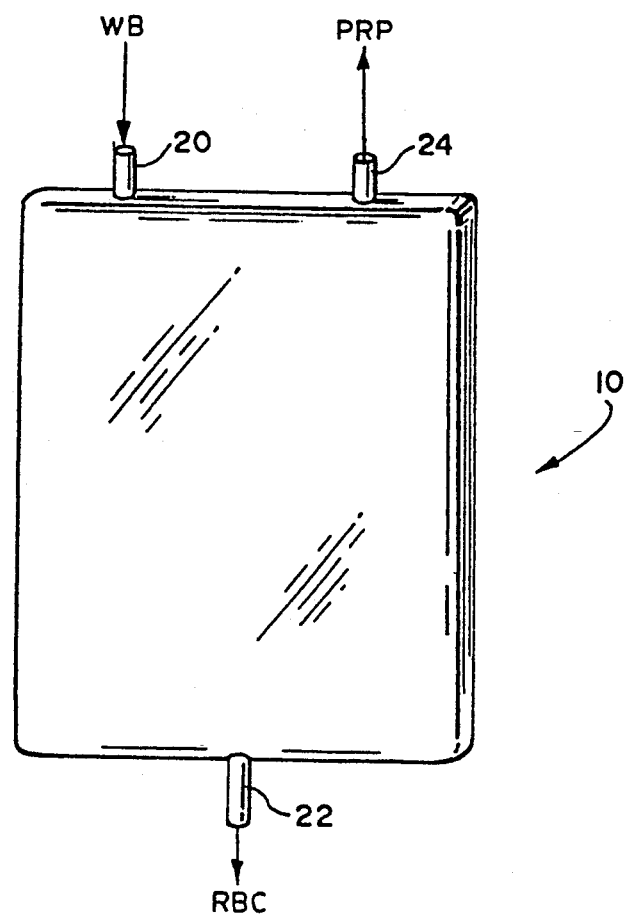
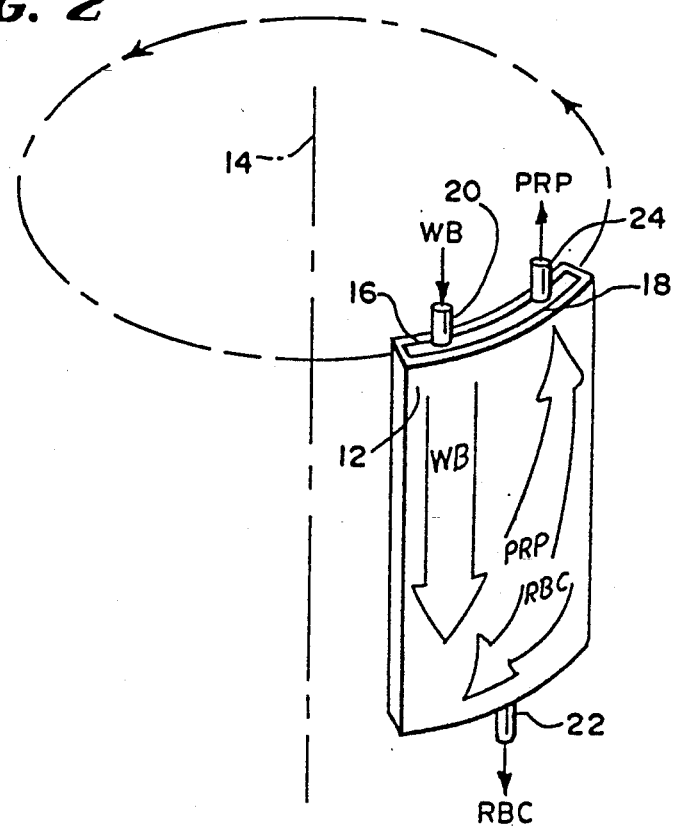

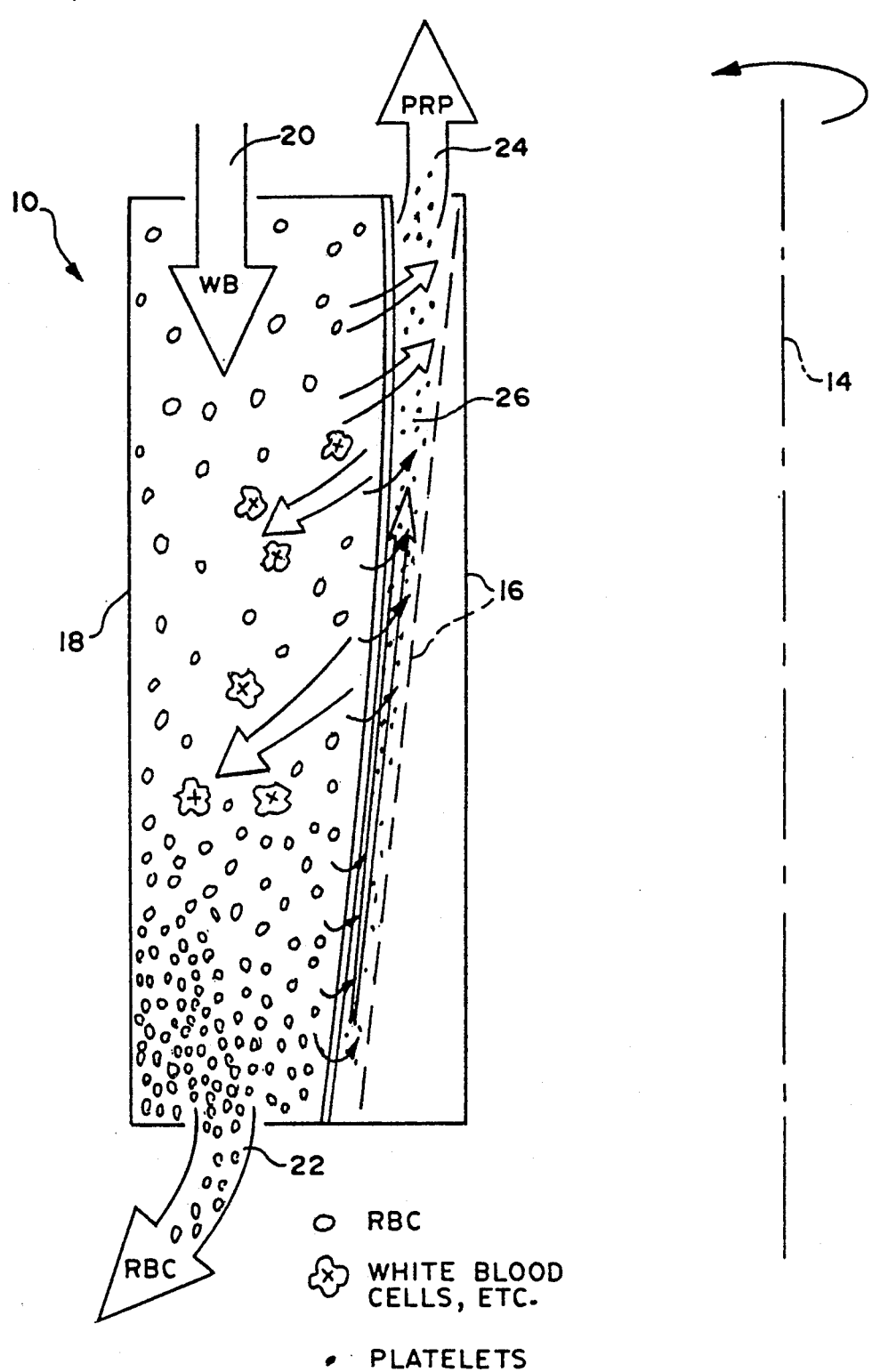

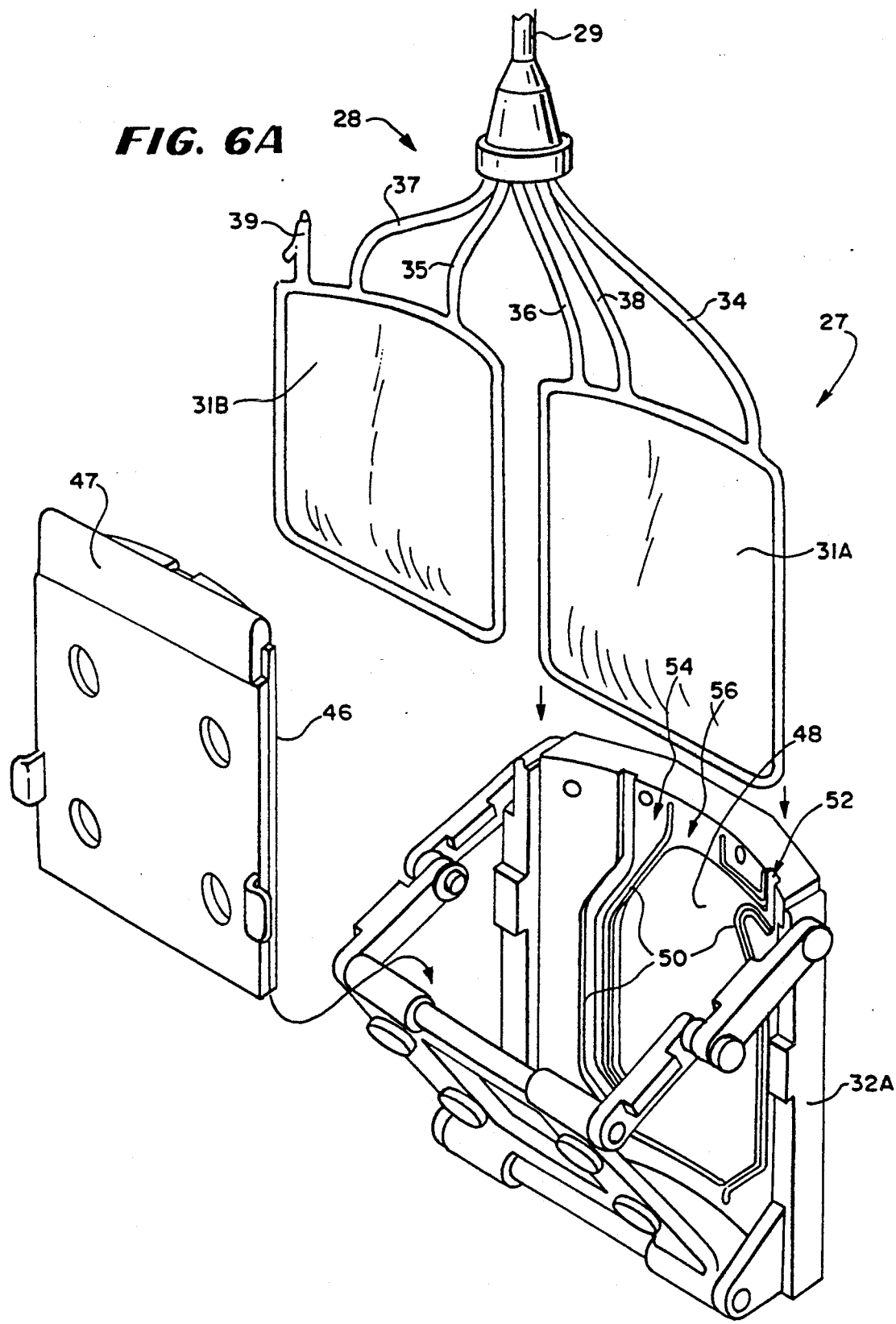

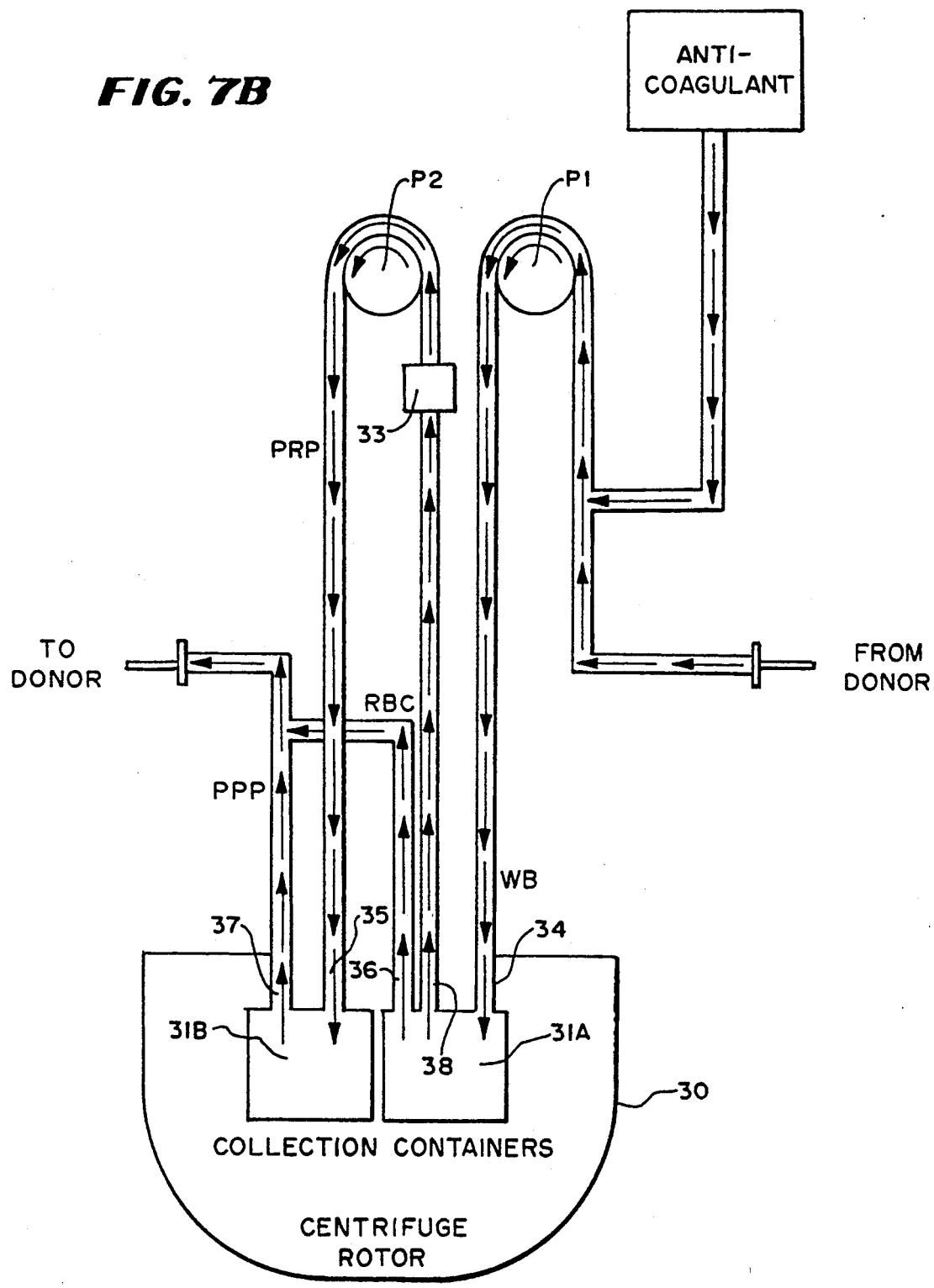

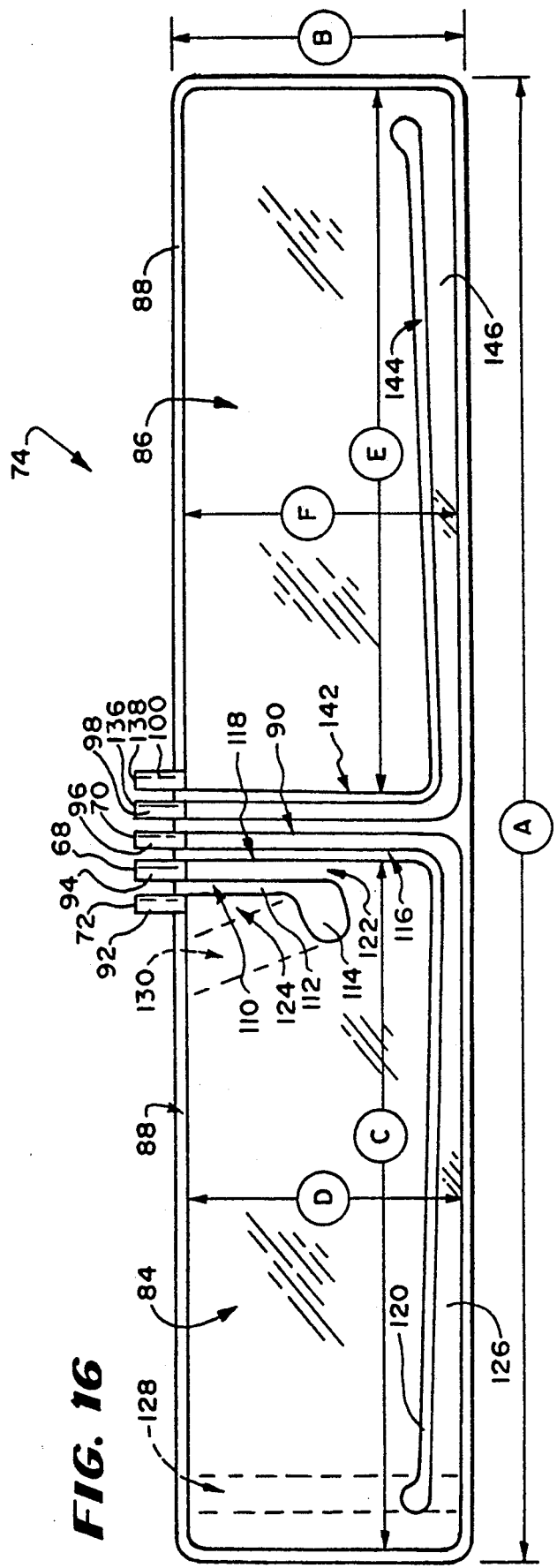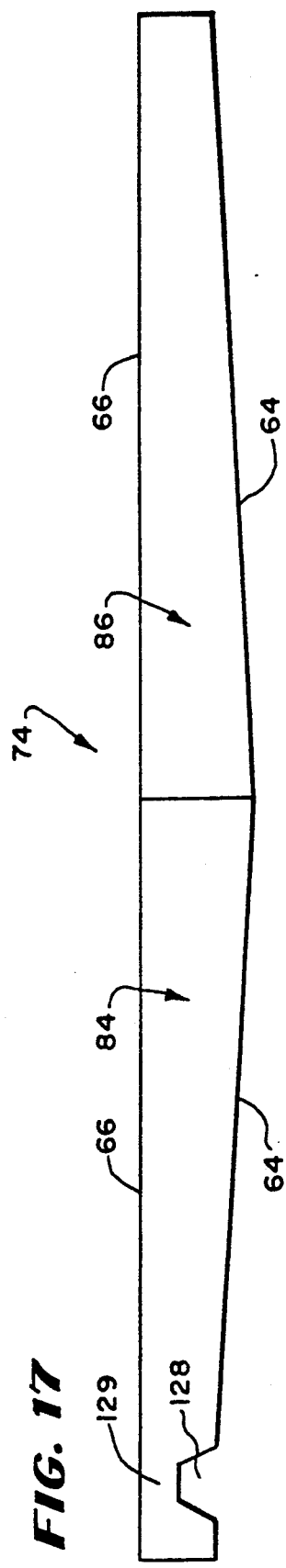

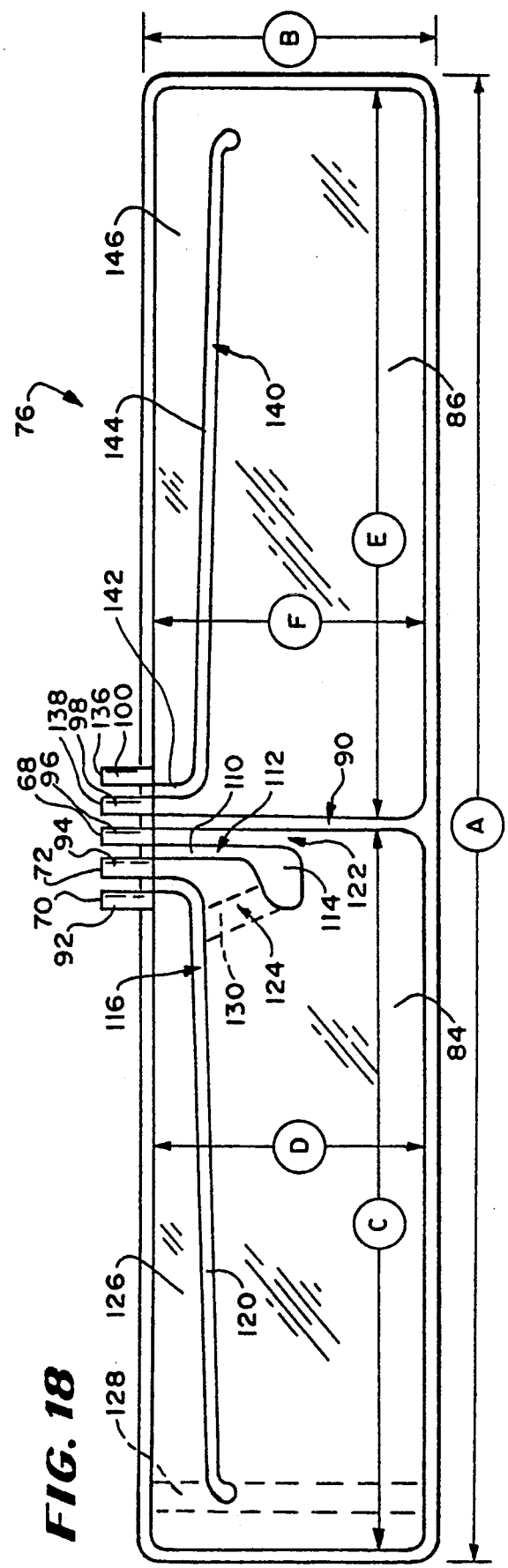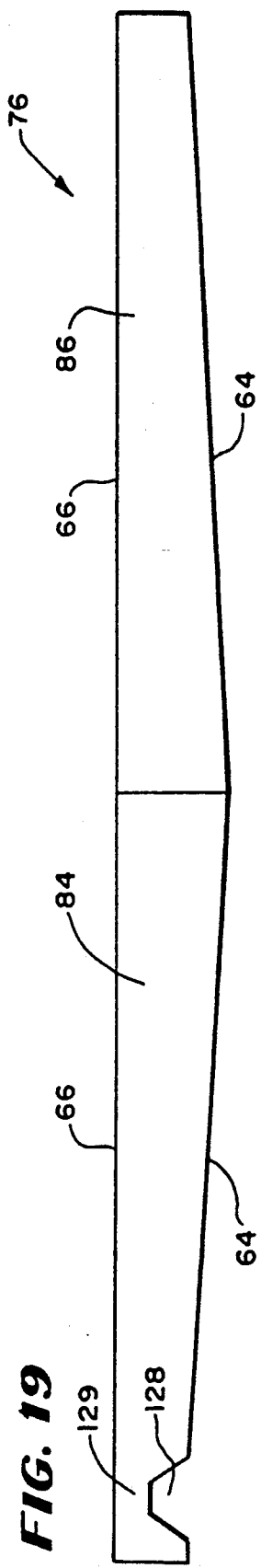

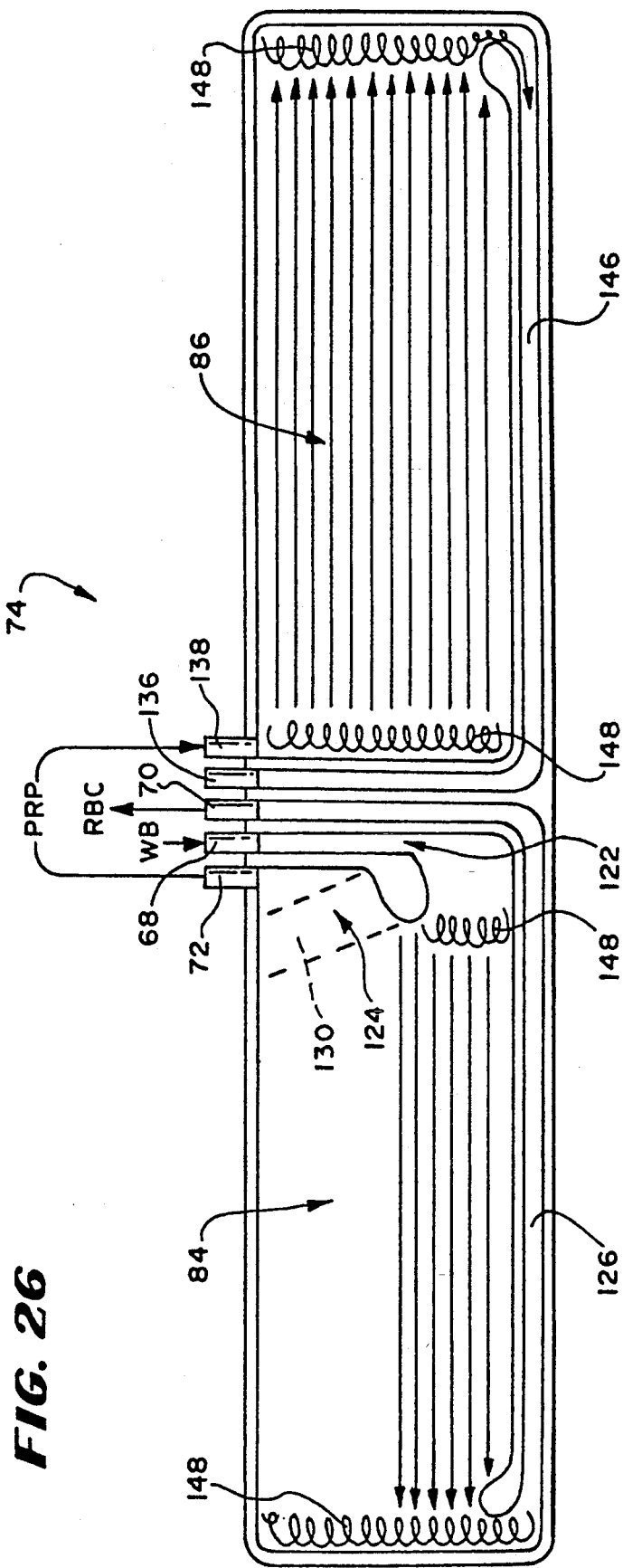

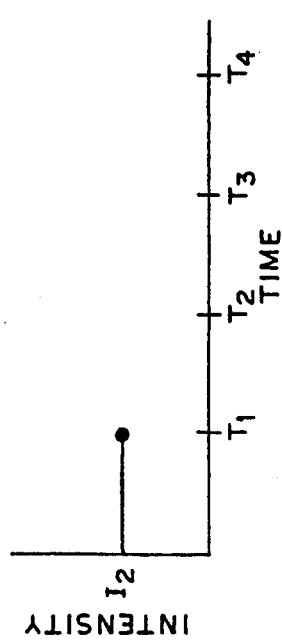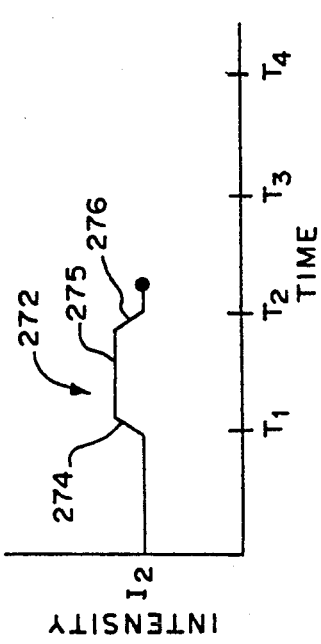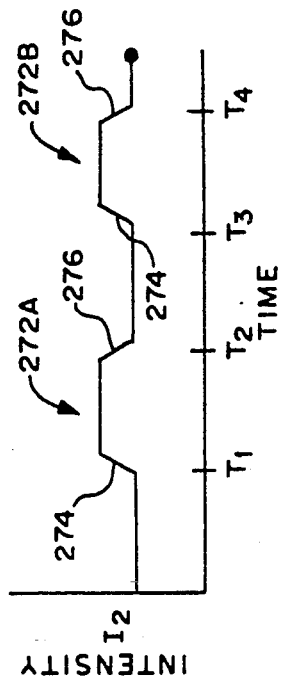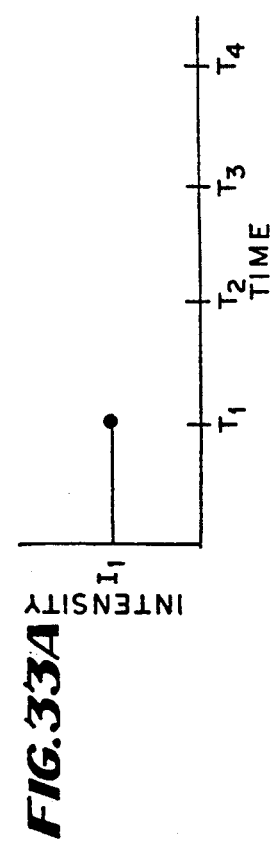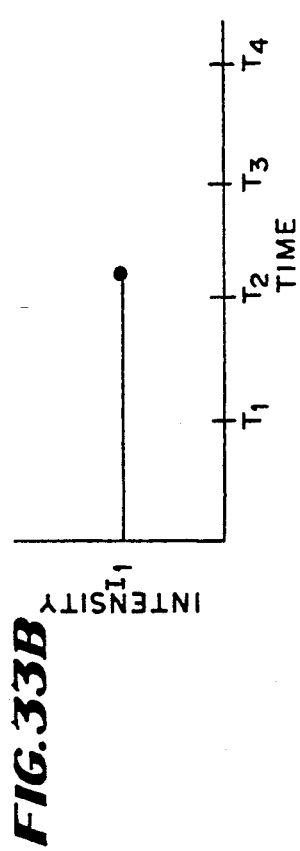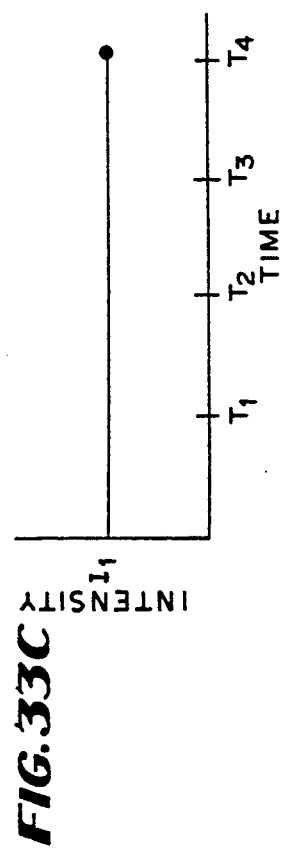
FIG.33A  FIG.33B  FIG.33C

TIME BASED INTERFACE DETECTION SYSTEMS FOR BLOOD PROCESSING APPARATUS

This is a continuation of copending application Ser. No. 07/965,081 filed on Oct. 22, 1992, now abandoned, which is a continuation-in-part of U.S. application Ser. No. 07/814,403 filed Dec. 23, 1991, now abandoned, which is a continuation-in-part of U.S. application Ser. No. 07/748,244 filed Aug. 21, 1991, which is a continuation of U.S. application Ser. No. 07/514,995 filed May 26, 1989, now U.S. Pat. No. 5,104,526, which is a continuation of U.S. application Ser. No. 07/009,179 filed Jan. 30, 1987 (now U.S. Pat. No. 4,834,890).

FIELD OF THE INVENTION

The invention relates to centrifugal processing systems and apparatus.

BACKGROUND OF THE INVENTION

Today blood collection organizations routinely separate whole blood by centrifugation into its various therapeutic components, such as red blood cells, platelets, and plasma.

Conventional blood processing systems and methods use durable centrifuge equipment in association with single use, sterile processing chambers, typically made of plastic. The centrifuge equipment introduces whole blood into these chambers while rotating them to create a centrifugal field.

Whole blood separates within the rotating chamber under the influence of the centrifugal field into higher density red blood cells and platelet-rich plasma. An intermediate layer of white blood cells and lymphocytes forms an interface between the red blood cells and platelet-rich plasma.

In conventional blood separation systems and methods, it is important to monitor the position of the interface during processing, to keep the formed elements in the interface and red blood cells adjacent to the interface from entering the platelet-rich plasma stream.

SUMMARY OF THE INVENTION

The invention provides improved interface detection systems for blood processing apparatus. The interface detection systems measure the size of the interface region based upon time based signals.

One aspect of the invention provides a system for monitoring the interface region between cellular constituents and plasma in a blood separation chamber. The system includes a sensor mechanism for emitting upon the interface region energy that is absorbed by the cellular constituents. The sensor mechanism also detects the intensity of the energy that is not absorbed by the interface region to generate an unabsorbed intensity output signal. The system moves the interface region relative to the sensor mechanism during a prescribed time period. A first circuit measures variations in the unabsorbed intensity output signal over the prescribed time period and generates a time based output.

In a preferred embodiment, a second circuit derives the physical size of the interface region based upon the time based output.

In a preferred embodiment, the sensor mechanism includes a first emitter for emitting upon the interface region energy that is absorbed by cellular constituent portion of the interface. The sensor mechanism also includes a first detector for detecting the intensity of the energy emitted by the first emitter that is not absorbed by the interface region and for generating an unabsorbed intensity output signal.

In this arrangement, the first circuit is coupled to the first detector for generating a correction signal to alter the intensity of the energy emitted by the first emitter to keep the unabsorbed intensity output signal constant. Also in this arrangement, the first circuit registers the first emitter intensities as altered in response to the correction signal over the prescribed time period and generates the time based output of these altered intensities.

In a preferred embodiment, the first circuit converts the intensities to square wave time pulses. In this preferred embodiment, the second circuit derives the physical dimension of the cellular constituent portion of the interface region ($D_I$) as follows:

$$D_I = \frac{P_L \times D_B}{P_P}$$

where:
- $P_L$ is the measured length of the time pulse (in seconds);
- $P_P$ is the measured period of the time pulse (also in seconds);
- $D_I$ is the length of the cellular constituent portion of the interface (in inches) to be derived; and
- $D_B$ is the circumference of the blood separation chamber (in inches).

In a preferred embodiment, the system also includes a third circuit that compares the derived physical measurement of the interface $D_I$ with a control value to generate an error signal to alter the position of the cellular constituent portion of the interface region.

Another aspect of the invention provides a centrifuge having a stationary frame that supports first and second elements for relative rotation. One of the rotating elements includes a blood processing chamber. The other rotating element carries the sensor mechanism to monitor the location of the interface in the mutually rotating processing chamber. At least one component of one of the first and second circuits is carried on the stationary frame.

According to this aspect of the invention, the interface monitoring system includes a first data link on the rotating element that carries the sensor means. The first data link emits energy to the one component on the stationary frame without mechanical contact with the stationary frame. The first data link including a circuit that modulates the emitted energy according to variations in the unabsorbed intensity output signal.

In this arrangement, the interface monitoring system also includes a second data link on the stationary frame. The second data link receives the modulated energy emitted by the first data link. The second data link including a circuit that demodulates the detected energy to generate a second output signal that also varies according to the variations in the unabsorbed intensity output signal.

In a preferred embodiment, the modulated energy is transmitted in the form of light through an enclosed passage within the drive shaft that rotates the processing chamber element.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

BRIEF DESCRIPTION OF THE DRAWINGS

FIG. 1 is a diagrammatic view of an enhanced yield axial flow processing chamber that embodies the features of the invention;

FIG. 2 is a diagrammatic view of the chamber shown in FIG. 1 operating in a centrifugation field;

FIG. 3 is a diagrammatic view of the interior of the chamber shown in FIG. 1 when processing whole blood within the centrifugation field;

FIGS. 6A and 6B are a perspective views of a blood processing assembly that incorporates enhanced yield first and second stage axial flow processing chambers, each with an associated centrifuge holder shown in an opened position, with FIG. 6A showing the first stage holder and 6B showing the second stage holder;

FIG. 7B is a schematic view of the flow system associated with the blood processing assembly when being used to separate blood components;

FIG. 16 is a plan view of a blood processing assembly that incorporates an enhanced yield circumferential flow processing chamber that embodies the features of the invention;

FIG. 17 is a view of the interior of the blood processing assembly shown in FIG. 16, taken between the low-G and high-G walls radially along the centrifugation field;

FIG. 18 is a plan view of an alternative blood processing assembly that incorporates an enhanced yield circumferential flow processing chamber that embodies the features of the invention;

FIG. 19 is a view of the interior of the blood processing assembly shown in FIG. 18, taken between the low-G and high-G walls radially along the centrifugation field;

FIG. 26 is a view of the vortex conditions generated within the blood processing assembly shown in FIGS. 16/17 during use;

FIGS. 33A/B/C are a series of diagrammatic views showing the operation of the interface control system shown in FIG. 30 during rotation of the centrifuge assembly;

DESCRIPTION OF THE PREFERRED EMBODIMENTS

I. Enhanced Yield Axial Flow Systems

Figure 3A:
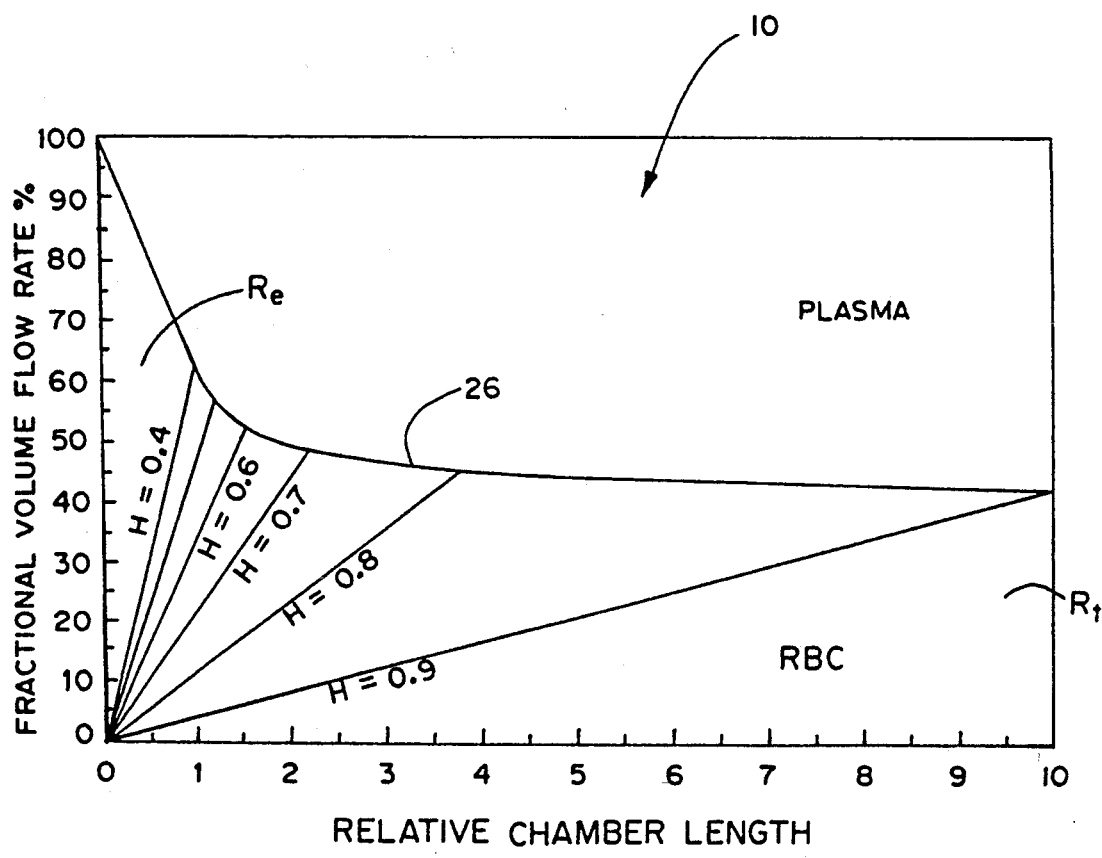
FIG. 3A is a graph showing the distribution of increasing regions of surface hematocrit along the interface formed in a blood separation chamber.

A. Single Stage Whole Blood Separation Systems

FIGS. 1 to 3 show, in diagrammatic fashion, a single stage axial flow centrifugal blood processing system. The system includes a chamber 10 that embodies the features of the invention.

In use, the system separates whole blood within the chamber 10 into red blood cells (RBC) and plasma rich in platelets (called platelet-rich plasma, or PRP). This specification and drawings will identify red blood cells as RBC; platelet-rich plasma as PRP; and whole blood as WB.

The system includes a holder 12 that rotates the chamber 10 about an axis 14 (see FIG. 2), to thereby create a centrifugal field within the chamber 10. The centrifugal field extends from the rotational axis 14 radially through the chamber 10.

As FIG. 3 shows, the chamber wall 16 closest to the rotational axis 14 will be subject to a lower centrifugal force (or G-force) than the chamber wall 18 farthest away from the rotational axis 14. Consequently, the closer chamber wall 16 will be called the low-G wall, and the farthest chamber wall 18 will be called the high-G wall.

While rotating, the chamber 10 receives WB through a first port 20. The WB follows an axial flow path in the chamber 10. That is, it flows in a path that is generally parallel to the rotational axis 14 (as FIG. 2 best shows). Consequently, the chamber 10 will be called an axial flow blood processing chamber.

In the geometry shown in FIGS. 1 and 2, the transverse top and bottom edges of the axial flow chamber 10 (which lie across the axial flow path) are shorter than the longitudinal side edges (which lie along the axial flow path). Still, alternative geometries are possible. For example, the transverse top and bottom edges can extend 360 degrees to form a bowl, the outer periphery of which constitutes an axial flow chamber.

WB separates within the chamber 10 under the influence of the centrifugal field into RBC and PRP. As FIG. 3 shows, the higher density RBC move toward the high-G wall 18, displacing the lighter density PRP toward the low-G wall 16. A second port 22 draws the RBC from the chamber 10 for collection. A third port 24 draws the PRP from the chamber 10 for collection.

An intermediate layer called the interface 26 forms between the RBC and PRP. The interface 26 constitutes the transition between the formed cellular blood components and the liquid plasma component. Large amounts of white blood cells and lymphocytes populate the interface 26.

Platelets, too, can leave the PRP and settle on the interface 26. This settling action occurs when the radial velocity of the plasma near the interface 26 is not enough to keep the platelets suspended in the PRP. Lacking sufficient radial flow of plasma, the platelets fall back and settle on the interface 26.

One aspect of the invention establishes flow conditions within the chamber 10 to "elute" platelets from the interface 26. The elution lifts platelets from the interface 26 and into suspension in the PRP.

To establish beneficial elution conditions within the chamber 10, the PRP collection port 24 and the WB inlet port 20 are juxtaposed so that the PRP exits the chamber 10 in the same region where WB enters the chamber 10.

The illustrated embodiment, as shown in FIG. 1, locates the PRP collection port 24 on the same transverse edge of the chamber 10 as the WB inlet port 20. In FIGS. 1 to 3, this transverse edge is located physically at the top of the chamber 10.

The invention also arranges the RBC collection port 22 and the PRP collection port 24 so that PRP exits the chamber 10 in a region opposite to the region where RBC exit the chamber 10, relative to the axial flow of WB in the chamber 10.

The illustrated embodiment, as FIG. 1 shows, locates the RBC collection port 22 on the transverse edge that is opposite to transverse edge where the WB inlet and PRP collection ports 20 and 24 are located. In FIGS. 1 to 3, this transverse edge is located physically at the bottom of the chamber 10.

It should be appreciated that the centrifugal field is not sensitive to "top" and "bottom" port placement. The particular "top edge" and "bottom edge" relationship of the ports 20; 22; and 24 shown in FIGS. 1 to 3 could be reversed, placing the WB inlet and PRP collection ports 20 and 24 on the bottom edge and the RBC collection port 22 on the top edge.

Figure 4:
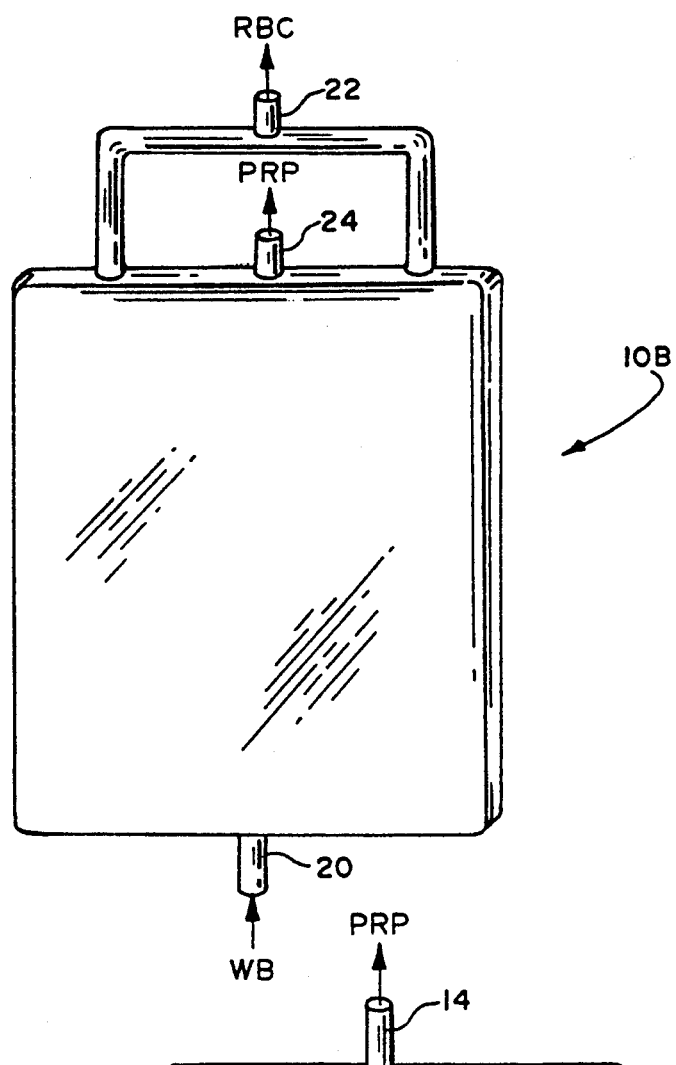
FIGS. 4 and 5 are diagrammatic views of prior art axial flow blood processing chambers.
Figure 5:
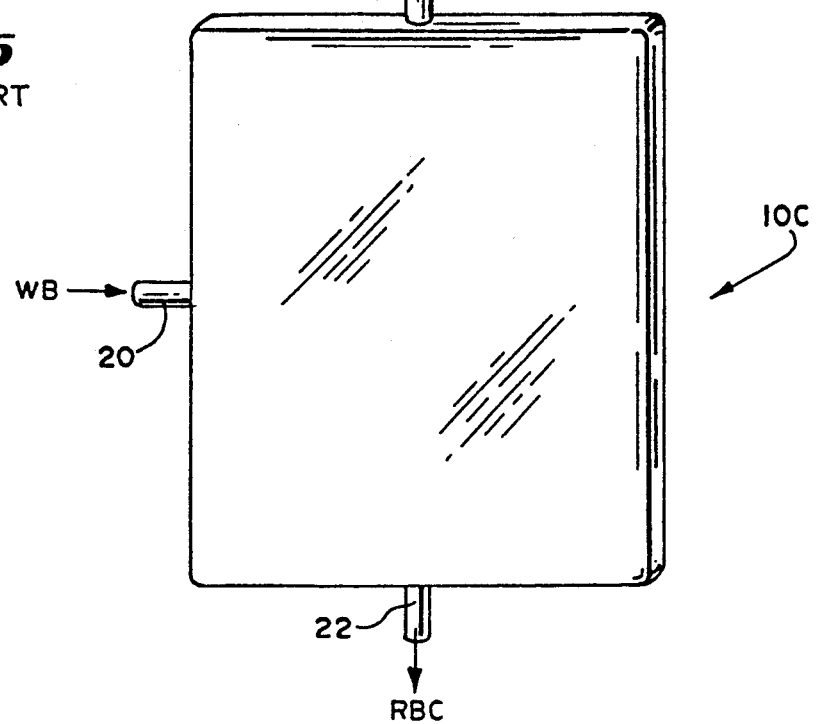

The chamber 10 shown in FIGS. 1 to 3 differs significantly from prior axial flow blood separation chambers 10A and 10B, which FIGS. 4 and 5 show. As there shown, the prior chambers 10A and 10B do not place the PRP collection port 24 and the WB inlet port 20 on the same transverse edge of the chamber. Instead, the prior chambers 10A and 10B purposely separate these ports 20 and 24 on different edges of the chamber.

In the prior chamber 10A shown in FIG. 4, the PRP collection port 24 and the WB inlet port 20 occupy opposite transverse edges of the chamber. In FIG. 4, the PRP collection port 24 occupies the top transverse edge, and the WB inlet port 20 occupies the bottom transverse edge. In this construction, there are two RBC collection ports 22, which occupy the same transverse edge as the PRP collection port 24 and which a Y-connector joins. This port arrangement is shown in Cullis U.S. Pat. No. 4,146,172.

In the prior chamber 10B shown in FIG. 5, the PRP collection port 24 occupies a transverse (top) edge of the chamber, while the WB inlet port 20 occupies a longitudinal (side) edge. In this construction, the RBC collection port 22 occupies an opposite (bottom) transverse edge of the chamber. This arrangement locates the WB inlet port 20 between the PRP collection port 24 and the RBC collection port 22.

To further enhance the platelet elution conditions within the chamber 10, the distance between the low-G wall 16 and the interface 26 is preferably smaller in the region of the RBC collection port 22 than in the region of the PRP collection port 24. The illustrated embodiment (see FIG. 3) achieves this result by uniformly tapering the low-G wall 16 toward the high-G wall 18 between the PRP collection port 24 and the RBC collection port 22. FIG. 3 shows the tapering low-G wall 16 in phantom lines.

The same result can be obtained without continuously or uniformly tapering the low-G wall 16 along the entire length of the axial flow path between the PRP collection port 24 and the RBC collection port 22. The low-G wall 16 can begin its taper farther away from the PRP collection port 24 than FIG. 3 shows, closer to the region of the RBC collection port 22.

The axial flow processing chamber 10 configured according to this aspect of the invention serves to increase platelet yields due to the interplay of two principal dynamic flow conditions, one radial and the other axial in direction.

First, due to the juxtaposition of the WB inlet port 20 and the PRP collection port 24, the chamber 10 produces a dynamic radial plasma flow condition near the PRP collection port 24. The radial flow condition is generally aligned along the centrifugal force field. The radial plasma flow condition continuously elutes platelets off the interface 26 into the PRP flow next to the PRP collection port 24.

Second, by narrowing the gap between the low-G wall 16 and the interface 26 next to the RBC collection port 22, compared to the gap next to the PRP collection port 24, the chamber 10 produces a dynamic axial plasma flow condition between the two ports 22 and 24. The axial flow condition is generally transverse the centrifugal force field. The axial plasma flow condition continuously drags the interface 26 back towards the PRP collection port 24, where the higher radial plasma flow conditions exist to sweep the platelets off the interface 26.

FIG. 3 diagrammatically shows the enhanced platelet separation effect due to these complementary radial and axial flow conditions.

WB enters the chamber 10 at a given entry hematocrit, which indicates the volume of RBC per unit volume of WB. A typical healthy donor has a predonation hematocrit of about 42.5%.

The hematocrit of the blood lying on the boundary between the RBC and plasma along the interface 26 (called the surface hematocrit) remains at or substantially the same as the entry hematocrit in the entry region $R_e$ of the chamber 10 near the WB inlet port 20. FIG. 3A shows this entry region $R_e$ as lying to the left of the 0.40 surface hematocrit isoconcentration line (which is the same as the entry 40% hematocrit).

The size of the entry region $R_e$ varies according to the hematocrit of the blood entering the chamber 10. For a given chamber configuration, the lower the entry hematocrit is, the smaller the entry region $R_e$ becomes.

The size of the entry region $R_e$ also depends upon the strength of the centrifugal field within the chamber and the surface area of the chamber.

As FIG. 3A shows,, the surface hematocrit successively increases above its entry level outside the entry region $R_e$ along the length of the chamber 10 toward the terminal region $R_t$, where separation is halted. This is because more red blood cells separate and collect toward the high-G wall 18 along the length of the chamber 10.

FIG. 3A shows the increasing surface hematocrit along the interface 26 as intersected by isoconcentration lines 0.6 (representing a 60% surface hematocrit) to 0.9 (representing a 90% surface hematocrit).

Further details of the distribution of RBC during centrifugation in a chamber are set forth in Brown, "The Physics of Continuous Flow Centrifugal Cell Separation," *Artificial Organs*, 13 (1):4-20 (1989), from which FIG. 3A is taken.

As FIG. 3A shows, the surface hematocrit is least in the entry region $R_e$ of the chamber 10 near the WB inlet port 20. As FIG. 3 shows, the velocity at which the RBC settle toward the high-G wall 18 in response to centrifugal force is greatest in the entry region $R_e$. Because the surface hematocrit is the least, there is more plasma volume to displace in the entry region $R_e$.

This, in turn, increases the radial velocity at which plasma is displaced by the separating RBC mass in response to the centrifugal force field. As the RBC mass moves toward the high-G wall 18, the plasma is displaced in a radial flow path toward the low-G wall 16. As a result, relatively large radial plasma velocities occur in the entry region $R_e$.

These large radial velocities toward the low-G wall 16 elute large numbers of platelets from the RBC mass. As a result, fewer platelets remain entrapped on the interface 26 here than elsewhere in the chamber 10.

The purposeful arrangement of the ports 20; 22; and 24 in the separation chamber 10 also contributes to further enhanced elution of platelets. The WB inlet port 20 is diametrically spaced from the RBC collection port 22, but the WB inlet port 20 is alongside the PRP collection port 24. This isolation between the WB inlet port 20 and the RBC collection port 22 forces the RBC to traverse the entire axial length of the chamber 10 during processing. This maximizes its exposure to the centrifugal force field.

The isolation between the RBC collection port 22 and the PRP collection port 24 directs the RBC toward the RBC collection port 22. At the same time, it directs the PRP stream in the opposite direction toward the PRP collection port 24.

Furthermore, due to the displaced low-G wall 16, the distance between the low-G wall 16 and the interface 26 increases between the region of the RBC collection port 22 and the PRP collection port 24. As a result, the plasma layer along the interface 26 increases in radial depth in the intended direction of PRP flow, i.e., away from the RBC collection port 22 and toward the axially spaced PRP collection port 24. The plasma near the RBC collection port 22 is closer to the high-G centrifugation field than the plasma near the PRP collection port 24.

This shift in the relative position of the plasma between the two ports 22 and 24 causes the lighter plasma to move along the interface 26. The plasma moves swiftly away from the relatively more confined region closer to the high-G field (i.e., next to the RBC collection port 22), toward the relatively more open region closer to the low-G field (i.e., next to the PRP collection port 24).

This swiftly moving axial plasma flow actually drags the interface 26—and platelets entrapped within in—continuously toward the PRP collection port 24. There, the radial plasma velocities are the greatest to supply the greatest elution effect, lifting the entrapped platelets free of the interface 26 and into the PRP stream for collection through the port 24.

The close juxtaposition of the WB inlet port 20 and the PRP collection port 24 will alone result in improved platelet elutriation in the chamber 10, without altering the radial position of the low-G wall 16 relative to the interface 26. The enhanced radial flow conditions will alone keep the majority of the platelet population in suspensions in the PRP for collection.

The remaining minority of the platelet population constitutes platelets that are physically larger. These larger platelets typically occupy over $15 \times 10^{-15}$ liter per platelet (femtoliters, or cubic microns), and some are larger than 30 femtoliters. In comparison, most platelets average about 8 to 10 femtoliters (the smallest of red blood cells begin at about 30 femtoliters).

These larger platelets settle upon the interface 26 quicker than most platelets. These larger platelets are most likely to become entrapped in the interface 26 near the RBC collection port 22.

The axial plasma flow conditions established along the interface 26 by the displaced low-G wall 16 moves these larger, faster settling platelets with the interface 26. The axial plasma flow moves the larger platelets toward the PRP collection port 24 into the region of high radial plasma flow. The high radial plasma flow lifts the larger platelets from the interface 26 for collection.

The complementary flow conditions continuously lift platelets of all sizes from the interface 26 next to the PRP collection port 24. They work to free platelets of all sizes from the interface 26 and to keep the freed platelets in suspension within the PRP.

Simultaneously (as FIG. 3 shows), the counterflow patterns serve to circulate the other heavier components of the interface 26 (the lymphocytes, monocytes, and granulocytes) back into the RBC mass, away from the PRP stream.

As a result, the PRP exiting the PRP collection port 24 carries a high concentration of platelets and is substantially free of the other blood components.

B. Two Stage Separation Systems

FIGS. 6 to 10 show the physical construction of a two stage axial flow system 27 that embodies the features and benefits already discussed, as well as additional features and benefits.

As FIG. 6A shows, the system 27 includes an assembly 28 of two disposable separation and collection containers 31A and 31B linked by tubing to an umbilicus 29. The separation containers 31A/31B and associated tubing can be made of low cost medical grade plastic materials, like plasticized PVC.

In use, the container 31A constitutes an axial flow chamber in which RBC and PRP are separated from whole blood in a first processing stage. The container 31A embodies the features of the axial flow chamber 10, as previously described.

In use, the container 31B constitutes an axial flow chamber in which the PRP is further separated into platelet concentrate and platelet-depleted plasma (also called platelet-poor plasma) in a second processing stage. The specification and drawings will refer to platelet concentrate as PC and platelet-poor plasma as PPP. The container 31B embodies other aspects of the invention, which will be described in greater detail later.

In this configuration, the assembly 28 can be used in association with a commercially available blood processing centrifuge, like the CS-3000® Blood Separation Centrifuge made and sold by the Fenwal Division of Baxter Healthcare Corporation (a wholly owned subsidiary of the assignee of the present invention).

Figure 6B:
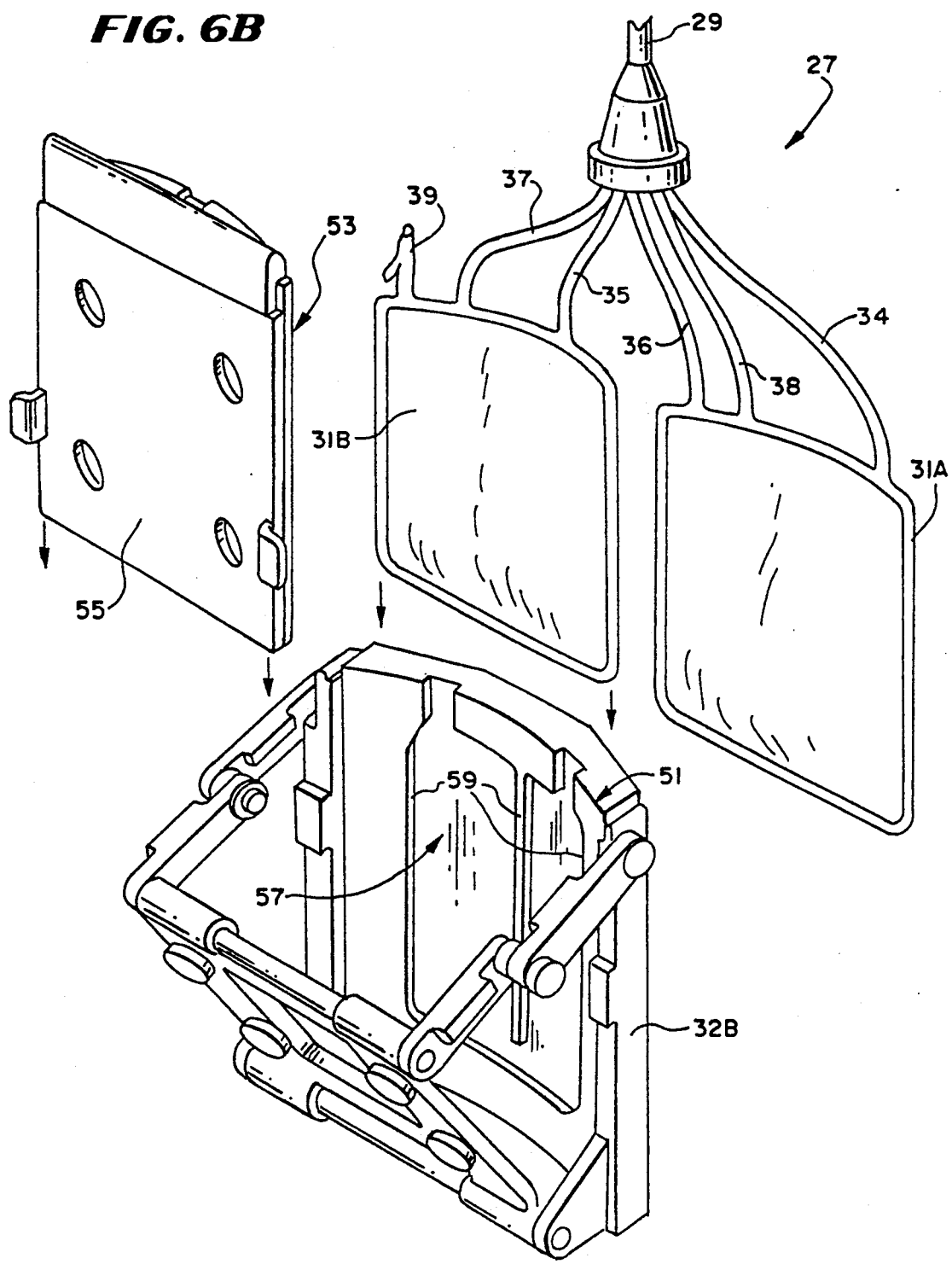
Figure 7A:
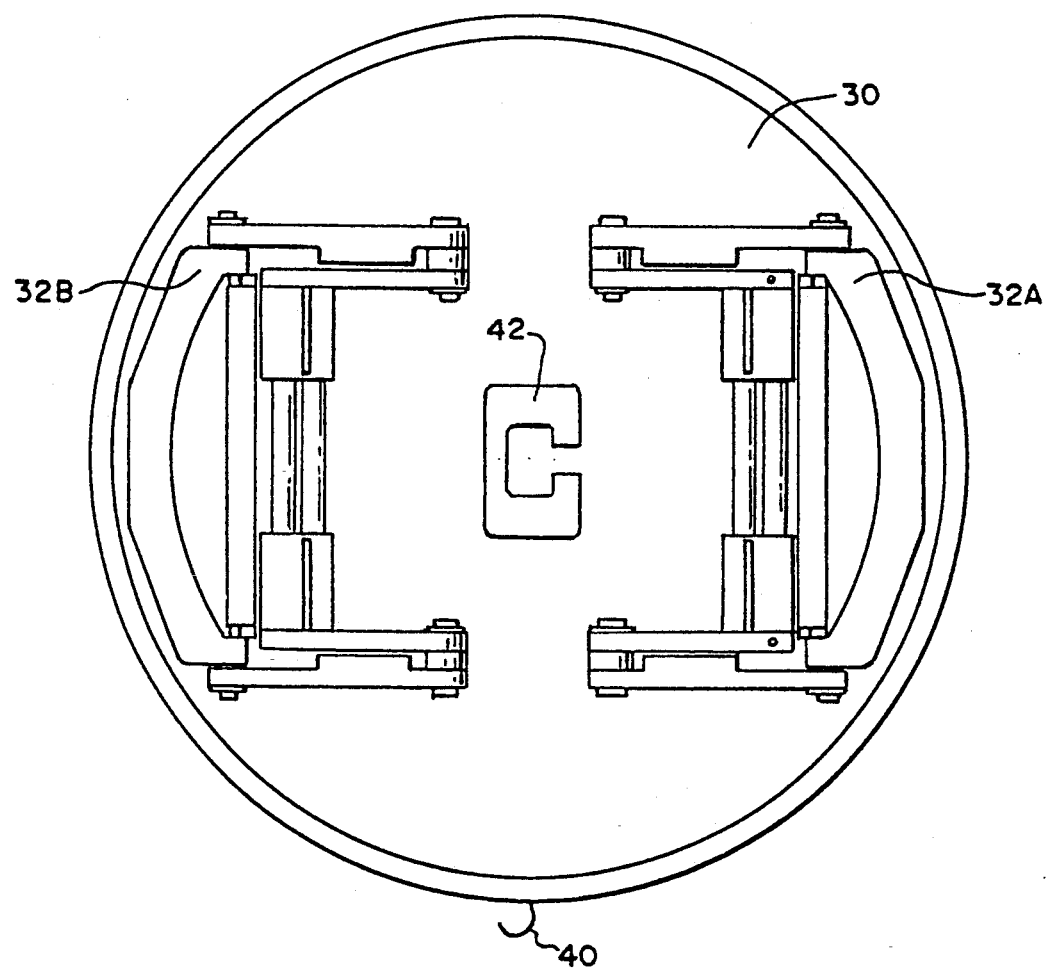
FIG. 7A is a top view of the blood processing assembly shown in FIG. 6 in position in a centrifuge.

As FIG. 7A best shows, the commercially available centrifuge includes a rotor 30 that carries two holders 32A and 32B, one for each container 31A and 31B. FIG. 6A shows the holder 32A for the first container 31A. FIG. 6B shows the holder 32B for the second container 31B.

Figure 8:
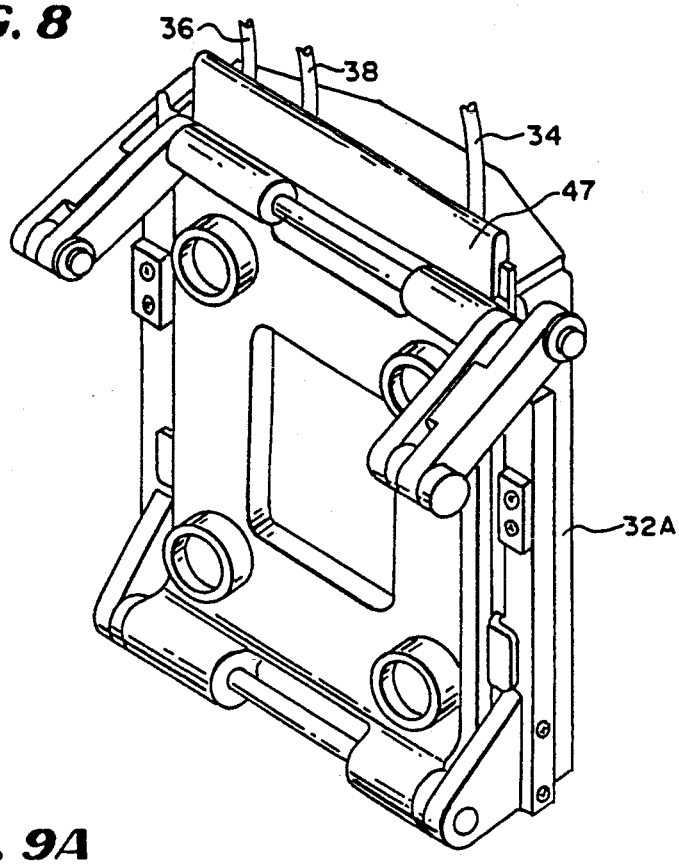
FIG. 8 is a perspective view of the first stage centrifuge holder associated with the assembly shown in FIG. 6A, when closed.

As FIGS. 6A/B show, each holder 32A/32B can be pivoted opened to receive its separation container 31A/31B. Each holder 32A/32B can then be pivoted closed (as FIG. 8 shows) to capture and enclose the associated separation container 31A/31B during processing.

In conventional use, the rotor 30 rotates (typically at about 1600 RPM), subjecting the holders 32A/32B and their entrapped separation containers 31A/31B to a centrifugal force field. Typically, the centrifugal force is field is about 375 G's along the high-g wall of the assembly 28.

As FIG. 6A shows, the first stage container 31A includes a series of ports through which the tubing umbilicus 29 conveys fluid. The container 31A receives WB through the port 34 for centrifugal separation into RBC and PRP. The ports 36 and 38 convey separated RBC and PRP, respectively, from the first container 31A.

PRP is conveyed from the first container 31A into the second stage container 31B. The second container 31B receives PRP through the port 35 for centrifugal separation into PC and PPP. The port 37 conveys PPP from the container 31B, leaving the PC behind within the container 31B for collection. A normally closed outlet port 39 is provided to later convey the PC from the container 31B.

As FIG. 7B best shows, the umbilicus 29 connects the rotating separation containers 31A/31B with pumps and other stationary components located outside the rotor 30. The stationary components include a pump P1 for conveying WB into the first container 31A. A pump P2 conveys PRP from the first container 31A to the second container 31B. An interface detector 33 senses the boundary between the RBC and plasma to control the operation of the pump P2.

The pump P2 pulls PRP away from the container 31A, until the detector 33 senses the presence of RBC. This indicates that the boundary between the RBC and the plasma has "spilled" past the detector 33. The pump P2 then pumps back toward the first container 31A until the sensed "spill-over" clears the interface detector 33. The pump P2 then reverses again to pull PRP away from the container 31A until the detector 33 senses another "spill-over." This process repeats itself.

Employing the well-known Cullis seal-less centrifuge principle, a non-rotating (zero omega) holder (not shown) holds the upper portion of the umbilicus 29 in a non-rotating position above the rotor. The holder 40 (see FIG. 7A) rotates the mid-portion of the umbilicus 29 at a first (one omega) speed about the rotor 30. The holder 42 (also see FIG. 7A) rotates the lower end of the umbilicus 29 at a second speed twice the one omega speed (the two omega speed). The rotor 30 also rotates at the two omega speed.

This relative rotation of the umbilicus 29 and the rotor 30 keeps the umbilicus 29 untwisted, in this way avoiding the need for rotating seals.

Each separation container 31A and 31B conforms to the interior configuration defined by its respective holder 32A and 32B, when closed.

1. First Stage Separation Chamber

Figure 9A:
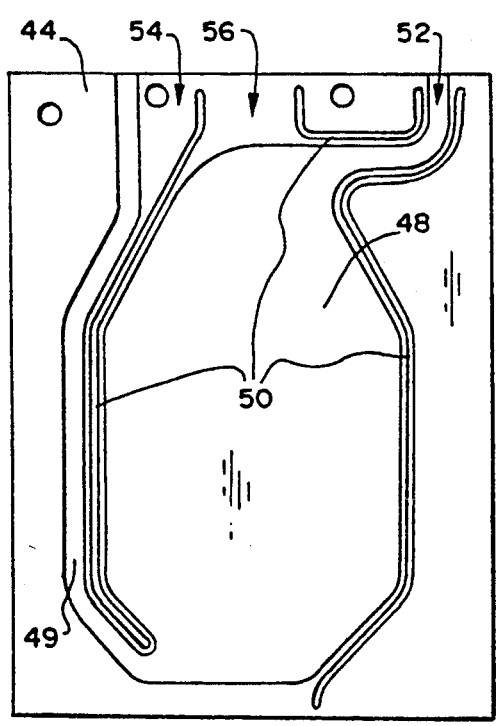
FIG. 9A is a plan view of the high-G surface of the first stage holder shown in FIG. 6A.
Figure 9B:
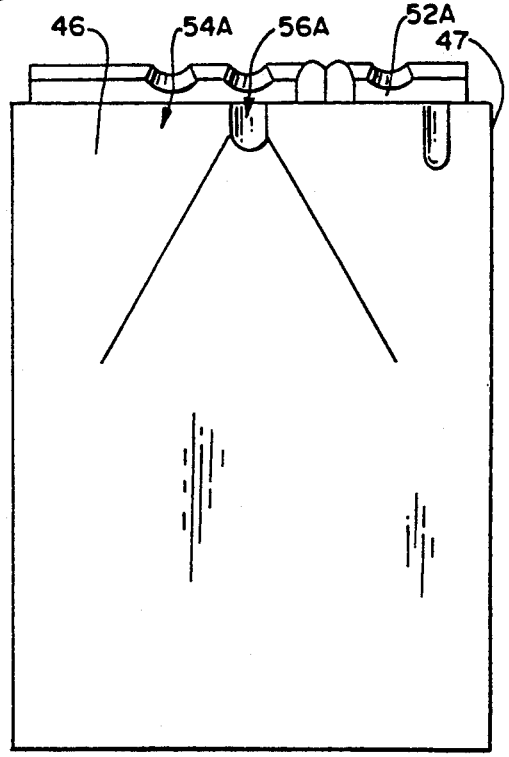
FIG. 9B is a plan view of the low-G surface of the first stage holder shown in FIG. 6A.

More particularly, as FIG. 6A shows, the holder 32A for the first stage container 31A includes a preformed high-G surface 44, also shown in FIG. 9A. The holder 32A also includes a facing preformed low-G surface 46, also shown in FIG. 9B. As FIG. 6A shows, the surface 46 is formed on a pressure plate 47 that is inserted into the holder 32A.

When closed, the holder 32A sandwiches the flexible separation container 31A between the high-G surface 44 and the surface of the low-G surface 46 (as FIG. 8 shows).

As FIGS. 6A and 9A show, the high-G surface 44 includes a prescribed recessed region 48 from which a pattern of raised sealing surfaces 50 project. When the holder 32A is closed, the pressure plate 47 presses the low-G surface 46 against the sealing surfaces 50. The pressure plate surface 46 crimps the walls of the separation container 31A closed along these sealing surfaces 50. This forms a prescribed peripherally sealed region within the container 31A occupying the recessed region 48.

When filled with blood during processing, the peripherally sealed region of the container 31A expands against the high-g surface 44 and the facing low-g surface of the pressure plate 46, assuming their prescribed contours.

As FIGS. 6A and 9A best show, the pattern of the raised sealing surfaces 50 establishes first, second, and third port regions 52; 54; and 56 extending into the recessed region 48. The first port region 52 receives the WB inlet port 34 of the container 31A. The second port region 54 receives the RBC collection port 36 of the container 31A. The third port region 56 receives the PRP collection port 38 of the container 31A.

As FIGS. 6A and 9A show, the first port region 34 (receiving WB inlet port 34) and the third port region 56 (receiving the PRP collection port 38) enter the recessed region 48 on the same transverse edge of the high-G surface 44 (which is shown as the top edge in the drawings). The second port region 54 (receiving the RBC collection port 36) enters the recessed region 48 through a passage 49 that opens on the opposite transverse edge of the high-G surface 44 (which is shown as the bottom edge in the drawings). Of course, as previously stated, the relative orientation of the transverse top and bottom edges could be reversed.

When the holder 32A is closed, mating regions 52A; 54A; and 56A on the low-G pressure plate 46 (see FIG. 9B) register with the first, second, and third port regions 52; 54; and 56 on the high-G surface 44 to receive the WB, RBC and PRP ports 34; 36; and 38 (see FIG. 8 also).

In the illustrated embodiment, the low-G pressure plate surface 46 preferably tapers outward toward the high-G surface at a slope of about 0.25 degree.

When closed, the holder 32A thereby shapes the peripherally sealed region of the container 31A to establish an axial flow processing chamber 10 like that shown in FIGS. 1 to 3.

In use, the first stage separation chamber 32B preferably presents an effective collection area of between about 70 to about 120 cm², with an associated processing volume of between about 45 ml to about 100 ml.

2. The Second Stage Separation Chamber

Figure 10A:
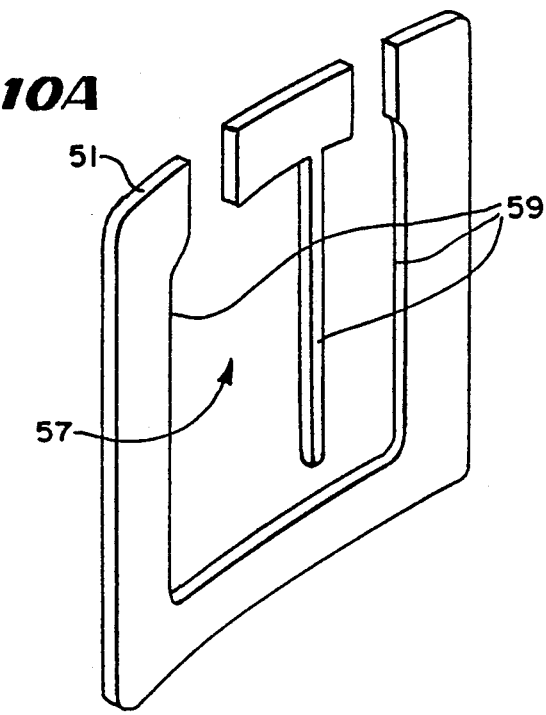
FIG. 10A is a perspective view of the high-G surface of the second stage holder shown in FIG. 6B.

As FIG. 6B shows, the holder 32B for the second stage container 31B, like the other holder 32A, includes a preformed high-G surface 51, which FIG. 10A also shows. The holder 32B also includes a facing preformed low-G pressure surface 53 formed on an insertable pressure plate 55.

Like the holder 32A, the high-G surface 51 of the holder 32B includes a recessed region 57 from which a pattern of raised sealing surfaces 59 project (see FIGS. 6B and 10A).

Like the holder 32A, when the holder 32B is closed, the pressure plate low-G surface 53 presses against the sealing surfaces 59. This crimps the walls of the separation container 31B closed along the sealing surfaces 59. The interior configuration of the second stage axial flow separation chamber 61 is thereby formed, as FIG. 10B shows.

Figure 10B:
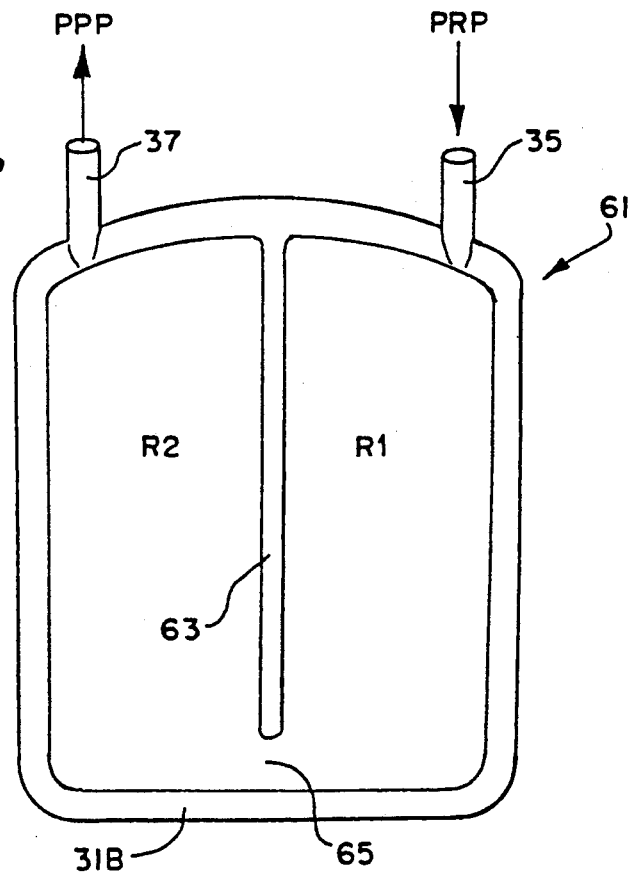
FIG. 10B is a plan view of the contours of the second stage centrifugation chamber, when in its operative position in the centrifuge holder.

As FIG. 10B shows, the pattern of the raised sealing surfaces 59 establishes first and second regions R1 and R2 within the chamber 61. The first region R1 communicates with the PRP inlet port 35 of the container 31B. The second port region R2 communicates with the PPP collection port 37 of the container 31B.

The raised sealing surfaces 59 also establish an interior wall 63 that separates the first and second regions R1 and R2. The wall 63 stretches into the chamber 61, extending in the same direction as the axial flow path. The wall 63 terminates within the chamber 61 to form a passage 65 linking the two regions R1 and R2. It should be appreciated that position of the wall 63 within the chamber 61 can vary. It can be closer to the PRP inlet port 35 than shown in FIG. 10B, thereby decreasing the size of the first region R1, and vice versa.

Figure 11:
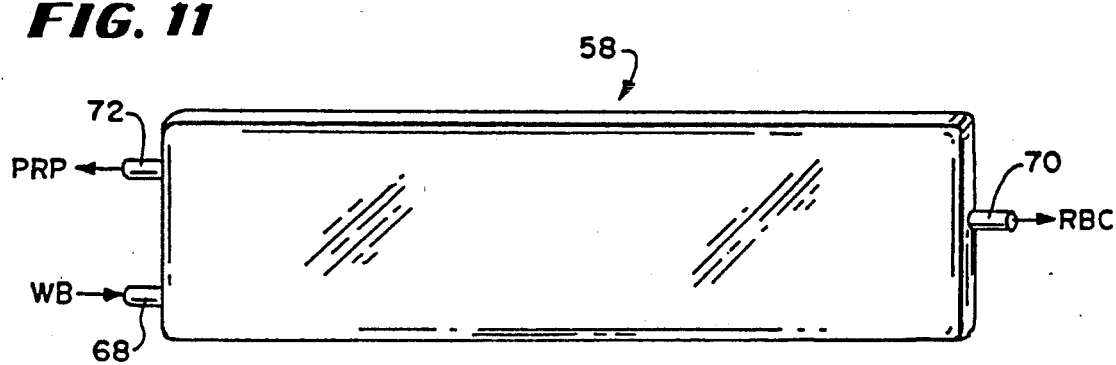
FIG. 11 is a diagrammatic view of an enhanced yield circumferential flow processing chamber that embodies the features of the invention.
Figure 12:
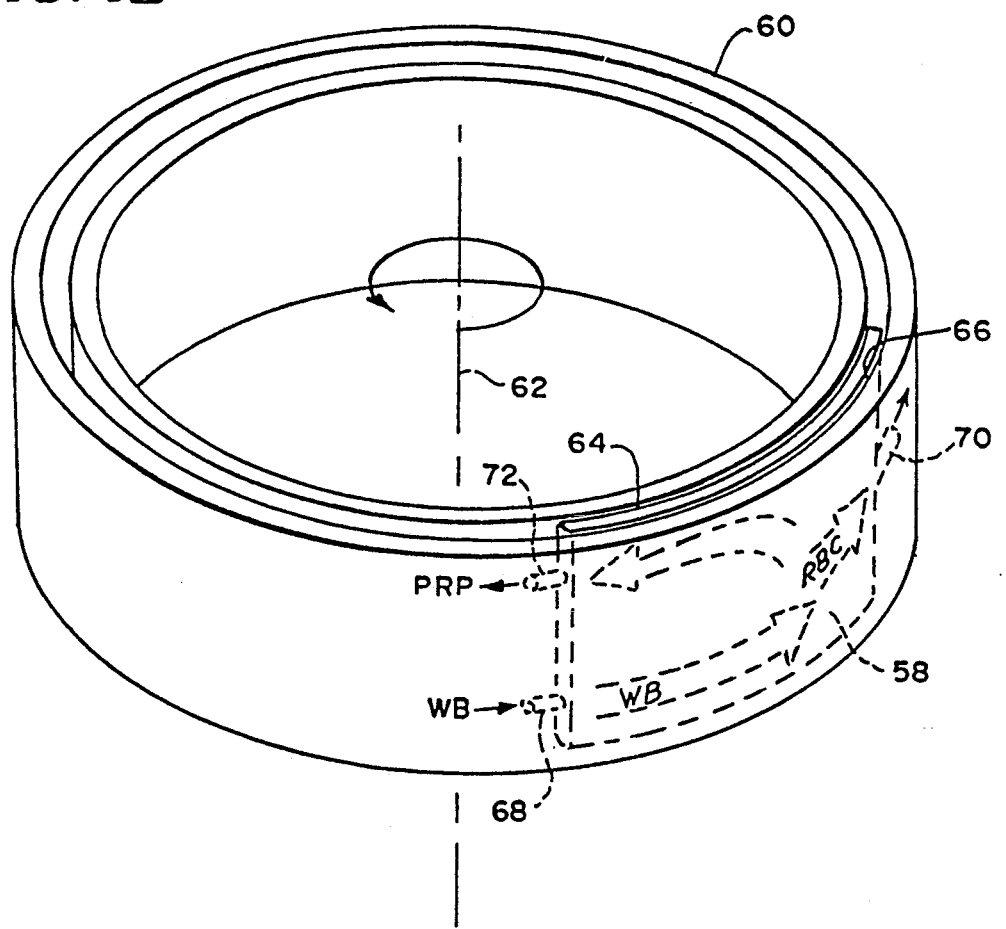
FIG. 12 is a diagrammatic view of the chamber shown in FIG. 11 operating in a centrifugation field.
Figure 13:
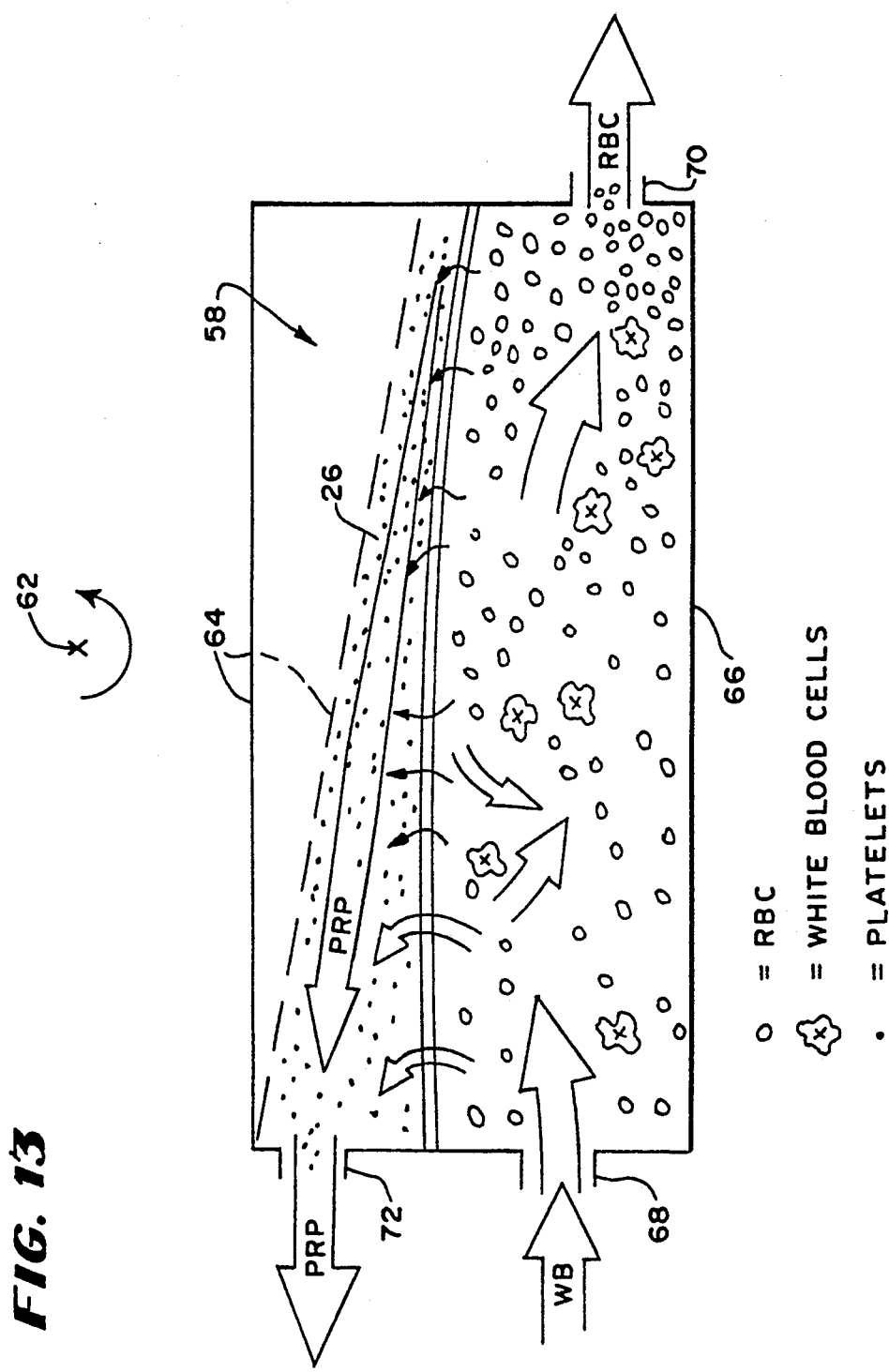
FIG. 13 is a diagrammatic view of the interior of the chamber shown in FIG. 11 when processing whole blood within the centrifugation field.

As just described, the configuration of the second stage chamber 61 is like that shown in FIGS. 11 to 13 in Cullis et al. U.S. Pat. No. 4,146,172. The Cullis et al. '172 Patent is incorporated into this Specification by reference.

A chamber like that shown in FIGS. 11 to 13 of the Cullis et al. '172 Patent has been in widespread commercial use in association with the CS-3000 ® Blood Separation Centrifuge for use in separating PC and PPP from PRP. The commercial chamber bears the trade designation "A-35 Chamber."

The prior A-35 Chamber typically has a collection area of about 160 cm² for separating PRP into PC and PPP. When used for this purpose, this chamber typically presents a radial thickness (or depth) on the order of about 1.4 cm. The chamber thereby has a processing volume of about 200 mL.

Conventional wisdom believed that the processing volume for second stage platelet separation chamber should exceed the processing volume of the first stage separation chamber.

The larger processing volume was believed to be beneficial, because it gave the platelets more time to separate (or "sediment") from the PRP within the chamber. Conventional wisdom also believed that the larger desired processing volume in the second stage chamber would subject the platelets to less damage or activation due to shear stress during processing (see, e.g., column 10, lines 26 to 39 of the Cullis et al. '172 Patent).

According to the present invention, the axial flow processing chamber 61 shown in FIG. 10B has a significantly smaller processing volume, compared to the prior A-35 Chamber.

In one operative embodiment, the chamber 61 configured according to the invention presents the same collection area as the prior A-35 Chamber (i.e., about 160 cm²), but has a maximum radial (or channel) depth of only 2 mm. In this operative embodiment, the chamber 61 presents a processing volume of just 30 mL, compared to the 200 mL processing volume typical for the prior A-35 Chamber.

Surprisingly, despite its considerably smaller processing volume and radial depth, the following Example demonstrates that the chamber 61 provides a significant increase in platelet collection efficiencies, compared to the prior A-35 Chamber.

Example 1

A study compared the conventional 200 ml A-35 chamber to the 30 ml, reduced depth chamber described above (which will be called the "30 ml Chamber"). Both chambers had a collection area of 160 cm².

The study used a paired run protocol. During the protocol, 59 normal donors underwent a platelet collection procedure with the A-35 chamber. The same donors underwent another platelet collection procedure with the 30 ml Chamber. The order of the collection procedures was randomized among the donors, with the procedures performed about a month apart.

Both procedures were conducted on a CS-3000® Centrifuge operated at a speed of 1600 RPM. All operating parameters for the first procedure were repeated in the second procedure. Six different blood centers participated in the study.

The results were correlated and statistically verified.

The study showed that the 30 ml Chamber provided significantly improved platelet collection. Compared to the A-35 Chamber, the 30 ml Chamber showed a 13.3% increase in platelet yield ($p < 0.0001$), which represents a significant increase in the net number of platelets collected during a given procedure.

Compared to the A-35 Chamber, the 30 ml Chamber provided increased platelet yields without damage or activation of the platelets. The platelet concentrate collected using the 30 ml Chamber could be filtered immediately after resuspension, without platelet loss. On the other hand, platelet concentrate collected using the A-35 Chamber required a rest period of at least 2 hours before it could be filtered without incurring a significant loss in platelet count.

Using the conventional dimensionless Reynolds Number (Re) as a point of comparison, one would conclude that the nature of the fluid flow in the A-35 Chamber and the 30 ml Chamber are virtually identical. The A-35 has a Re of 2.9, and the 30 ml Chamber has a Re of 7, which are not significantly different values.

One aspect of the invention provides a new dimensionless parameter ($\lambda$) that more accurately characterizes the combined attributes of angular velocity, channel thickness, kinematic viscosity, and axial height of the platelet separation chamber 61. The new parameter ($\lambda$) is expressed as follows:

$$\text{where } \lambda = \frac{(2\Omega h^3)}{(\nu Z)}$$

where:

$\Omega$ is the angular velocity (in rad/sec);

h is the radial depth (or thickness) of the chamber (in cm);

$\nu$ is the kinematic viscosity of the fluid being separated (in cm²/sec); and

Z is the axial height of the chamber (in cm).

As Table 1 shows, the parameter ($\lambda$) value clearly characterizes and differentiates the unique nature and domain of the flow regime established within the chamber 61 (referred to as the "New" chamber), compared to the conventional A-35 chamber.

TABLE 1

| | | Chamber Type | |
|---|---|---|---|
| | | A-35 Chamber | New |
| Fluid | | Plasma | Plasma |
| Volume | mL | 200 | 30 |

TABLE 1-continued

| | | Chamber Type | |
|---|---|---|---|
| | | A-35 Chamber | New |
| $\nu$ | cm²/sec | 0.012 | 0.012 |
| Flow Rate | mL/min | 25 | 25 |
| Speed | RPM | 1600 | 1600 |
| Thickness | cm | 1.4 | 0.2 |
| Height | cm | 15 | 15 |
| $\lambda$ | $2\Omega h^3/\nu Z$ | 5109 | 14 |
| Re | $Q/\nu Z$ | 3.5 | 7 |

As Table 1 shows, the parameter ($\lambda$) value for the prior A-35 Chamber is 5109. The parameter ($\lambda$) value for the chamber that embodies the features of the invention is only 14, less than 1% of the prior chamber.

According to this aspect of the invention, a parameter ($\lambda$) value for a chamber that is less than about 700 will produce significantly greater platelet yields. As the parameter ($\lambda$) value of a given chamber increasingly exceeds about 700, the chamber produces flow conditions that lead to greater overall shear stress during processing (leading to platelet activation) and to greater Coriolis-effect swirling (which limits the effective surface area available for platelet perfusion).

The new parameter ($\lambda$) value expresses for a given rotating frame of reference what the magnitude of Coriolis-effect swirling and shear stress will be. The parameter ($\lambda$) value has the same meaning whether the flow within the chamber is axial (i.e., along the axis of rotation) or circumferential (i.e., about the axis of rotation). Regardless of the direction of flow with respect to the rotational axis, the lower the absolute parameter ($\lambda$) value is for a given system, the lower will be the expected magnitude of Coriolis-effect swirling in the system. The chamber 61 has a parameter ($\lambda$) value that is less than about 700, it is better perfused during processing and subjects the platelets to less shear stress, even at dramatically reduced chamber depths (i.e. radial thickness).

II. Enhanced Yield Circumferential Flow Chambers

The aspects of the invention previously described in the context of an axial flow blood separation chamber can also be employed in providing a circumferential flow blood processing chamber with enhanced platelet separation efficiencies.

FIGS. 11 to 13 show, in diagrammatic fashion, a circumferential flow centrifugal blood processing chamber 58 that embodies the features of the invention.

In use, the chamber 58 rotates on a rotor 60 about an axis 62 (see FIG. 12), to thereby create a centrifugal field within the chamber 58. Just as with the axial flow chamber 10 shown in FIGS. 1 to 3, the centrifugal field extends radially from the axis through the chamber 58. As FIG. 13 shows, the chamber wall 64 closest to the axis constitutes the low-G wall, and the chamber wall 66 farthest from the axis constitutes the high-G wall.

While rotating, the chamber 58 receives WB through a first port 68. The WB follows a circumferential flow path in the chamber 58; that is, it flows in a circumferential path about the rotational axis 62 (as FIG. 12 best shows). For this reason, the chamber 58 is called a circumferential flow blood processing chamber.

In this geometry, the transverse top and bottom edges of the chamber 58 (which lie along the circumferential flow path) are usually longer than the longitudinal side edges (which lie across the circumferential flow path). The circumferential flow chamber 58 usually forms the shape of a tube that is elongated in the direction of rotation. Still, other configurations defining a circumferential flow path can be used.

WB separates within the tubular chamber 58 under the influence of the centrifugal field into RBC and PRP. As FIG. 13 shows, the higher density RBC move toward the high-G wall 66, displacing the lighter density PRP toward the low-G wall 64. The interface 26 (previously described) forms between them. A second port 70 draws the RBC from the chamber 58 for collection. A third port 72 draws the PRP from the chamber 58 for collection.

According to the invention, the PRP collection port 72 and the WB inlet port 68 are juxtaposed so that the PRP exits the circumferential flow chamber 58 in the same region where WB enters the chamber 58. In the illustrated embodiment, as shown in FIG. 11, the PRP collection port 72 is located along the same longitudinal side edge of the circumferential flow chamber 58 as the WB inlet port 68.

Also according to the invention, the RBC collection port 70 and the PRP collection port 72 are arranged so that PRP exits the chamber 58 in a region opposite to the region where RBC exit the chamber 58, relative to the circumferential flow of WB in the chamber 58. In the illustrated embodiment, as FIG. 11 shows, the RBC collection port 70 is located on the longitudinal side edge that is opposite to longitudinal side edge where the WB inlet and PRP collection ports are located.

Figure 14:
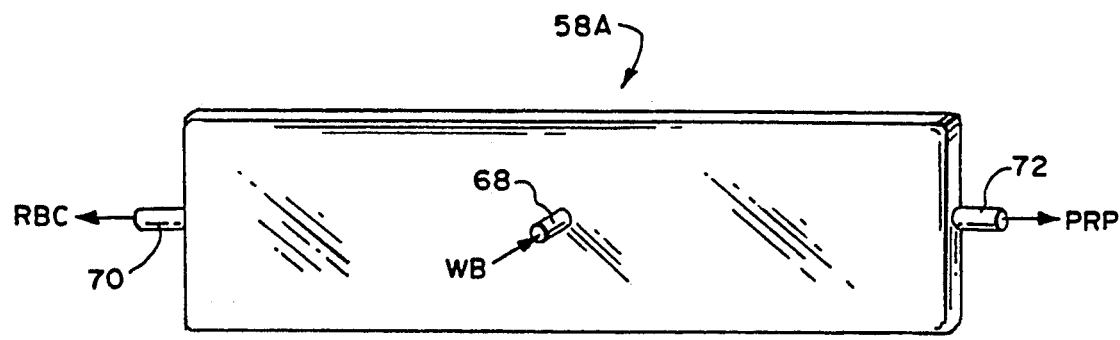
FIGS. 14 and 15 are diagrammatic views of prior art circumferential flow blood processing chambers.
Figure 15:
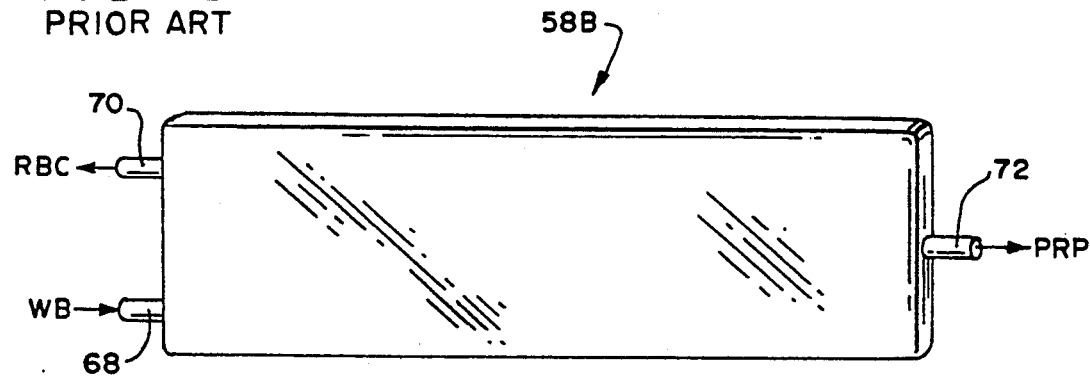

The chamber 58 shown in FIGS. 11 to 13 differs significantly from prior circumferential flow blood separation chambers 58A and 58B, which are shown in FIGS. 14 and 15. The prior circumferential flow chambers 58A/B purposely located the PRP collection port 72 away from the WB inlet port 68.

In the prior circumferential flow chamber 58A shown in FIG. 14, the PRP collection port 72 occupies one side edge, diametrically opposite to the RBC collection port 70, which occupies the other side edge. In this construction, the WB inlet port 68 is located in a side wall of the chamber 58A between the two side edges.

In the prior circumferential flow chamber 58B shown in FIG. 15, the PRP collection port 72 occupies one side edge, while the WB inlet port 68 and the RBC outlet port occupies the opposite side edge, oppositely spaced away from the PRP collection port 72 relative to the circumferential flow of WB in the chamber 58B.

In both the FIG. 14 construction and the FIG. 15 construction, no ports are located on the top and bottom transverse edges of the chamber 58B. Neither chamber 58A and 58B has a port with an axis that extends parallel to the axis of rotation.

FIG. 13 diagrammatically shows the enhanced platelet separation effect due to the adjacent positions of the WB inlet port 68 and the PRP collection port 72 in the circumferential flow chamber 58 that embodies the invention. The effect is generally the same as that shown in FIG. 3, except the chamber 58 is oriented differently to establish the circumferential flow pattern.

As FIG. 13 shows, the PRP collection port 72 draws PRP from the chamber 58 where velocity at which the RBC settle toward the high-G wall 66 in response to centrifugal force is the greatest, i.e., next to the WB inlet port 68. Here, too, is where the radial plasma velocity is the greatest to lift platelets from the interface 26, and to keep them in suspension within the plasma for transport out the PRP collection port 72.

The WB inlet port 68 is oppositely spaced from the RBC collection port 70 (in the circumferential flow direction), forcing the RBC to traverse the entire axial length of the chamber 58, thereby maximizing their exposure to the centrifugal separation forces. The isolation between the RBC collection port 70 and the PRP collection port 72 also directs the RBC toward the RBC collection port 70, while directing the PRP stream in the opposite direction toward the PRP collection port 72.

Like the chamber 10 shown in FIG. 3, the low-G wall 64 is preferably displaced inward toward the interface 26 near the RBC collection port 70. As a result, the radial distance between the low-G wall 64 and interface 26 is greater near the PRP collection port 72 than near the RBC collection port 70.

As previously described with reference to FIG. 3, the displaced low-G wall 64 causes the lighter plasma to move along the interface 26 swiftly away from the relatively more confined region next to the RBC collection port 70, toward the relatively more open region next to the PRP collection port 72. The same beneficial effect results: the circumferential plasma flow drags the interface 26—and larger, faster settling platelets entrapped within in—continuously toward the PRP collection port 72, where the radial plasma velocities are the greatest to supply the greatest elution effect. The counterflow patterns also serve to circulate the other heavier components of the interface (lymphocytes, monocutes, and granulocytes) back into the RBC mass, away from the PRP stream.

As FIG. 13 shows, the low-G wall 64 continuously tapers in the direction of the circumferential flow path, e.g., away from the PRP collection port 72 and in the direction of axial flow path of the WB. The same result can be obtained without continuously or uniformly tapering the low-G wall 16 along the entire length of the axial flow path between the PRP collection port 72 and the RBC collection port 70. The low-G wall 16 can begin its taper farther away from the PRP collection port 24 than FIG. 13 shows, closer to the region of the RBC collection port 70.

The circumferential flow chamber 58 that embodies the invention can be variously constructed. FIGS. 16 and 17 show the physical construction of one preferred circumferential flow chamber assembly 74 that embodies the features of the invention. FIGS. 25 and 26 show the physical construction of an alternative circumferential flow assembly 76.

Either assembly 74 or 76 can be used in association with a blood processing centrifuge 78, like that shown in FIGS. 18 and 19. Further details of this centrifuge construction are set forth in copending U.S. patent application Ser. No. 07/814,403, filed Dec. 23, 1991 and entitled "Centrifuge with Separable Bowl and Spool Elements Providing Access to the Separation Chamber".

Figure 20:
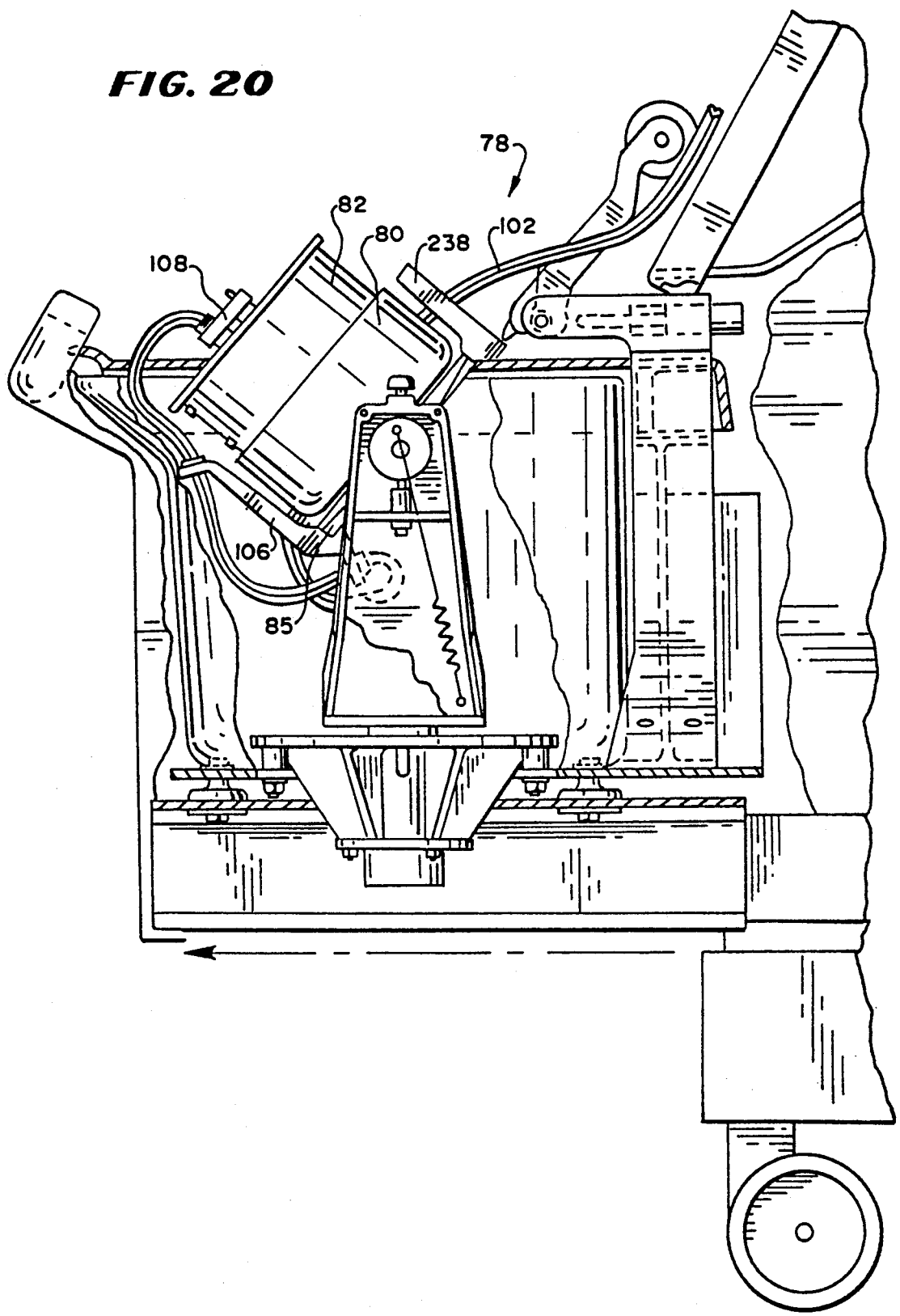
FIG. 20 is a side view of a centrifuge that can be used in association with either one of the blood processing assemblies shown in FIGS. 16/17 or 18/19, showing the bowl and spool assemblies in their upraised and separated position.

As FIG. 20 shows, the centrifuge 78 includes a bowl element 80 and a spool element 82. The bowl and spool elements 80 and 82 can be pivoted on a yoke 85 between an upright position, as FIG. 20 shows, and a suspended position, as FIG. 21 shows.

Figure 22:
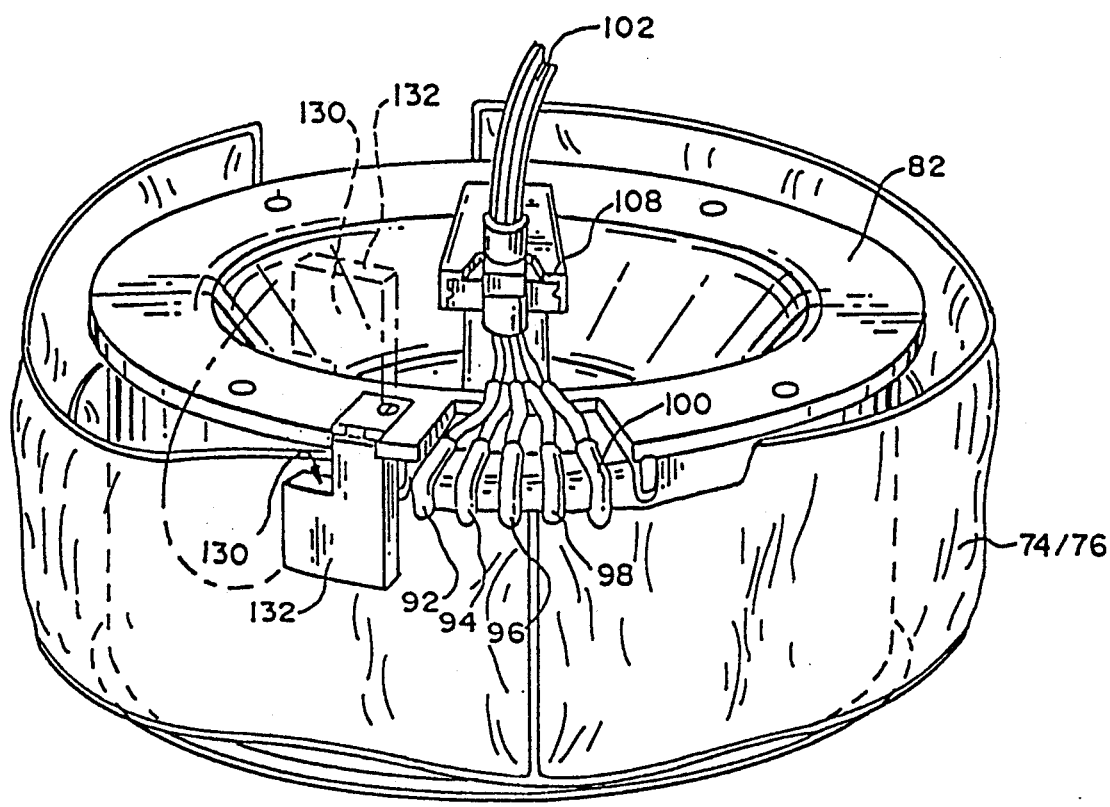
FIG. 22 is an enlarged perspective view of one of the blood processing assemblies shown in FIGS. 16/17 or 18/19 being wrapped for use about the spool of the centrifuge shown in FIG. 20.

When upright, the bowl and spool elements 80 and 82 are presented for access by the user. A mechanism permits the spool and bowl elements 80 and 82 to assume a mutually separated position, as FIG. 20 shows. In this position, the spool element 80 is at least partially out of the interior area of the bowl element 82 to expose the exterior spool surface for access. As FIG. 22 shows, when exposed, the user can wrap either circumferential flow chamber assembly 74 or 76 about the spool element 82.

Figure 23:
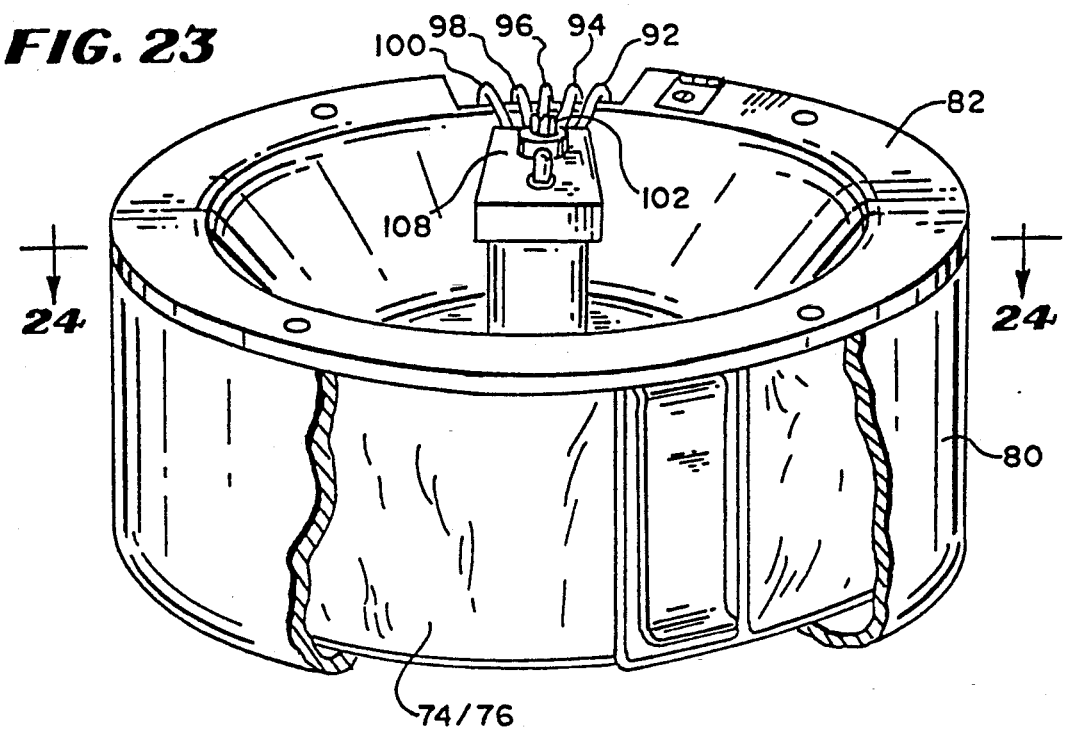
FIG. 23 is an enlarged perspective view, with portions broken away, of one of the blood processing assemblies shown in FIGS. 16/17 or 18/19 mounted for use on the bowl and spool assemblies of the centrifuge shown in FIG. 20.

The mechanism also permits the spool and bowl elements 80 and 82 to assume a mutually cooperating position, as FIG. 23 shows. In this position, the spool element 82 and the chosen circumferential flow chamber assembly 74 or 76 are enclosed within the interior area of the bowl element 80, as FIG. 23 shows. A processing chamber 83 is formed between the interior of the bowl element 80 and the exterior of the spool element 82. The chosen circumferential flow chamber assembly 74 or 76 is carried with and assumes the contours of the processing chamber 83.

Figure 21:
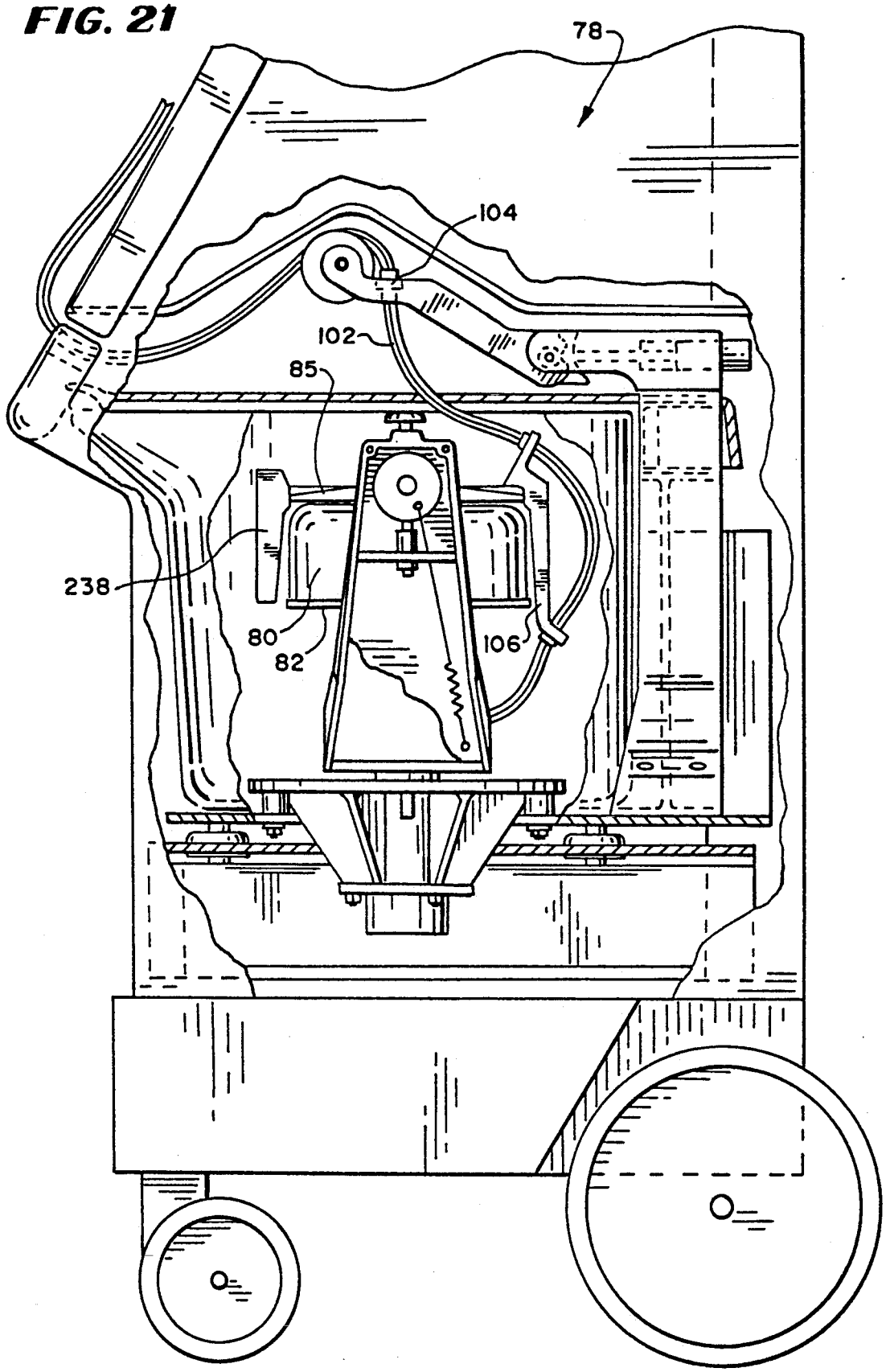
FIG. 21 is a side view of the centrifuge shown in FIG. 20, showing the bowl and spool assemblies in their suspended and operating position.

When closed, the spool and bowl elements 80 and 82 can be pivoted as an assembly into a suspended position, as FIG. 21 shows. When suspended, the bowl and spool elements 80 and 82 are in position for operation. In operation, the centrifuge 78 rotates the suspended bowl and spool elements 80 and 82 about an axis.

In the illustrated embodiments, each circumferential flow chamber assembly 74 and 76 provides multi-stage processing. A first stage separates RBC and PRP from WB. A second stage separates PC and PPP from the PRP.

While the interior of either circumferential flow chamber assembly 74 or 76 can be variously arranged, FIGS. 16/17 and 18/19 show the interior of the alternative circumferential flow chambers divided into two side-by-side processing compartments 84 and 86. In use, centrifugal forces in the first compartment 84 separate whole blood into RBC and PRP. Centrifugal forces in the second processing compartment 86 separate the PRP from the first stage into PC and PPP.

In both alternative circumferential flow chambers, a first peripheral seal 88 forms the outer edge of the circumferential flow chamber assembly 74 or 76. A second interior seal 90 divides the circumferential flow chamber assembly 74 or 76 into the first processing compartment 84 and the second processing compartment 86. The second seal 90 extends generally parallel to the rotational axis of the chamber assembly 74 or 76; that is, it extends across the circumferential flow of the chamber assembly 74 or 76. The second seal 90 constitutes a longitudinal edge common to both first and second processing compartments 84 and 86.

Each processing compartment 84 and 86 serves as a separate and distinct separation chamber and will therefore be referred to as such.

In each alternative circumferential flow chambers, five ports 92/94/96/98/100 open into the compartmentalized areas formed in the processing chamber assembly 74 or 76. The ports 92/94/96/98/100 are arranged side-by-side along the top transverse edge of the respective chamber 84 and 86.

The ports 92/94/96/98/100 are all axially oriented; that is, their axes are aligned with the axis of rotation, transverse the circumferential fluid flow path within the chamber assembly 74 or 76 itself. Three ports 92/94/96 serve the first chamber 84. Two ports 98/100 serve the second chamber 86.

In both alternative circumferential flow chamber assemblies 74 and 76, an umbilicus 102 (see FIG. 24) attached to the ports 92/94/96/98/100 interconnects the first and second chambers 84 and 86 with each other and with pumps and other stationary components located outside the rotating components of the centrifuge 78.

As FIG. 21 shows, a non-rotating (zero omega) holder 104 holds the upper portion of the umbilicus 102 in a non-rotating position above the suspended spool and bowl elements 80 and 82. A holder 106 on the yoke 85 rotates the mid-portion of the umbilicus 102 at a first (one omega) speed about the suspended spool and bowl elements 80 and 82. Another holder 108 (see FIG. 22) rotates the lower end of the umbilicus 102 at a second speed twice the one omega speed (the two omega speed), at which the suspended spool and bowl elements 80 and 82 also rotate. As before stated, this known relative rotation of the umbilicus keeps it untwisted, in this way avoiding the need for rotating seals.

Using either alternative circumferential flow chamber assembly 74 or 76, the two omega speed at which the suspended spool and bowl elements 80 and 82 rotate is about 3400 RPM. Given the dimensions of the spool and bowl elements 80 and 82, 3400 RPM will develop a centrifugal force field of about 900 G's along the high-G wall 66 of the chambers 84 and 86.

A. The First Stage Processing Chamber

In the embodiment shown in FIGS. 16 and 17, the first port 92 comprises the previously described PRP collection port (identified by reference numeral 72, as in FIGS. 11 to 13). The second port 94 comprises the previously described WB inlet port (identified by reference numeral 68, as in FIGS. 11 to 13). The third port 96 comprises the previously described RBC collection port (identified by reference numeral 70, as in FIGS. 11 to 13).

A third interior seal 110 is located between the PRP collection port 72 and the WB inlet port 68. The third seal 110 includes a first region 112 that is generally parallel to the second interior seal 90, thereby extending across the circumferential WB flow path. The third interior seal 110 then bends in a dog-leg portion 114 away from the WB inlet port 68 in the direction of circumferential WB flow. The dog-leg portion 114 terminates beneath the inlet of the PRP collection port 72.

A fourth interior seal 116 is located between the WB inlet port 68 and the RBC collection port 70. The fourth seal 116 includes a first region 118 that is generally parallel to the second and third interior seals 90 and 110, thereby extending across the circumferential WB flow path. The fourth interior seal 116 then bends in a dog-leg portion 120 away from the RBC collection port 70 in the direction of circumferential WB flow. The dog-leg portion 120 extends beneath and beyond the dog-leg portion 114 of the third seal 110. It terminates near the longitudinal side edge of the first chamber 84 that is opposite to the longitudinal side edge formed by the second interior seal 90.

Together, the third and fourth interior seals 110/116 form a WB inlet passage 122 that first extends along the axis of rotation (i.e., between the first regions 112/118 of the two seals 110/116). The WB inlet passage 122 then bends to open in the direction of intended circumferential flow within the first chamber 84 (i.e., between the dog-leg portions 114/120 of the two seals 110/116).

The WB inlet passage 122 first channels WB away from the WB inlet port 68 in an axial flow path. It then channels WB circumferentially, directly into the circumferential flow path, where separation into RBC and PRP begins.

The third interior seal 110 also forms a PRP collection region 124 within the first chamber 84 (i.e., between the third seal 110 and the adjacent upper portion of the first peripheral seal 88).

Together, the fourth interior seal 116, the second interior seal 90, and the lower regions of the first peripheral seal 88 form a RBC collection passage 126 that extends first along the axis of rotation (i.e., between the second interior seal 90 and the fourth interior seal 116). The RBC collection passage 126 then bends in a circumferential path to open near the end of the intended WB circumferential flow path (i.e., between the dog-leg portion 120 of the fourth seal 116 and the lower region of the peripheral seal 88).

In the embodiment shown in FIGS. 18 and 19, the first port 92 comprises the RBC collection port (identified by reference numeral 70, as in FIGS. 11 to 13). The second port 94 comprises the PRP collection port (identified by reference numeral 72, as in FIGS. 11 to 13). The third port 96 comprises the WB inlet port (identified by reference numeral 68, as in FIGS. 11 to 13).

As FIG. 18 shows, a third interior seal 110 is located between the PRP collection port 72 and the WB inlet port 68. The seal 110 includes a first region 112 that is generally parallel to the second interior seal 90. It then bends in a dog-leg portion 114 away from the WB inlet port 68 in the direction of circumferential WB flow. The dog-leg portion 114 terminates beneath the inlet of the PRP collection port 72.

Together, the second and third interior seals 90 and 110 form a WB inlet passage 122, like the WB inlet passage 122 associated with the chamber 84 shown in FIG. 16, except in a different location within the chamber.

As FIG. 18 shows, a fourth interior seal 116 is located between the PRP collection port 72 and the RBC collection port 70. The fourth seal 116 includes a first region 118 that is generally parallel to the second and third interior seals 90 and 110, thereby extending across the circumferential flow path. The fourth interior seal 116 then bends in a dog-leg portion 120 away from the PRP collection port 72 in the direction of circumferential WB flow. it terminates near the longitudinal side edge of the first chamber 84 that is opposite to the longitudinal side edge formed by the second interior seal 90.

Together, the fourth interior seal 116 and the upper regions of the first peripheral seal 88 form a RBC collection passage 126, like the RBC collection passage 126 shown in FIG. 16, except that it is located at the top of the chamber 84, instead of at the bottom.

As FIG. 18 shows, the third and fourth interior seals 110 and 116 together also form a PRP collection region 124 within the first chamber, like the PRP collection region 124 shown in FIG. 16.

The dynamic flow conditions within each alternative circumferential flow chamber assembly 74 or 76 are the same. These conditions direct PRP toward the PRP collection region 124 for collection through the inlet of the PRP collection port 72.

As FIGS. 16 and 18 show, the WB inlet passage 122 channels WB directly into the circumferential flow path immediately next to the PRP collection region 124. Here, the radial flow rates of plasma are greatest to lift platelets free of the interface and into the PRP collection region 124.

The RBC collection passage 126 receives RBC at its open end and from there channels the RBC to the RBC collection port 70. As FIGS. 16 and 18 show, the WB inlet passage 122 channels WB directly into the flow path at one end of the first chamber 84, and the RBC collection passage 126 channels RBC out at the opposite end of the flow path.

In each alternative circumferential flow chamber assembly 74 and 76 (as FIGS. 17 and 19 respectively show), the low-G wall 64 of the first chamber 84 is offset toward the high-G wall 66 near the RBC collection region.

In the particular embodiments shown, the low-G wall 64 tapers into the chamber 84 in the direction of circumferential WB flow. The taper proceeds from the second interior seal 90 toward the opposite longitudinal end of the chamber. FIG. 13 shows the tapering low-G wall 64 from another perspective.

The tapering low-G wall 64 includes a stepped-up barrier 128 or dam in the region where the RBC collection passage 126 opens. As FIGS. 16 and 18 show for their respective chamber assembly, the stepped-up barrier 128 extends from the low-G wall 64 across the entire chamber 84.

As FIG. 13 best shows from another perspective, the stepped-up barrier 128 extends into the RBC mass and creates a restricted passage 129 between it and the facing high-G wall 66. The restricted passage 129 allows RBC present along the high-G wall 66 to move beyond the barrier 128 for collection by the RBC collection passage 126. Simultaneously, the stepped-up barrier 128 blocks the passage of the PRP beyond it, keeping the PRP within the dynamic flow conditions leading to the PRP collection region 124.

While various configurations can be used, in a preferred arrangement, the low-G wall 64 tapers about 2 mm into the chamber 74 where it joins the barrier 128. The barrier 128 extends from there at about a 45 degree angle toward the high-G wall 66, forming a raised planar surface. The passage 129 formed between the planar surface and the high-G wall 66 is about 1 mm to 2 mm in radial depth and about 1 mm to 2 mm in circumferential length.

As previously described (and as FIG. 13 shows), the configuration of the low-G wall 64 creates a swift counterflow of plasma from the RBC collection region toward the PRP collection region 124.

The desired contours for the low-G wall 64 of the alternative chamber assemblies 74 and 76 can be preformed on the exterior surface of the spool element 82. In the illustrated embodiment, the interior surface of the bowl element 82 is isoradial with respect to the rotational axis.

Also in both alternative embodiments (as FIGS. 16 and 18 show), the dog leg portion 120 of the RBC collection passage 126 is tapered. Due to the taper, the passage 126 presents a greater cross section where it opens into the chamber 84 than it does where it joins the axial first region 118 of the RBC collection passage 126. FIG. 13 shows this taper from another perspective. In the illustrated and preferred embodiment, the dog leg portion 120 tapers from a width of about ¼ inch to ⅛ inch.

The taper of the dog leg portion 120 is preferably gauged relative to the taper of the low-G wall 64 to keep the cross sectional area of the RBC collection passage 126 substantially constant. This keeps fluid resistance within the passage 126 relatively constant, while maximizing the available separation and collection areas outside the passage 126. The taper of the dog leg portion 120 also facilitates the removal of air from the passage 126 during priming.

Figure 24:
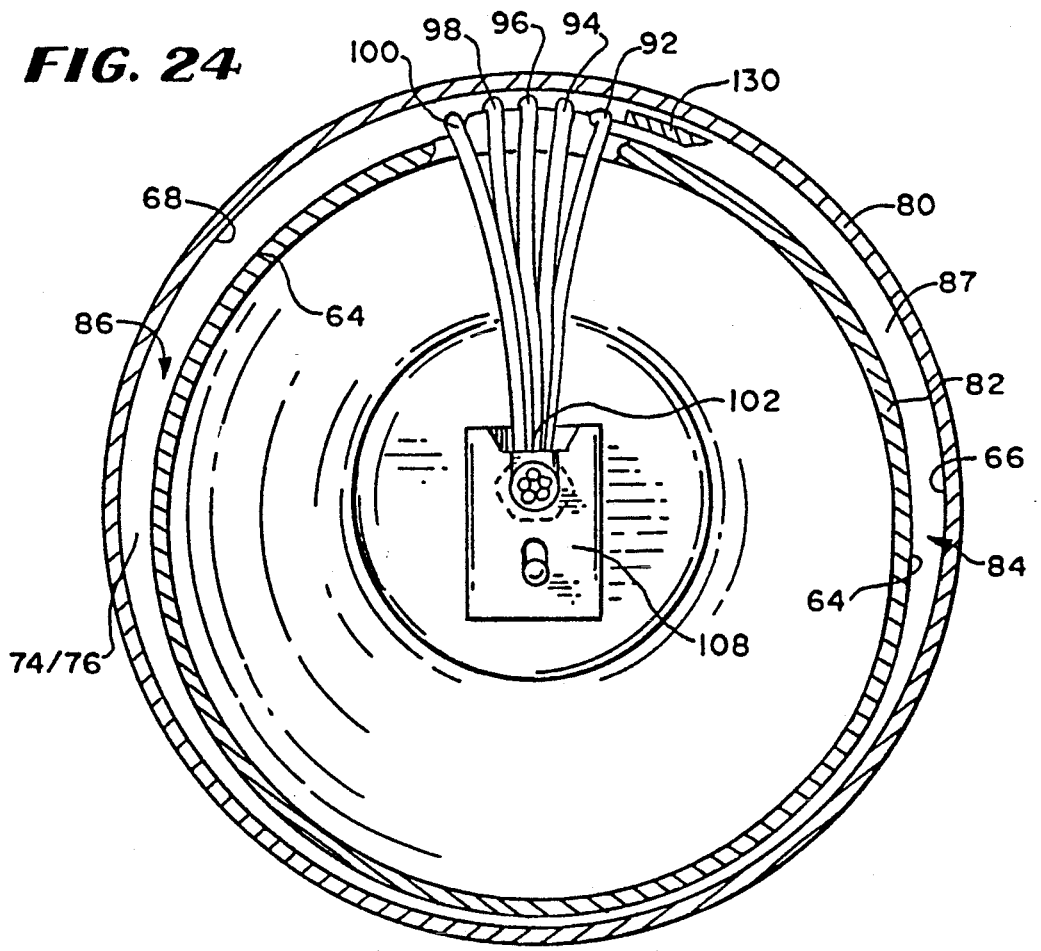
FIG. 24 is a top interior section view, taken generally along line 24—24 in FIG. 23, of the processing chamber formed by the bowl and spool assemblies of the centrifuge shown in FIG. 20.

As FIGS. 16 and 18 best show, a ramp 130 extends from the high-G wall 66 across the PRP collection region 124 in each alternative chamber assembly 74 and 76. As FIG. 24 shows from another perspective, the ramp 130 forms a tapered wedge that restricts the flow of fluid toward the PRP collection port 72. As FIG. 25 shows, the ramp 130 forms a constricted passage 131 along the low-G wall 64, along which the PRP layer extends.

In the illustrated embodiment (see FIG. 22), a hinged flap 132 extends from and overhangs a portion of the spool element 82. The flap 132 is preformed to present the desired contour of the ramp 130.

When flipped down (as FIG. 22 shows in solid lines), the flap 132 is sandwiched between the chosen chamber assembly 74/76 and the surrounding bowl element 80. The flap 132 presses against the adjacent flexible wall of the chamber assembly 74/76, which conforms to its contour to form the ramp 130 within the chamber 84.

Figure 25A:
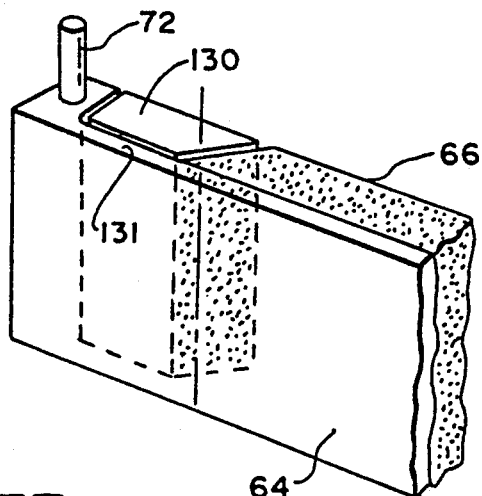
FIGS. 25A/B/C are enlarged perspective views of an interior ramp used in association with either one of the blood processing assemblies shown in FIGS. 16/17 or 18/19 for controlling flow of PRP from the chosen assembly.
Figure 25B:
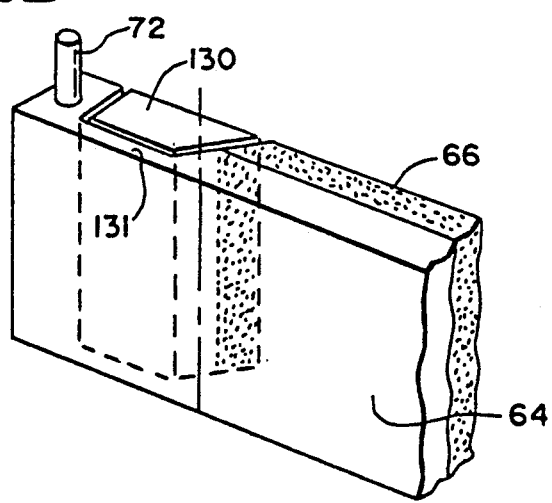
Figure 25C:
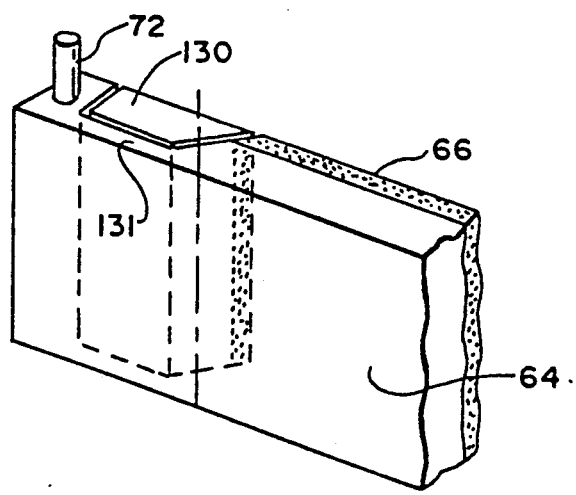
Figure 30:
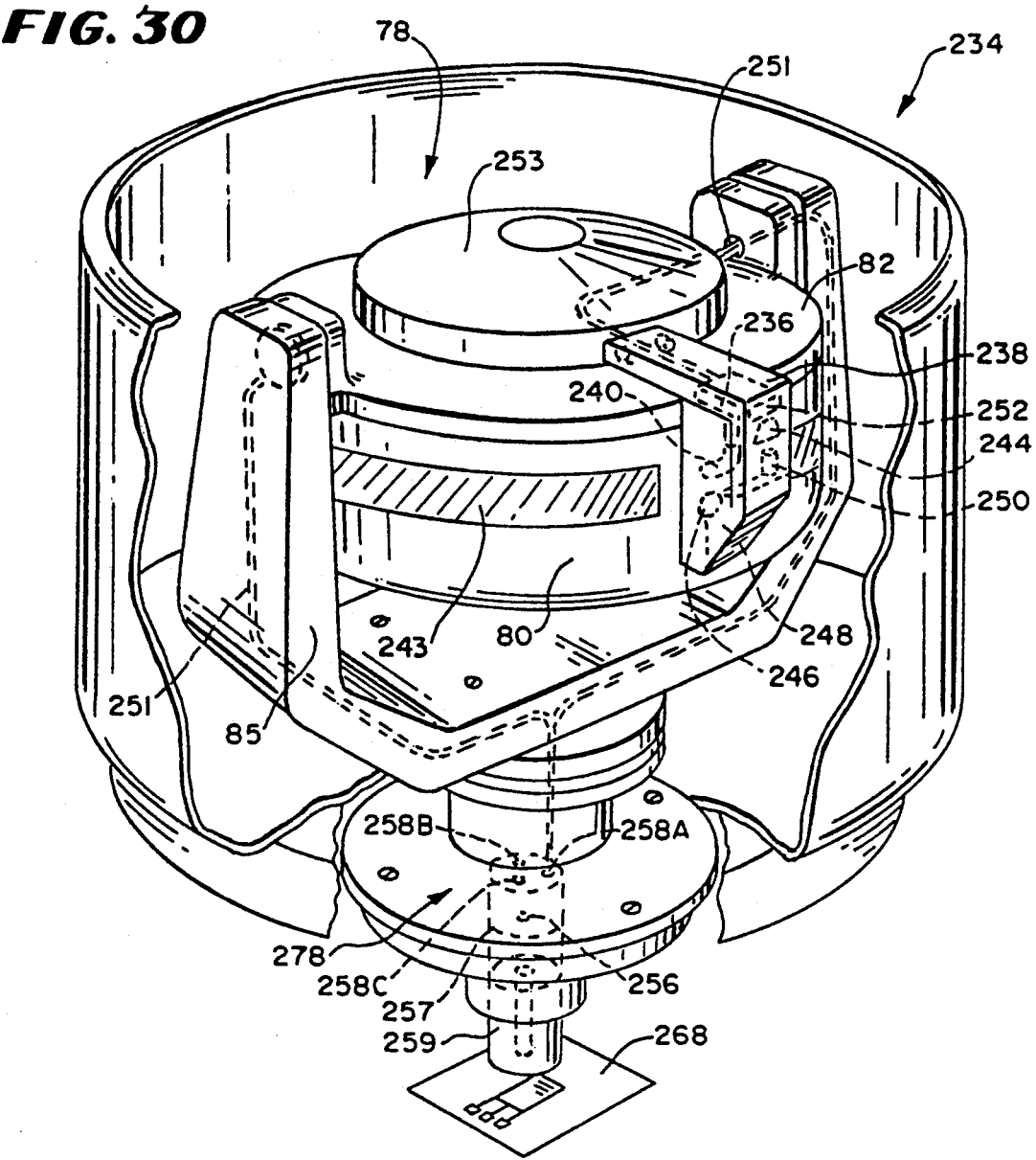
FIG. 30 is a perspective view, with portions broken away and in section, of an interface control system mounted on the rotating (one omega) portion of the centrifuge shown in FIGS. 20 and 21 and used in association with the ramp shown in FIG. 25.
Figure 31A:
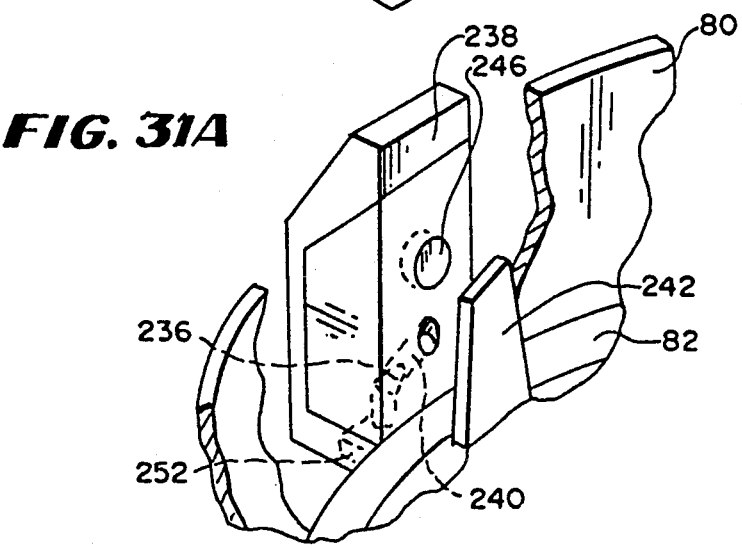
FIG. 31A is an enlarged perspective view of the rotating interface viewing head associated with the interface control system shown in FIG. 30.

As shown diagrammatically in FIGS. 25A to C, the ramp 130 diverts the fluid flow along the high-G wall 66. This flow diversion changes the orientation of the interface 26 between the RBC (shown shaded in FIGS. 25A/B/C) and the PRP (shown clear in FIGS. 25A/B/C) within the PRP collection region 124. The ramp 130 displays the interface 26 for viewing through a side wall of the chamber assembly 74/76 by an associated interface controller 234 (that FIGS. 30 and 31 show).

As will be described in greater detail later, the interface controller 234 monitors the location of the interface 26 on the ramp 130. As FIGS. 25A/B/C show, the position of the interface 26 upon the ramp 130 can be altered by controlling the relative flow rates of WB, the RBC, and the PRP through their respective ports 68/70/72. The controller 234 varies the rate at which PRP is drawn from the chamber 84 to keep the interface 26 at a prescribed location on the ramp 26 (which FIG. 25B shows), away from the constricted passage 131 that leads to the PRP collection port 72.

The ramp 130 and associated interface controller 134 keep RBC, white blood cells, and lymphocytes present in the interface 26 from entering the PRP collection port 72. The collected PRP is thereby essentially free of the other cellular components present in the interface 26.

B. The Second Stage Processing Chamber

In the embodiment of the chamber assembly shown in FIGS. 16/17, the fourth port 98 constitutes a PPP collection port 136, and the fifth port 100 constitutes a PRP inlet port 138. In the embodiment shown in FIGS. 18/19, the opposite is true: the fourth port 98 constitutes the PPP inlet port 138, and the fifth port 100 constitutes the PPP collection port 136.

In each chamber assembly 74/76, the umbilicus 102 connects the PRP collection port 72 of the first chamber 84 with the PRP inlet port 138 of the associated second chamber 86. The second chamber 86 thereby receives PRP from the first chamber 84 for further separation into PPP and PC. The umbilicus 102 conveys separated PPP from the second chamber 86 through the associated PPP collection port 136. In each assembly 74/76, the PC remains behind in the second chamber 86 for later resuspension and collection.

In the alternative embodiments shown in FIGS. 16/17 and 18/19, a fifth interior seal 140 extends between the PRP inlet port 138 and the PPP collection port 136. The fifth seal 140 includes a first region 142 that is generally parallel to the second seal 90, thereby extending across the circumferential flow path. The fifth interior seal 140 then bends in a dog-leg portion 144 away from the PRP inlet port 138 in the direction of circumferential PRP flow within the second chamber 86. The dog-leg portion 144 terminates near the longitudinal side edge of the second chamber 86 that is opposite to the longitudinal side edge formed by the second interior seal 90.

In the FIGS. 16/17 embodiment, the fifth interior seal 140, the second interior seal 90, and the lower regions of the first peripheral seal 88 together form a PPP collection passage 146 that extends first along the axis of rotation (i.e., between the second interior seal 90 and the fifth interior seal 140) and then bends in a circumferential path to open near the end of the intended PRP circumferential flow path (i.e., between the dog-leg portion 144 of the fifth seal 140 and the lower region of the peripheral seal 88). The PPP collection passage 146 receives PPP at its open end and from there channels the PPP to the PPP collection port 136.

In the FIGS. 18/19 embodiment, a similar PPP collection passage 146 is formed between the fifth interior seal 140 and the upper region of the peripheral seal 88.

In each alternative circumferential flow chamber assembly 74/76, PRP entering the second chamber 86 via the PRP inlet port 138 is caused to flow first in an axial path from the axially oriented PRP inlet port 138 alongside the axially extending fifth seal 140. The flow direction of the PRP then turns to a circumferential path away from the fifth seal 140 toward the opposite longitudinal side edge.

The centrifugal forces generated during rotation of the chamber separate the PRP into PC and PPP. The more dense PC separate out into a layer that extends along the high-G wall 66. The less dense PPP is displaced toward the low-G wall 64 for collection through the PPP collection passage 146.

The inventor has discovered that the introduction of PRP along an axial flow path parallel to the axis of rotation into a circumferential flow path about the axis of rotation creates a non-turbulent vortex region 148, called a Taylor column, at the outlet of the PRP inlet port 138, as FIG. 26 shows.

The vortex region 148 circulates about an axis that is aligned with the axis of the PRP inlet port 138. The vortex region 148 stretches from the outlet of the port 138 longitudinally across the circumferential flow path of the chamber 86. As FIG. 26 shows, the vortex region 148 circulates the PRP about its axis and directs it into the desired circumferential flow path within the chamber 86.

Within the vortex region 148, axial flow velocity decreases in a generally linear fashion across the circumferential flow path of the chamber 86. This occurs as the axial flow of fluid entering the chamber 86 perfuses uniformly into a circumferential flow entering the separation zone.

A similar vortex region 148 forms at the opposite longitudinal end of the second chamber 86 at the entrance to the PPP collection passage 146, as FIG. 26 also shows.

The vortex region 148 created at the outlet of the PRP inlet port 138 uniformly disperses PRP in the desired circumferential flow path into the centrifugal field. This maximizes the exposure of the entering PRP to the effects of the centrifugal field across the effective surface area of the second chamber 86. Maximum possible separation of PC from the entering PRP results.

It should be noted that similar vortex region 148 flow conditions are formed in the first chamber 84 as well, where fluid either enters or leaves the established circumferential flow path through an axial flow path. As FIG. 26 shows, a vortex region 148 condition thereby forms at the entrance of the WB inlet passage 122. Another vortex region 148 condition forms at the opposite longitudinal end at the entrance of the RBC collection passage 126.

In both alternative chamber assemblies 74/76 (as FIGS. 17 and 19 show), the low-G wall 64 preferably tapers into the second chamber 86 in the direction of circumferential PRP flow. The taper proceeds from the second interior seal 90 toward the opposite longitudinal end of the second chamber 86.

Also in both alternative chamber assemblies 74/76 (as FIGS. 16 and 18 show), the circumferential leg of the associated PPP collection passage 146 is tapered. Due to the taper, the leg presents a greater cross section where it opens into the second chamber than it does where it joins the axial portion of the PPP collection passage 146. In the illustrated and preferred embodiment, the leg tapers from a width of about ¼ inch to ⅛ inch.

As with the taper of the dog leg portion 120, the taper of the circumferential leg of the PPP collection passage 146 is preferably gauged relative to the taper of the low-G wall 64 to keep the cross sectional area of the PPP collection passage 146 substantially constant. This keeps fluid resistance within the passage 146 relatively constant. The taper of the circumferential leg of PPP collection passage 146 also facilitates the removal of air from the passage 146 during priming.

The dimensions of the various regions created in the processing chamber can of course vary according to the processing objectives. Table 2 shows the various dimensions of a representative embodiment of a processing chamber of the type shown in FIGS. 16/17 or 18/19. Dimensions A through F referenced in Table 2 are identified for their respective chamber assemblies in FIGS. 16 and 18.

TABLE 2

Overall length (A): 19¼ inches
Overall height (B): 2 13/16 inches
First Stage Processing Chamber
Length (C): 10⅛ inches
Width (D): 2⅞ inches
Maximum Radial Depth in Use: 4 mm
Second Stage Processing Chamber
Length (E): 8 13/16 inches
Width (F): 2⅞ inches
Maximum Radial Depth in Use: 4 mm
Port Spacing
(center line to center line): ⅝ inch

Figure 27:
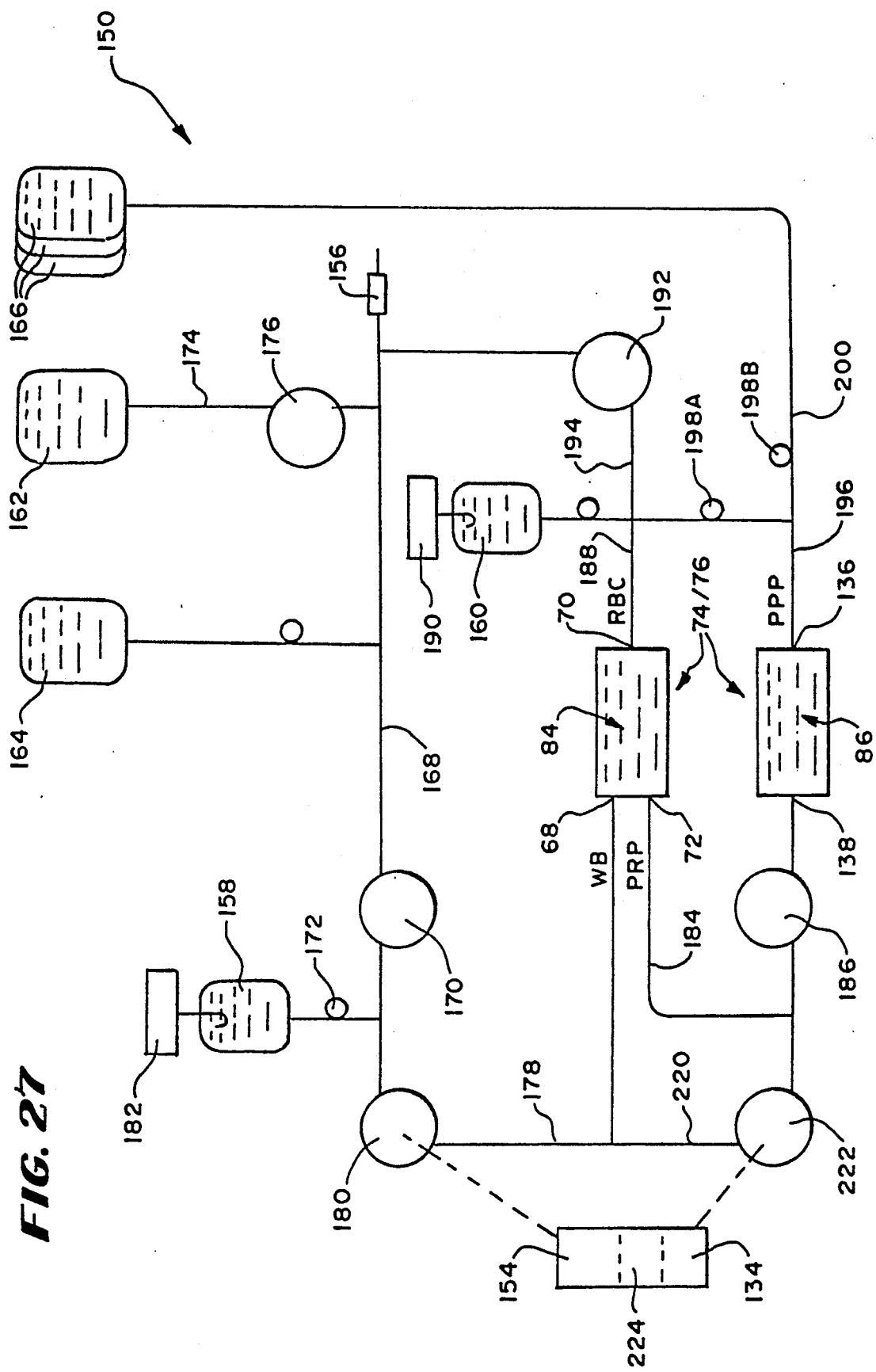
FIG. 27 is a single needle platelet collection system that can be used in association with either one of the blood processing assemblies shown in FIGS. 16/17 or 18/19.
Figure 28:
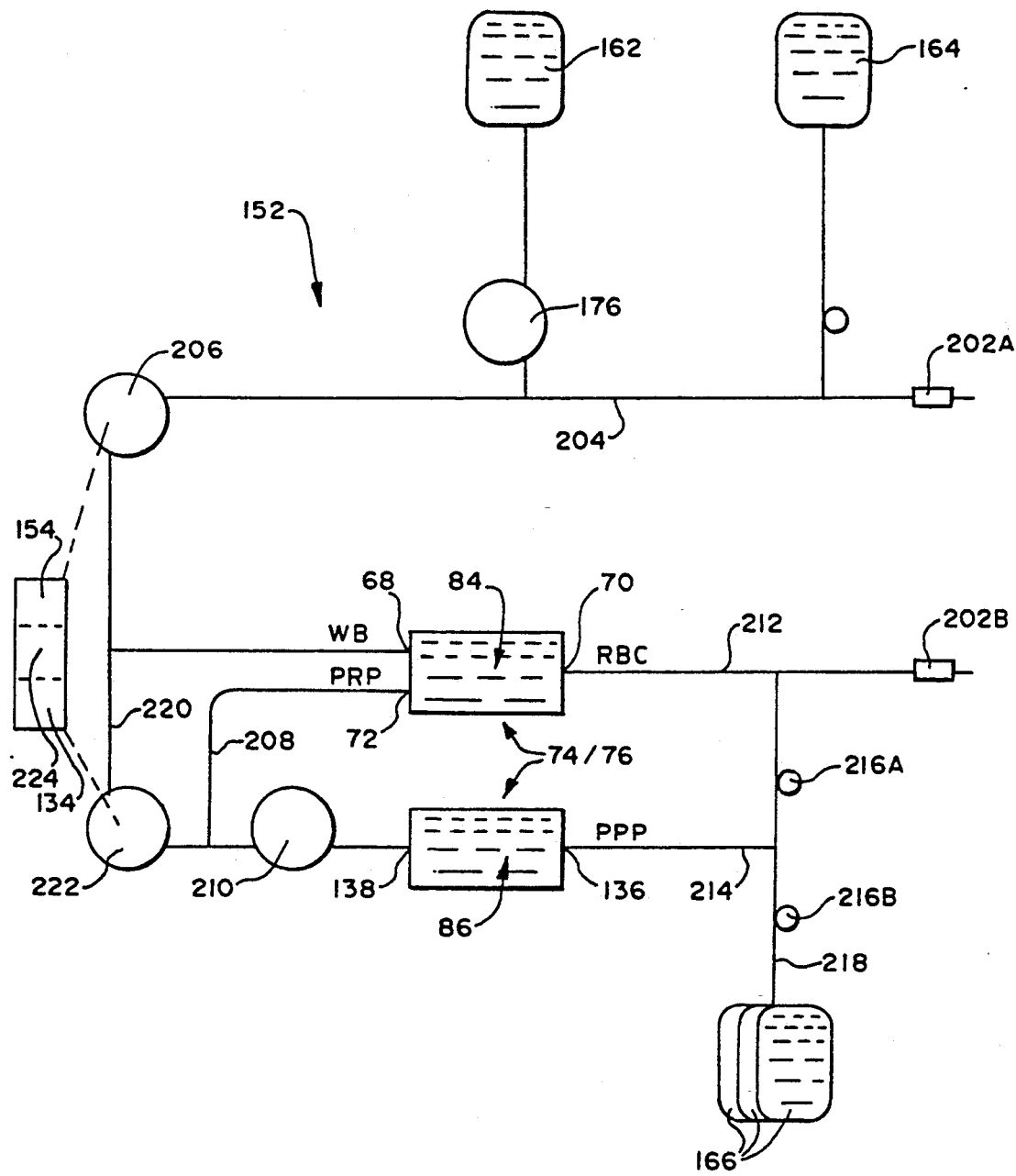
FIG. 28 is a double needle platelet collection system that can be used in association with either one of the blood processing assemblies shown in FIGS. 16/17 or 18/19.

III. Systems Using the Enhanced Yield Circumferential Flow Chamber for Platelet Separation and Collection The two stage circumferential flow chambers shown in either FIGS. 16/17 or FIGS. 18/19 can be used to do continuous platelet collection. The chambers can be used in associated either with a system 150 that employs one phlebotomy needle (as FIG. 27 shows) or with a system 152 that employs two phlebotomy needles (as FIG. 28 shows). In each system 150 and 152, an associated processing controller 154 automates the collection procedure to the fullest extent possible.

A. Single Needle Enhanced Yield Platelet Collection System

The platelet collection system 150 shown in FIG. 27 employs one, single lumen phlebotomy needle 156. FIG. 21 generally depicts this single needle system 150 when mounted for use on the centrifuge 78.

The processing controller 154 operates the single needle system 150 in a draw cycle and a return cycle.

During the draw cycle, the controller 154 supplies the donor's WB through the needle 156 to a chosen one of the processing chamber assemblies 74/76. There, the WB is centrifugally separated into RBC, PC, and PPP.

During the return cycle, the controller 154 returns RBC and PPP to the donor through the needle 156, while separation within the chosen processing chamber assembly 74/76 continues without interruption. The harvested PC is retained for long term storage. If desired, all or some PPP can be retained for storage, too.

The system 150 includes a draw reservoir 158, which pools a quantity of the donor's WB during the draw cycle. The system 150 also includes a return reservoir 160, where a quantity of RBC collect for periodic return to the donor during the return cycle.

Processing containers associated with the system 150 include a container 162 that holds anticoagulant for use during the procedure and a container 164 that holds saline solution for use in priming and purging air from the system 150 before the procedure. The system further includes collection containers 166 for receiving PC (and optionally PPP) for storage.

When the controller 154 operates the system 150 in the draw cycle, a first branch 168 directs WB from needle 156 to the draw reservoir 158, in association with the draw pumping station 170 and a clamp 172. An auxiliary branch 174 delivers anticoagulant to the WB flow in association with an anticoagulant pumping station 176.

A second branch 178 conveys the WB from the draw reservoir 158 to the WB inlet port 68 of the chosen processing chamber assembly 74/76, in association with the WB inlet pumping station 180. The draw pumping station 170 operates at a higher flow rate (at, for example, 100 ml/min) than the WB inlet pumping station 180, which operates continuously (at, for example, 50 ml/min).

The processing controller 154 includes a first scale 182 that monitors the weight volume of WB collected in the draw reservoir 158. The first scale 182 intermittently operates the draw pumping station 170 to maintain a desired weight volume of WB in the draw reservoir 158.

Once the desired volume of WB is present in the draw reservoir 158, the WB inlet pumping station 180 operates to continuously convey WB into the chosen processing chamber assembly 74/76.

The draw pumping station 170 continues to operate periodically during the draw cycle in response to the scale 182 to maintain the desired weight volume of WB in the draw reservoir 158.

The WB enters the first stage chamber 84, where it is separated into RBC and PRP. This separation process has already been described.

A third branch 184, in association with the plasma pumping station 186, draws the PRP from the PRP collection port of the first processing chamber 84. The third branch 184 conveys the PRP to the PRP inlet port 138 of the second processing chamber 86. There, the PRP is further separated into PC and PPP. This separation process has already been described.

As will be described in greater detail later, the processing controller 154 monitors the location of the interface on the ramp 130 via the interface controller 134. The controller 154 operates the plasma pumping station 186 to keep the maximum rate of the variable plasma pumping station 186 (for example, 25 ml/min) less than the WB inlet pumping station 180.

A fourth branch 188 conveys the RBC from the RBC collection port 70 of the first stage processing chamber 84. The fourth branch 188 leads to the return reservoir 160.

The processing controller 154 includes a second scale 190 that monitors the weight volume of RBC in the return reservoir 160. When a preselected weight volume exists, the controller 154 shifts the operation of the system 150 from its draw cycle to its return cycle.

In the return cycle, the controller 154 stops the draw pumping station 170 and starts a return pumping station 192. A fifth branch 194 associated with the return pumping station 192 conveys RBC from the return reservoir 160 to the needle 156.

Meanwhile, while in the return cycle, the controller 154 keeps the WB inlet pumping station 180 and plasma pumping station 186 in operation to continuously process the WB pooled in the draw reservoir 158 through the first processing chamber 84.

During both draw and return cycles, PRP enters the PRP inlet port 138 of the second stage processing chamber 86. The PPP exits the PPP collection port 136 of the second stage processing chamber through a sixth branch 196 and into the return reservoir 160, joining the RBC there pooled.

Alternatively, by closing the clamp 198A and opening the clamp 198B, the PPP can be conveyed through a seventh branch 200 to one or more collection containers 166.

After a procedure, the PC collected within the second processing compartment 86 is transferred via the seventh branch 200 to one or more collection containers 166 for storage.

B. Double Needle Platelet Collection System

The platelet collection system 152 shown in FIG. 28 employs two single lumen phlebotomy needles 202A and 202B to obtain generally the same processing results as the single needle system 150 shown in FIG. 27. Elements common to both systems 150 and 152 are assigned the same reference numeral.

The associated processing controller 154 operates the system 152 in a continuous cycle, during which the donor's WB is continuously supplied through the needle 202A to the chosen processing chamber assembly 74/76 for separation into RBC, PC, and PPP, while RBC and PPP are continuously returned to the donor through the needle 202B.

As in the single needle system 150, the harvested PC is retained for long term storage. If desired, all or some PPP can be diverted from the donor for storage.

As in the single needle system 150, the processing containers associated with the double needle system 152 include a container 162 that holds anticoagulant and a container 164 that holds saline solution for use in priming and purging air from the system 152.

The system 152 also includes similar collection containers 166 for receiving PC (and optionally PPP) for storage.

Under the control of the controller 154, a first branch 204 directs WB from the needle 202A to the WB inlet port 68 of the first stage processing chamber 84, in association with the WB inlet pumping station 206, which operates continuously at, for example, 50 ml/min. An auxiliary branch 174 delivers anticoagulant to the WB flow in association with an anticoagulant pumping station 176.

The WB enters and fills the first processing chamber 84 in the manner previously described, where centrifugal forces generated during rotation of the chosen chamber assembly 74/76 separate the WB into RBC and PRP.

A second branch 208, in association with the plasma pumping station 210, draws the PRP layer out the PRP collection port 72 of the first stage processing chamber 84, conveying the PRP to the PRP inlet port 138 of the second stage processing chamber 86, where it undergoes further separation into PC and PPP.

The processing controller 154 monitors the location of the interface on the ramp 130 and varies the speed of the plasma pumping station 210 (using the interface controller 134, to be described later in greater detail) to keep the interface 26 at a prescribed location on the ramp 130. As before described, the controller 154 keeps the maximum rate of the variable plasma pumping station 210 (for example, 25 ml/min) less than the WB inlet pumping station 206.

A third branch 212 conveys the RBC from the RBC collection port 70 of the first stage processing chamber 84. The third branch 212 leads to the needle 202B.

The PPP exits the PPP collection port 136 of the second stage processing chamber 86 through a fourth branch 214, joining the third branch 212 (carrying RBC) leading to the needle 202B. Alternatively, by closing the clamp 216A and opening the clamp 216B, the PPP can be conveyed through a fifth branch 218 to one or more collection containers 166.

After a procedure, the PC collected within the second processing compartment 86 is transferred via the fifth branch 218 to one or more collection containers 166 for storage.

C. Enhancing Platelet Separation by Plasma Recirculation

Both single and double needle systems 150 and 152 (shown in FIGS. 27 and 28 respectively) include a recirculation branch 220 and an associated recirculation pumping station 222. The processing controller 154 has a recirculation control system 224 that operates the pumping station 222 to convey a portion of the PRP exiting the PRP collection port 72 of the first processing compartment 84 for remixing with the WB entering the WB inlet port 68 of the first processing compartment 84.

The control system 224 can control the recirculation of PRP in different ways.

Figure 29:
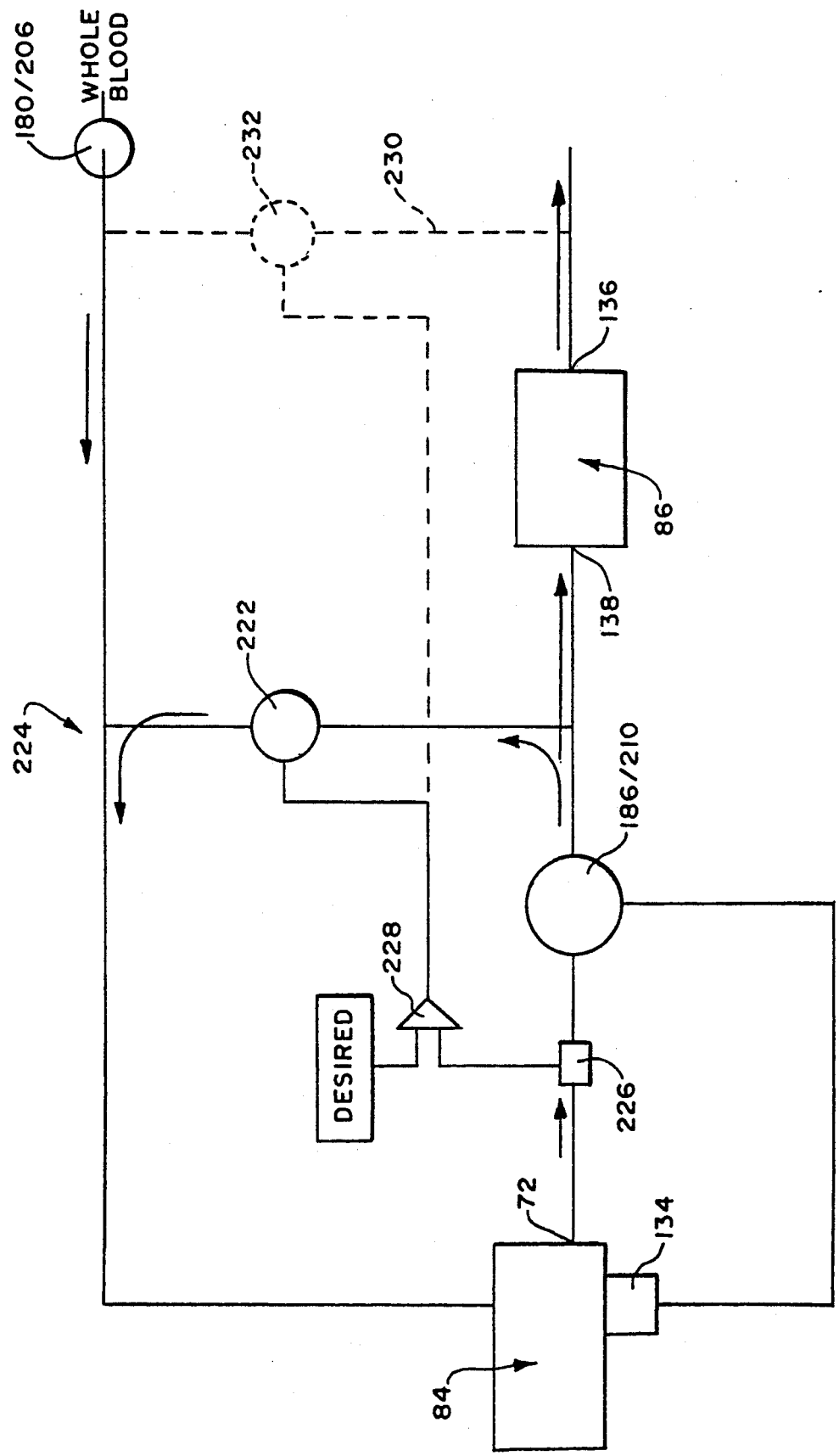
FIG. 29 is a plasma recirculation control system that can be used in association with either one of the blood processing systems shown in FIGS. 27 or 28.

As FIG. 29 shows, the recirculation control system 224 includes a sensor 226 that senses the flow rate at which PRP exits the first processing compartment 84, under the control of pumping station 186 (for the single need system 150) or pumping station 210 (for the double needle system 152). As will be described in greater detail, this flow rate is itself controlled by the interface controller 134.

The recirculation control system 224 employs a comparator 228 to compare the sensed PRP flow rate to an established desired flow rate. If the sensed rate is less than the desired flow rate, the comparator 228 sends a signal to increase rate at which the recirculation pumping station 222 operates. And, if the sensed rate is more than the desired flow rate, the comparator 228 sends a signal to decrease the rate at which the recirculation pumping station 222 operates. In this way, the comparator 228 maintains the PRP flow rate at the desired rate.

The desired PRP output rate is preselected to create within the first compartment 84 the processing conditions which maximize the concentration of platelets in the PRP stream.

The desired rate of recirculation is based upon the radial flow rate of plasma desired in the region where PRP is collected.

According to another aspect of the invention, the pumping rate of the recirculation pump 222 is maintained as a percentage ($\%_{RE}$) of the pumping rate of the whole blood inlet pump 180/206, governed as follows:

$$\%_{RE} = K * Hct - 100$$

where:

Hct is the hematocrit of the donor's whole blood, measured before donation, and

K is a dilution factor that takes into account the volume of anticoagulant and other dilution fluids (like saline) that are added to the donor's whole blood before separation.

According to this aspect of the invention, the pumping rate of the recirculation pump 222 is maintained at the predetermined percentage ($\%_{RE}$) of the pumping rate of the whole blood inlet pump 180/206 to maintain a surface hematocrit of about 30% to 35% in the entry region $R_e$. The preferred surface hematocrit in the entry region $R_e$ is believed to be about 32%.

Keeping the surface hematocrit in the entry region $R_e$ in the desired range provides optimal separation of RBC from PRP, thereby optimizing the radial flow of plasma in this region. If the surface hematocrit exceeds the predetermined range, radial plasma flow in the entry region $R_e$ decreases. If the surface hematocrit falls below the predetermined range, the radial flow of PRP increases enough to sweep small RBC's and white blood cells into the PRP.

The value of the dilution factor K can vary according to operating conditions. The inventor has determined that K=2.8, when ACD anticoagulant is added to constitute about 9% of the entry whole blood volume, and a saline dilution fluid is added in an amount representing about 4% of donor body volume (i.e., 200 ml saline for 5000 ml in body volume).

In an alternate arrangement (shown in phantom lines in FIG. 29), the recirculation control system 224 recirculates PPP, instead of PRP, based upon $\%_{RE}$, as determined above.

In this arrangement, the system 224 uses a recirculation branch 230 and associated pumping station 232 located downstream of the second processing compartment 86. The comparator controls the pumping station 232 in one of the same manners just described to mix PPP exiting the second compartment 86 with the incoming WB entering the first compartment 84.

By mixing PRP (or PPP) with the WB entering the first processing compartment 84 to control surface hematocrit in the entry region $R_e$, the velocity at which red blood cells settle toward the high-G wall 66 in response to centrifugal force increases. This, in turn, increases the radial velocity at which plasma is displaced through the interface 26 toward the low-G wall 64. The increased plasma velocities through the interface 26 elute platelets from the interface 26. As a result, fewer platelets settle on the interface 26.

EXAMPLE 2

A study evaluated a two stage separation chamber 74 like that shown in FIG. 16 in a platelet collection procedure on a healthy human donor. The chamber 74 was part of a double needle system 152, like that shown in 28. The system 152 recirculated PRP in the manner shown in FIG. 28 to obtain a hematocrit of 32.1% in the PRP collection region 124 of the chamber 74.

In this study, the low-G wall 64 of the first stage chamber 84 was not tapered in the direction of circumferential flow from the PRP collection region 124. The low-G wall 64 was isoradial along the circumferential flow path in the first stage chamber 84, except for the presence of a RBC barrier 128, which stepped into the chamber across the RBC collection passage, as shown in FIG. 17. The low-G wall 64 was isoradial along the entire circumferential flow path of the second chamber 86.

Figure 35A:
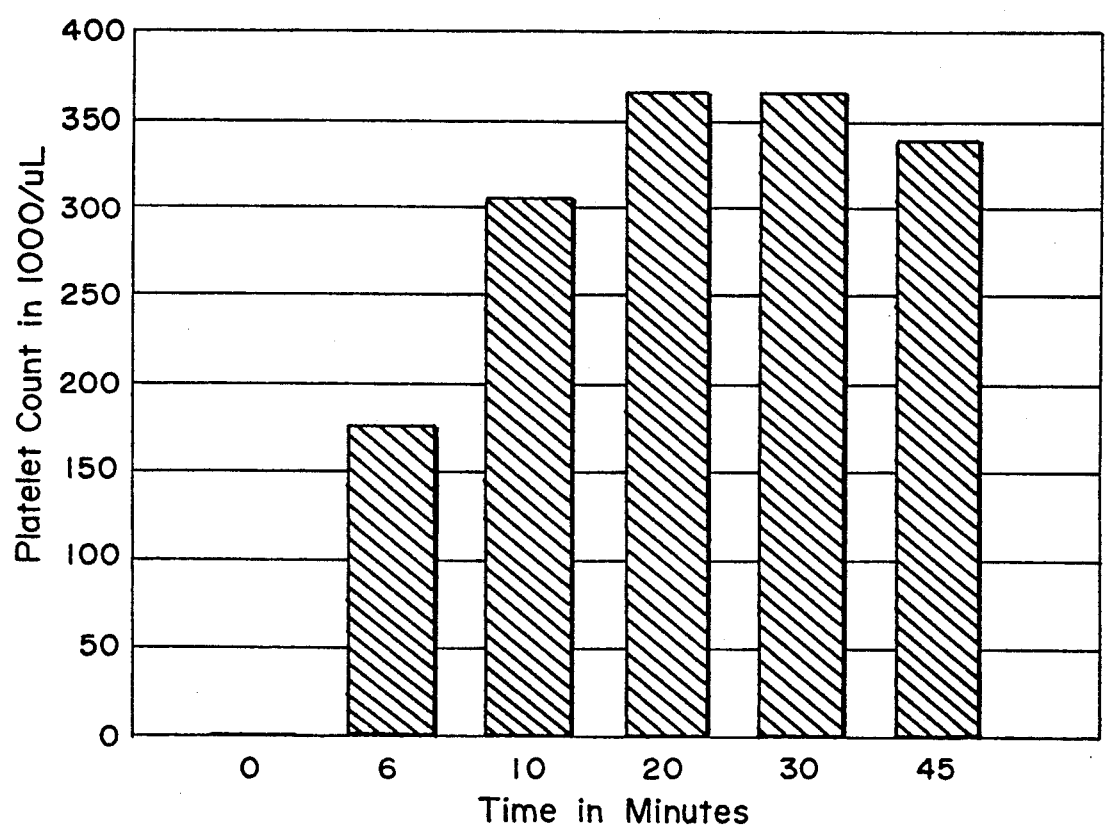
FIGS. 35A/B show, respectively, the platelet counts and mean platelet volumes sampled during a 45 minute procedure using a separation chamber that embodies the features of the invention.

FIG. 35A shows the platelet count sampled in the PRP (in 1000 platelets per uL) over time during the 45 minute procedure. As there shown, after a run time of 6 minutes, the platelet count was 173; after 10 minutes, the platelet count was 304; and after 20 minutes, the platelet count stabilized at 363.

Figure 35B:
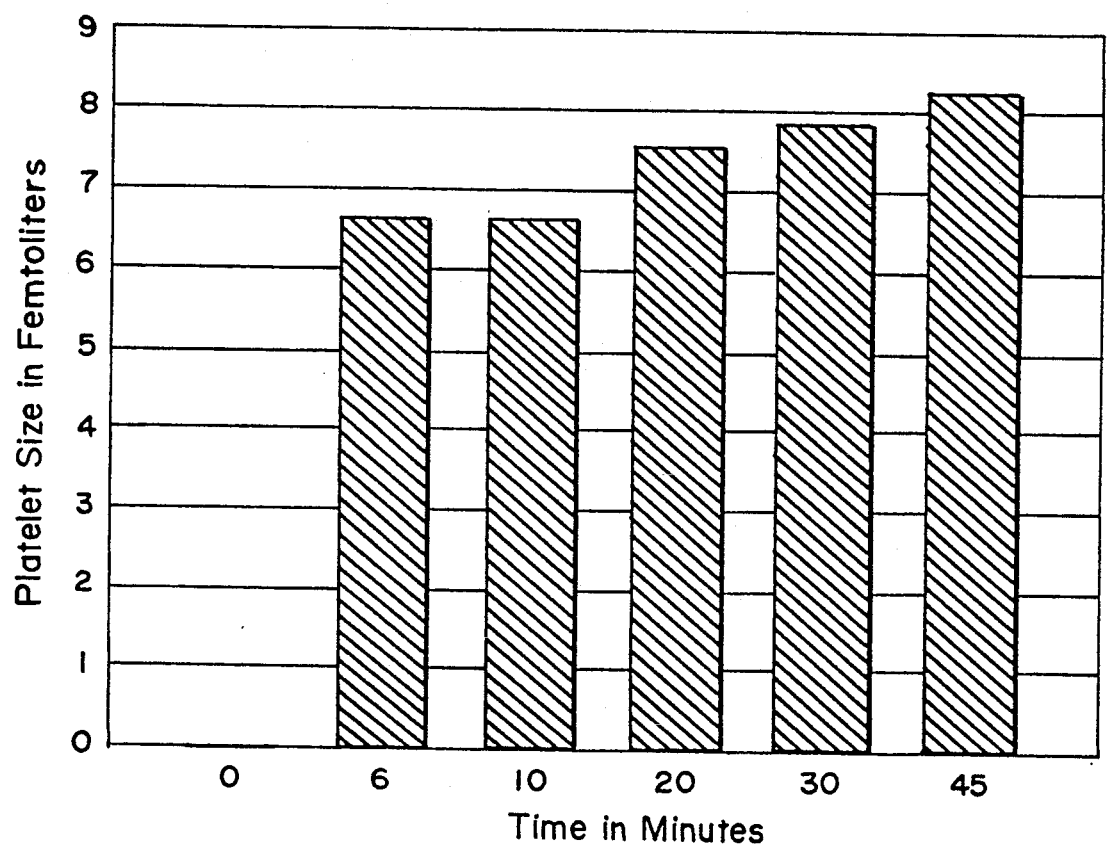

FIG. 35B shows the physical size of the platelets collected in the PRP in terms of mean platelet volume (in femtoliters) sampled during the procedure. As there shown, after a run time of 6 minutes, the mean platelet size was 6.6; after 20 minutes, the mean platelet size rose to 7.5; and at the end of the procedure, the mean platelet size was 8.2. A size distribution study of the PC collected showed that about 3% of the platelets collected were larger than 30 femtoliters (i.e., were very large platelets).

The platelet transfer efficiency in the first stage chamber 84 (i.e., the percentage of available platelets entering the first stage chamber 84 that were ultimately collected in the PRP) was 93.8%. In other words, the first stage chamber 84 failed to collect only 6.2% of the available platelets in the first stage chamber 84.

The platelet transfer efficiency in the second stage chamber 86 (i.e., the percentage of available platelets in the PRP entering the second stage chamber 86 that were ultimately collected as PC) was 99%. In other words, the second stage chamber 86 failed to collect only 1% of the platelets present in the PRP in the second stage chamber 86.

The overall platelet collection efficiency of the chamber was about 81%, meaning that about 81% of the platelets in the whole blood processed were ultimately collected. This is a significantly higher amount than conventional processing can provide. In comparison, the comparable overall platelet collection efficiency for two stage CS-3000 ® Centrifuge chamber is about 50%.

This study demonstrates the increased separation efficiencies that result from chambers and systems that embody features of the invention.

Example 3

Another study evaluated a two stage separation chamber like that in Example 2 in a platelet collection procedure on a healthy human donor. As in Example 2, a double needle system was used. The system recirculated PRP to obtain an inlet hematocrit of 34.3%.

In this study, the low-G wall 64 of the first stage chamber 84 was tapered in the direction of circumferential flow from the PRP collection region 124, like that shown in FIG. 17. The low-G wall 64 also included RBC barrier 128 like that shown in FIG. 17. The low-G wall 64 was also tapered along the entire circumferential flow path of the second chamber 86.

Figure 36A:
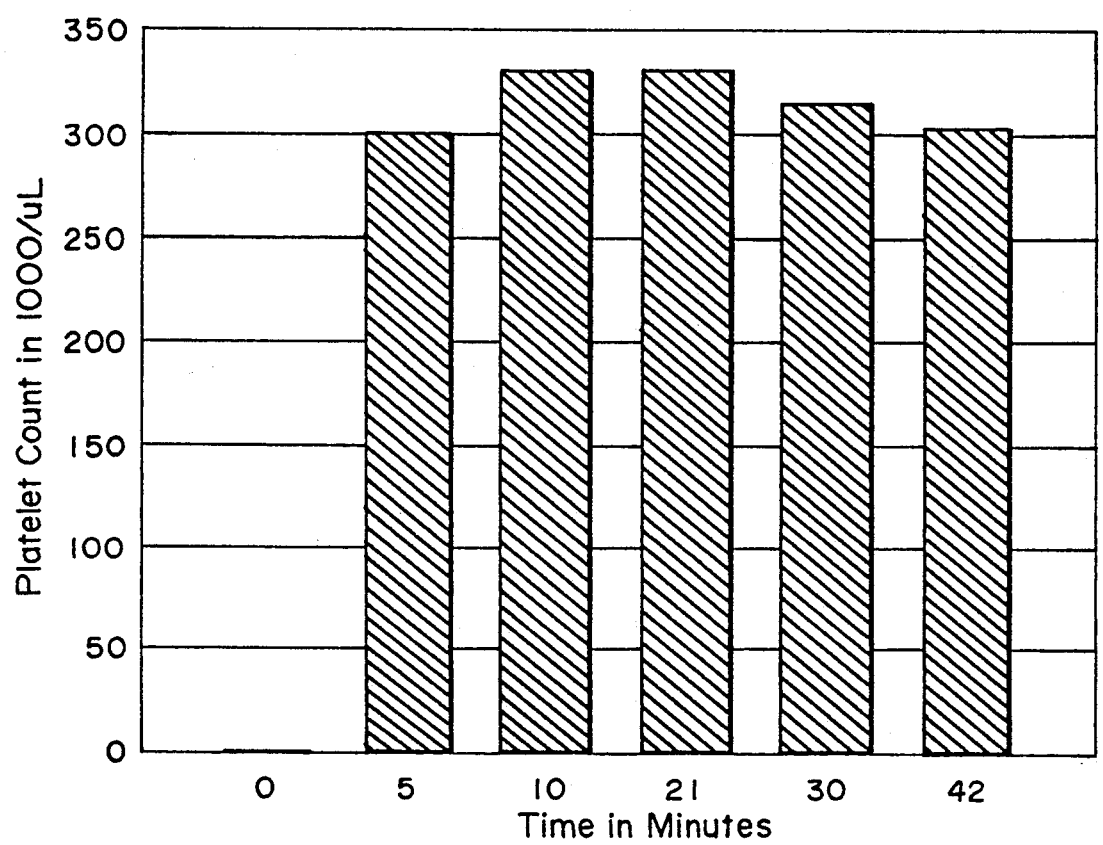
FIGS. 36A/B show, respectively, the platelet counts and mean platelet volumes sampled during a 45 minute procedure using another separation chamber than embodies the features of the invention.

FIG. 36A shows the platelet count sampled in the PRP (in 1000 platelets per uL) over time during the 45 minute procedure. As there shown, a platelet count of 300 was achieved in the first 5 minutes of the procedure. The platelet count peaked at 331 after 21 minutes. At the end of the procedure, the platelet count was 302.

Figure 36B:
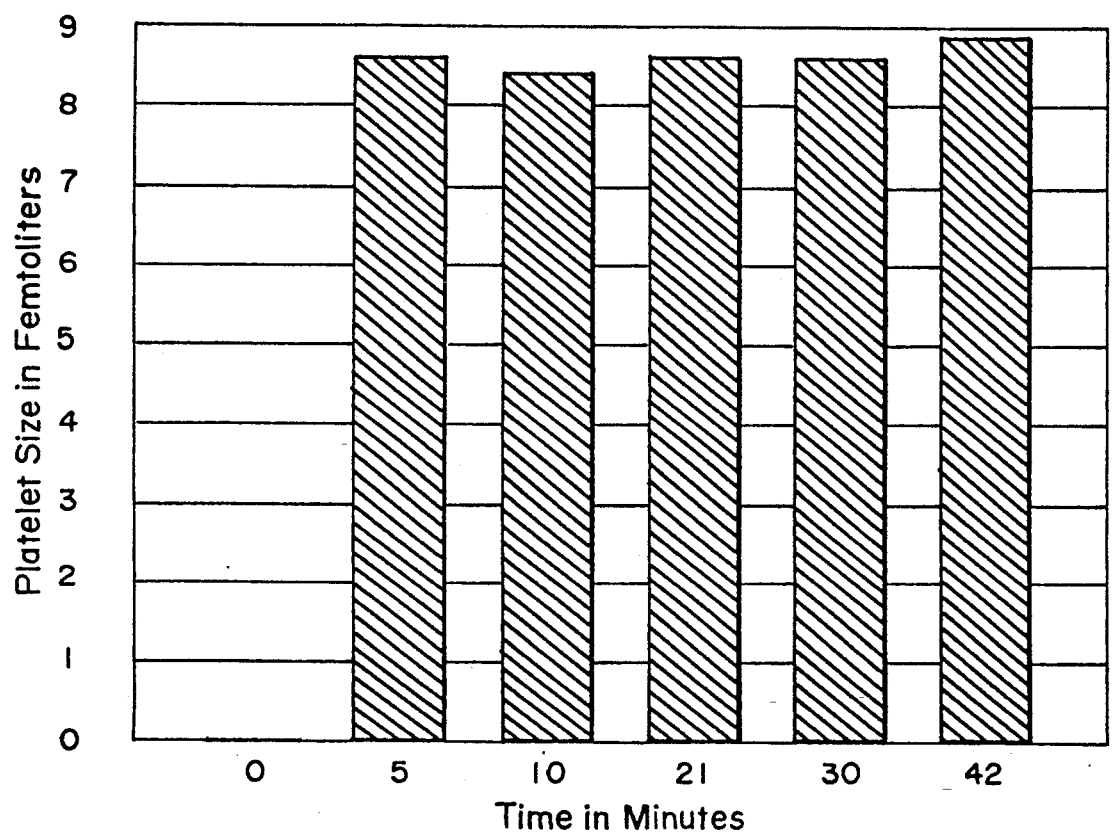

FIG. 36B shows the physical size of the platelets collected in the PRP in terms of mean platelet volume (in femtoliters) sampled during the procedure. As there shown, after a run time of only 5 minutes, the mean platelet size was 8.6, where it virtually remained throughout the rest of the procedure. A size distribution study of the PC collected showed that about 8.5% of the platelets collected were larger than 30 femtoliters.

The second study also experienced greater collection efficiencies.

The platelet transfer efficiency in the first stage chamber 84 (i.e., the percentage of available platelets that were ultimately collected in the PRP) was 99.2%. In other words, the first stage chamber 84 failed to collect less than 1% of the available platelets.

The platelet transfer efficiency in the second stage chamber 86 (i.e., the percentage of available platelets in the PRP that were ultimately collected as PC) was 99.7%. In other words, the second stage chamber 86 collected nearly all the platelets present in the PRP.

The overall platelet collection efficiency of the chamber was 85.3%.

This study further demonstrates the enhanced separation efficiencies that the inventions can provide.

This study also shows the effect that the tapered low-G wall has in freeing greater number of platelets into the PRP stream. The effect is virtually immediate. After only 5 minutes in the second study, the platelet count was comparable to that encountered after 10 minutes in the first study.

This study also demonstrates the effect that the tapered low-G wall has in freeing larger platelets into the PRP stream. The effect, too, is virtually immediate. After the first 5 minutes of the procedure, the mean platelet size was comparable to that encountered after 30 minutes in the second study, which means that the larger platelets were already being collected. There were nearly 3 times more platelets of very large physical size (i.e., over 30 femtoliters) collected in the second study than in the first study.

IV. Interface Control Systems for the Enhanced Yield Circumferential Flow Chambers FIGS. 30 to 34 show the details of an alternative interface control system 234, which can be used in association with either the single or double needle systems 150 or 152 previously described.

The interface control system 234 mounts the element that actually views the interface on a rotating element of the centrifuge. The system 234 relies upon a time pulse signal to determine the location of the interface.

As FIGS. 30 and 31 A/B show, the interface control system 234 includes a light source 236 mounted on the yoke 85 of the centrifuge 78. The source 236 emits light that is absorbed by RBC. The control system 234 also includes a light detector 244 mounted next to the light source 236 on the yoke 85.

As FIG. 30 shows, a viewing head 238 carries both the light source 236 and the light detector 244 for rotation on the yoke 85. As previously described, the yoke 85 rotates at a one omega speed, carrying the viewing head 238 with it. At the same time, the spool and bowl assemblies 80 and 82 carried by the yoke 85 rotate at a two omega speed.

In the illustrated and preferred embodiment, the viewing head 238 also serves as a counterweight for the umbilicus holder 106 that the yoke 85 also carries (also see FIGS. 20 and 21).

In the illustrated and preferred embodiment, the light source 236 includes a red light emitting diode. Of course, other colors, like green, could be used. In this arrangement, the light detector 244 comprises a PIN diode detector.

Figure 31B:
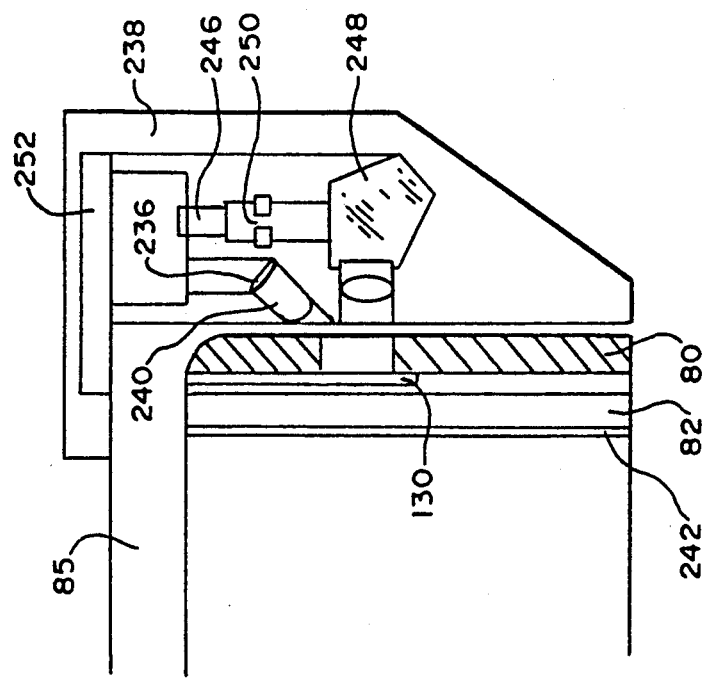
FIG. 31B is a side section view showing the interior of rotating interface viewing head shown in FIG. 31A.

An optical pathway 240 directs light from the source diode 236 out onto the rotating bowl assembly 80 (see FIG. 31B). In the illustrated embodiment, the bowl assembly 80 is transparent to the light emitted by the source diode 236 only in the region where the bowl assembly 80 overlies the interface ramp 130.

The remainder of the bowl assembly 80 that lies in the path of the viewing head 238 carries a light reflecting material 243. This differentiates the reflective properties of the interface region of the bowl assembly 80 from those of the remainder of the bowl assembly 80. The material 243 could be light absorbing and serve the same purpose.

Alternatively, the source diode 236 could be gated on and off with the arrival and passage of the interface region of the bowl assembly 80 relative to its line of sight.

The interface ramp 130 carried by the spool assembly 82 is made of a light transmissive material. The light from the source diode 236 will thus pass through the transparent region of the bowl assembly 80 and the ramp 130 every time the rotating bowl assembly 80 and viewing head 238 align.

The spool assembly 82 also carries a light reflective material 242 on its exterior surface behind the interface ramp 130 (see FIG. 36). The material 242 reflects incoming light received from the source diode 236 out through the transparent region of the bowl assembly 80. The intensity of the reflected light represents the amount of light from the source diode 236 that is not absorbed by the RBC portion of the interface region.

The light detector 244 carried in the viewing head 238 receives the reflected light through an optical pathway. In the illustrated embodiment (see FIG. 31B), the optical pathway includes a lens 246, a penta prism 248, and an aperture 250.

In the illustrated embodiment, the lens 246 is about 9 mm in diameter, with the focal length of about 9 mm. In this arrangement, the lens 246 forms a real image with a magnification of about three. Alternatively, the real image could be made smaller to provide a better depth of field.

The aperture 250 is preferably small (about 0.75 mm in diameter) to allow only a small portion of the real image to reach the detector 244. The preferred viewing field of the detector 244 is therefore small, i.e., preferably on the order of about 0.25 mm in diameter.

The system 234 further includes a data link 278 for transmitting light intensity signals from the rotating viewing head 268 to an interface control circuit 270 on the stationary frame of the centrifuge. In the illustrated embodiment, the data link is optical in nature. Alternatively, slip rings could be used to transmit the light intensity signals as voltage or current signals.

The optical data link 278 includes a second light source 254. The second light source 254 is carried within the confines of a hollow light conduction passage 256 within the one omega drive shaft 257.

The optical data link 278 further includes a second light detector 268. The second detector 268 is carried on the non-rotating (i.e., zero omega) base of the centrifuge below the hollow one omega drive shaft 257. Light from the second light source 254 passes through the passage 256 and a collimating sleeve 259 to fall upon the second detector 268. Like the first detector 244, the second detector 268 can comprise a PIN diode detector.

The second light source 254 comprises at least one red light emitting diode carried within the passage 256 of the one omega shaft 257. Of course, other colors, like green, could be used.

In the illustrated embodiment (see FIG. 30), the second light source 254 includes three light emitting diodes 258 A/B/C arranged at 120 degree circumferentially spaced intervals within the passage 256. This arrangement minimizes interference due to misalignment between the second light source 254 and the second detector 268. In an alternative arrangement, the light intensity signal from the second detector 268 can be electronically filtered to eliminate interference signals caused by misalignment.

The optical data link 278 also includes an intensity control circuit 252 carried onboard the viewing head 238. The intensity control circuit 252 adjusts the input to the source diode 236 so that the intensity of light hitting the detector 244 remains constant.

The intensity control circuit 252 also connects the second light source 254 in series to the first mentioned light source 236. Thus, as the intensity control circuit 252 adjust the input to the first light source 236, it will also instantaneously adjust the input to the second light source 254. Thus the intensity of the light emitted by the source 254 is proportional to the intensity of light emitted by the source 236.

As FIG. 30 shows, the system 234 delivers electrical power to its rotating components through wires 251. The same wires 251 deliver power to the electric motor 253 that rotates the spool and bowl assemblies 80 and 82.

Figure 32:
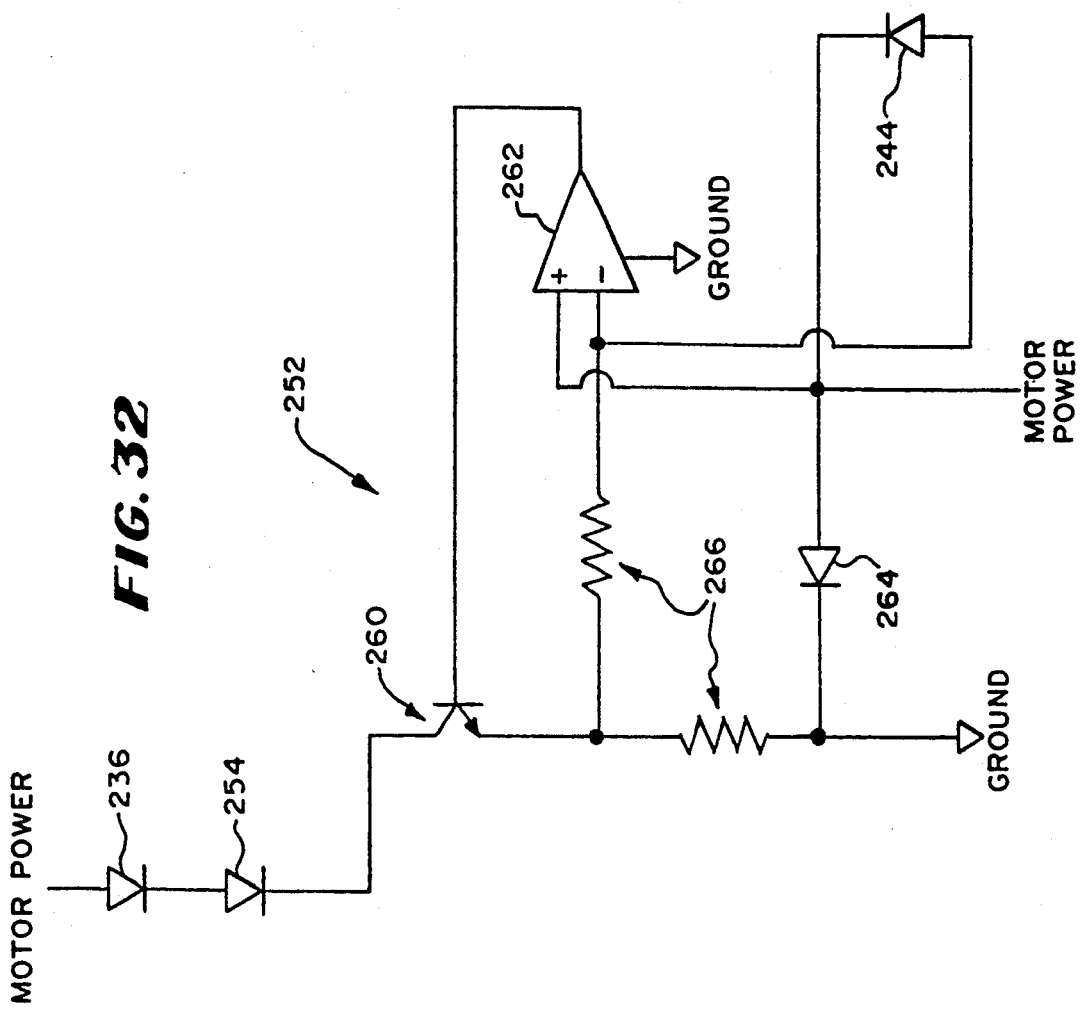
FIG. 32 is a schematic view of the light intensity control circuit associated with the interface control system shown in FIG. 30.

FIG. 32 shows a representative embodiment for the intensity control circuit 252. As shown, the control circuit 252 includes a transistor 260 that controls current flow to the series-connected first and second light sources 236 and 254.

The emitter of the transistor 260 is coupled to an amplifier 262. One amplifier input is coupled to the light detector 244 carried within the yoke viewing head 238. Another amplifier input is coupled to a reference diode 264. The circuit 252 also includes conventional current limiting resistors 266 to protect the light emitting diodes of the sources 236 and 254.

As the intensity of light hitting the detector 244 decreases, the output of the amplifier 262 increases. The transistor 260 conducts more current. The intensities of the first and second light sources 236 instantaneously increase by equal or otherwise proportional amounts.

Likewise, as the intensity of light hitting the detector 244 increases, the output of the amplifier 262 decreases. The transistor 260 conducts less current. The intensities of the first and second light sources 236 instantaneously decrease by equal or proportional amounts.

As FIG. 33A shows, the interface control circuit 270 converts the sensed light intensity output of the second detector 268 to amplified voltage signals. A conventional waveshaping circuit converts the amplified voltage signals to square wave time pulses.

From the time pulses, the interface control circuit 270 derives the physical dimension of the interface (measured in inches). The interface control circuit 270 then generates a pump control signal based upon any differences between the derived interface dimension and a desired interface dimension.

As FIG. 33A shows, the first detector 244 will view fully reflected light, free of diminution at a fixed intensity $I_1$, during the period the reflective bowl material 243 and the viewing head 238 are in alignment. The second detector 268 will also view light at a fixed intensity $I_2$ generated by the second light source 254 during this period.

As the transparent interface region of the bowl assembly 80 comes into alignment with the viewing head 238, red blood cells displayed on the interface ramp 130 will enter the optical path of the viewing head 238.

The red blood cells absorb the light from the first light source 236. This absorption reduces the previously viewed intensity of the reflected light. With decreasing light intensity sensed, the control circuit 252 instantaneously increases the input to both first and second light sources 236 and 254 to maintain a constant light intensity at the first detector 244.

Under the control of the circuit 252, both light sources 236 and 254 will become brighter, assuming a new intensity level while the red blood cell band of the interface pass past the viewing head 238.

As FIG. 33B shows, the first detector 244 will not sense this relative increase in intensity over time, because the control circuit 252 instantaneously maintains the intensity $I_1$ viewed by the first detector 244 constant. However, the second detector 268 will sense this relative increase in intensity $I_2$ over time.

As FIG. 33B shows, the second detector 268 generates an increasing intensity output signal $I_2$. The interface control circuit 270 converts the increasing intensity signal into the leading edge 274 of the square pulse 272 shown in FIG. 38B. This event marks the beginning time ($T_1$) of the pulse 272.

Eventually, the intensity signal will stabilize, as the most dense region of the red cell band of the interface enters the optical path of the viewing head 238. The interface control circuit 270 converts the stabilized intensity signal into the plateau 275 of the square pulse 272 shown in FIG. 33B.

When the red cell band of the interface leaves the optical path of the viewing head 238, the first detector 244 will again view fully reflected light from the reflective bowl material 243. With increasing light intensity sensed, the control circuit 252 will instantaneously decrease the input to both first and second light sources 236 and 254 to maintain a constant light intensity at the first detector 244.

Again, the first detector 244 will not see this relative decrease in intensity over time, because the 1control circuit 252 instantaneously maintains the intensity $I_1$ viewed by the first detector 244 constant. However, the second detector 268 will sense this relative decrease in intensity over time. The second detector 268 generates a decreasing intensity output signal $I_2$. The interface control circuit 270 converts this signal to the trailing edge 276 of the square pulse 272 shown in FIG. 38B. This event marks the ending time ($T_2$) of the pulse 272.

As FIGS. 33A and B show, the interface control circuit 270 measures, for each successive pulse 272A and 272B, the time period between the leading pulse edge 274 ($T_1$ in FIG. 33) and the trailing pulse edge 276 $T_2$ in FIG. 33). This measurement ($T_2$ minus $T_1$) constitutes the length of the pulse (in seconds).

The interface control circuit 270 also preferably measures the time period between two successive pulses (shown as 272A and 272B in FIG. 33C). This period of time is measured between the leading edge 274 of the first pulse 272A ($T_1$ in FIG. 33C) and the leading edge 274 of the next successive pulse 272B ($T_3$ in FIG. 33C). This measurement constitutes the period of the adjacent pulses (in seconds).

Figure 34A:
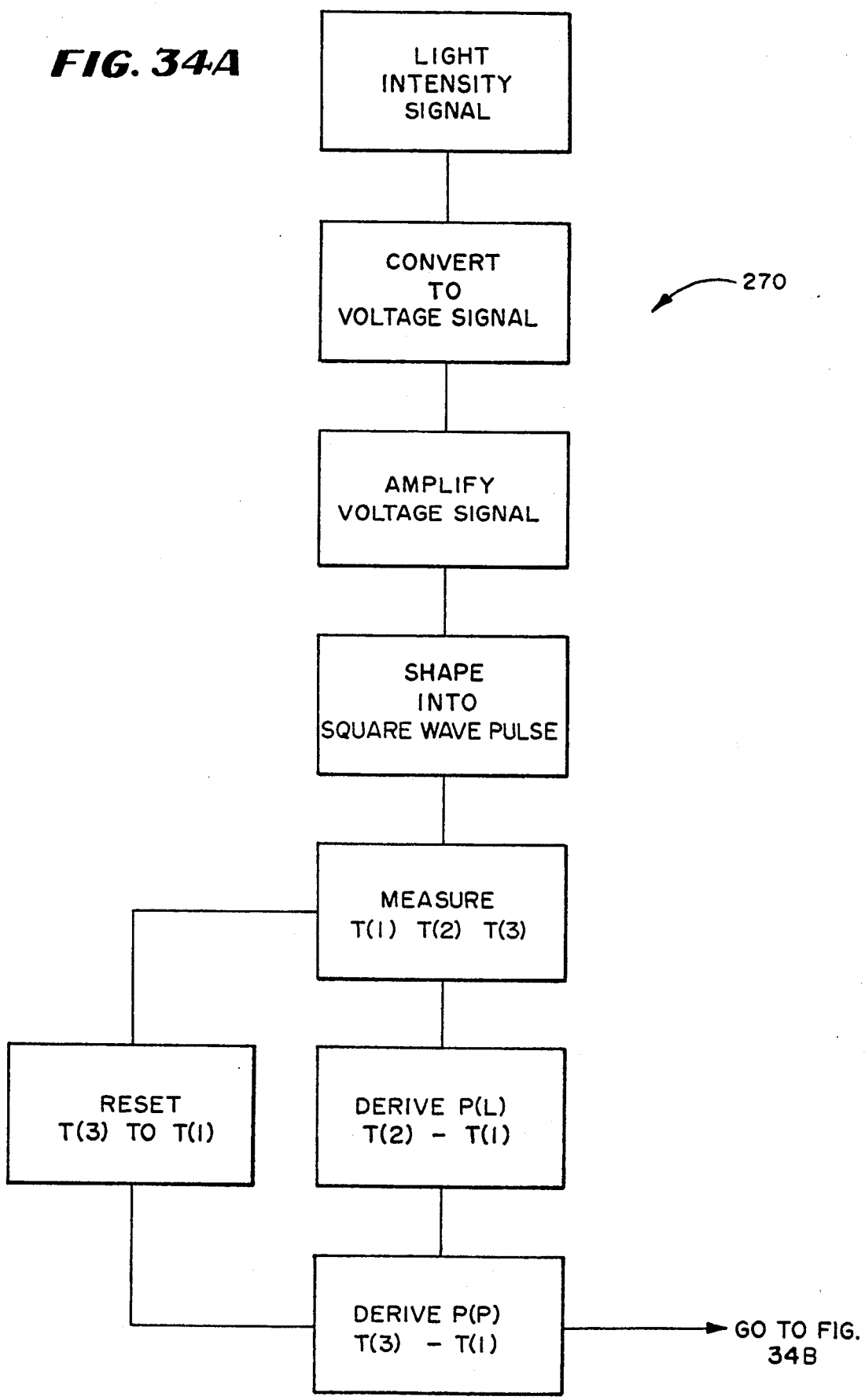
FIGS. 34A/B are flow charts showing the operation of the interface control circuit associated with the interface control system shown in FIG. 30.

After this measurement has been made, the interface control circuit 270 then resets $T_3$ to $T_1$ for the next pulse measurement cycle (see FIG. 34A).

Figure 34B:
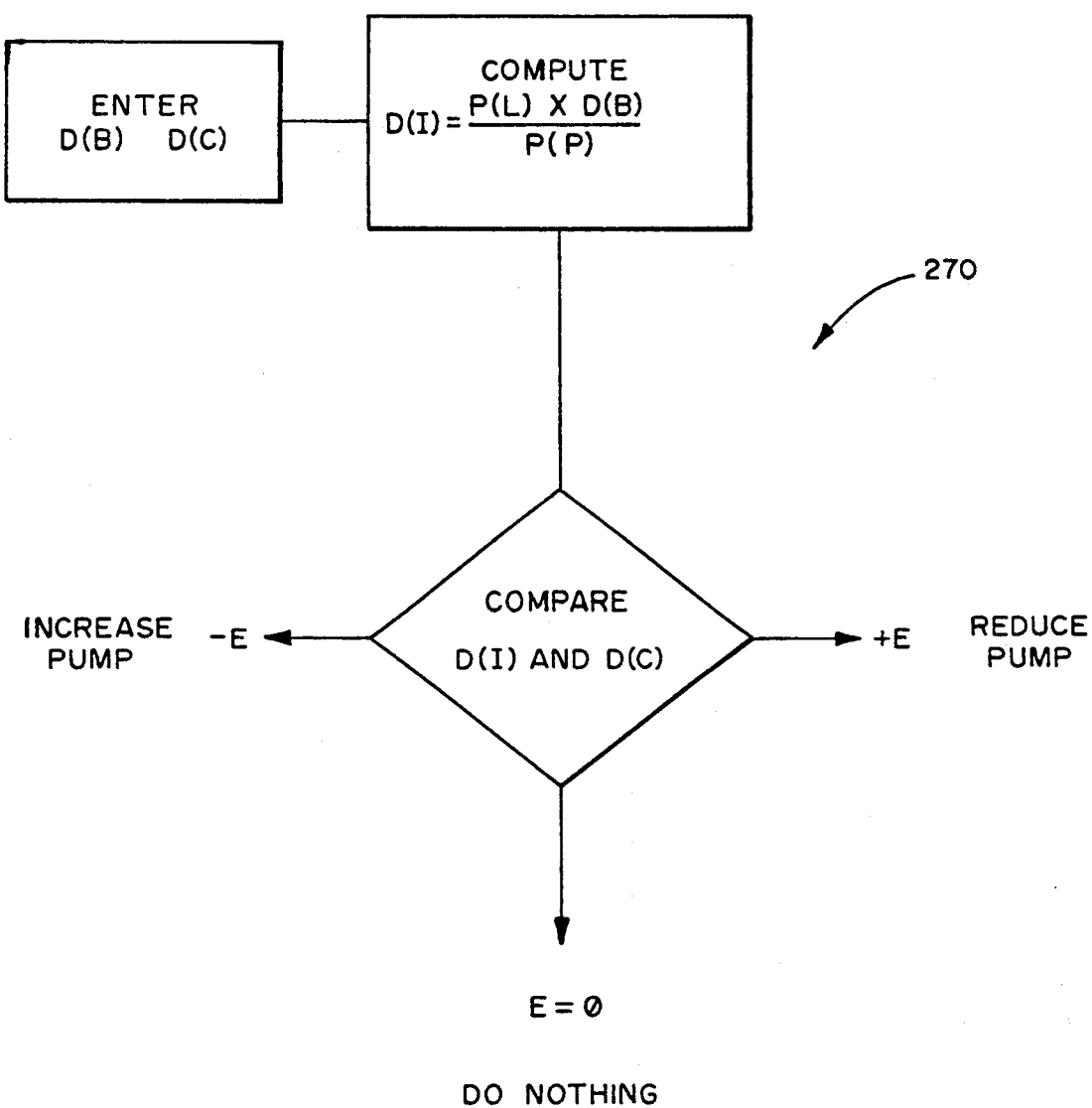

As FIG. 34B shows, the interface control circuit 270 derives the physical dimensions of the red cell band of the interface from these time pulse measurements, based upon the following relationship:

$$\frac{P_L}{P_P} = \frac{D_I}{D_B}$$

where:
$P_L$ is the measured length of the pulse ($T_2$ minus $T_1$) (in seconds);
$P_p$ is the measured period of the pulse ($T_3$ minus $T_1$) (also in seconds);
$D_I$ is the length of the red cell band of the interface (in inches) to be derived; and
$D_B$ is the circumference of the bowl assembly 80 (in inches).

If the rate of rotation of the bowl assembly 80 remains constant during the period of pulse measurements, the reciprocal of the frequency of rotation in seconds ($1/F_{rot}$, in Hz)) can be substituted for $P_p$.

Based upon the above relationship, $D_I$ can be derived as follows:

$$D_I = \frac{P_L \times D_B}{P_P}$$

As FIG. 34B shows, the interface control circuit 270 compares the derived physical measurement of the interface $D_I$ with a control value ($D_c$) to generate an error signal (E).

The interface control value $D_c$ can comprise a preselected fixed absolute value (in inches) that the user inputs. Alternatively, the interface control value $D_c$ can be expressed as a percentage based upon the length of the interface ramp 130 (i.e., red cells should occupy no more than 30% of the interface ramp 130).

With reference now also to FIG. 25A, if the error signal (E) is positive, indicating that the red cell band of the interface is too large, the interface control circuit 270 generates a signal to reduce the pumping rate of the plasma pumping station 186/210 (see FIG. 34B). This pushes the RBC region away from the PRP collection port 72 back toward the desired control position (FIG. 25B), where the error signal (E) is zero.

With reference to FIG. 25C, if the error signal (E) is negative, indicating that the red cell band of the interface is too small, the interface control circuit 270 generates a signal to increase the pumping rate of the plasma pumping station 186/210 (see FIG. 34B). This pushes the RBC region toward the PRP collection port 72 back toward the desired control position (FIG. 25B), where the error signal (E) is again zero.

The optical data link 278 described above is representative of a broader class of systems for transmitting a control signal between a rotating element and a stationary element without mechanical contact between the two elements.

Like the illustrated optical data link 278, such a system employs sensor means on either the rotating or stationary element. The sensor means senses an operating condition that is subject to change. The sensor means generates a first output signal that varies according to changes in the sensed operating condition.

Like the illustrated optical data link 278, such a system includes an energy emitter on the one element that carries the sensor means. The emitter emits energy to the other element without mechanical contact with the other element. The emitter modulates the emitted energy according to variations occurring in the intensity of the first output signal. Alternatively, the sensor means itself can constitute an emitter of modulated energy.

The emitted energy used by the data link 278 is light. However, sound energy or other types of electromagnetic energy could be used as well.

Like the illustrated data link 278, the system includes a detector on the other element for receiving the modulated energy emitted by the emitter. The detector demodulates the detected energy to generate a second output signal that, like the first output signal, varies according to the changes in the sensed operating condition.

Such a "connectionless" system for transmitting data between moving and stationary elements would be applicable for use for all sorts of real time control functions, not just interface control.

Various features of the inventions are set forth in the following claims.

We claim:

1. A system for monitoring the interface region between cellular constituents and plasma in a blood separation chamber comprising
sensor means for emitting upon the interface region energy that is absorbed by the cellular constituent portion of the interface and detecting the intensity of the energy that is not absorbed by the interface region to generate an unabsorbed intensity output signal,
means for moving the interface region relative to the sensor means during a prescribed time period, and
first means for measuring variations in the unabsorbed intensity output signal over the prescribed time period and generating a time based output.

2. A system according to claim 1 and further including second means for deriving the physical size of the interface region based upon the time based output.

3. A system according to claim 1 wherein the sensor means includes
   a first emitter for emitting upon the interface region energy that is absorbed by the cellular constituent portion of the interface, and
   a first detector for detecting the intensity of the energy emitted by the first emitter that is not absorbed by the interface region and for generating the unabsorbed intensity output signal.

4. A system according to claim 3 wherein the first means includes
   means coupled to the first detector for generating a correction signal to alter the intensity of the energy emitted by the first emitter to keep the unabsorbed intensity output signal constant, and
   means for registering the first emitter intensities as altered in response to the correction signal over the prescribed time period and generating the time based output of these altered intensities.

5. A system according to claim 4 wherein means for registering the first emitter intensities converts the intensities to voltage signals and includes circuit means for converting the voltage signals to square wave time pulses.

6. A system according to claim 5 and further including second means for deriving the physical size of the cellular constituent portion of the of the interface region ($D_I$) as follows:

$$D_I = \frac{P_L \times D_B}{P_P},$$

where:
   $P_L$ is the measured length of the time pulse (in seconds);
   $P_p$ is the measured period of the time pulse (also in seconds);
   $D_I$ is the length of the cellular constituent portion of the interface (in inches) to be derived; and
   $D_B$ is the circumference of the blood separation chamber (in inches).

7. A system according to claim 6 and further including third means for comparing the derived physical measurement of the interface $D_I$ with a control value to generate an error signal.

8. A system according to claim 7 wherein the third means applies the error signal to alter the position of the cellular constituent portion of the interface region.

9. A system according to claim 3 wherein the first means includes
   a second emitter coupled to the first emitter for emitting energy at a proportional intensity as the first emitter,
   a second detector for detecting energy emitted by the second emitter and generating a sensed intensity output signal,
   first circuit means coupled to the first detector for altering the intensity of the energy emitted by the first and second emitters to keep the unabsorbed intensity output signal of the first detector constant, and
   second circuit means coupled to the second detector for measuring variations in the sensed intensity output signal of the second detector over time and generating the time based output.

10. A system according to claim 9 wherein second circuit means converts the sensed intensity output signals to voltage signals and converts the voltage signals to square wave time pulses.

11. A system according to claim 10 and further including second means for deriving the physical dimension of the cellular constituent portion of the interface region ($D_I$) as follows:

$$D_I = \frac{P_L \times D_B}{P_P}$$

where:
   $P_L$ is the measured length of the time pulse (in seconds);
   $P_p$ is the measured period of the time pulse (also in seconds);
   $D_I$ is the length of the cellular constituent portion of the interface (in inches) to be derived; and
   $D_B$ is the circumference of the blood separation chamber (in inches).

12. A system according to claim 11 and further including third means for comparing the derived physical measurement of the interface $D_I$ with a control value to generate an error signal.

13. A system according to claim 12 wherein the third means applies the error signal to alter the location of the cellular constituent portion of the interface region.

14. A centrifuge for separating blood components comprising
   a first rotating element,
   a second rotating element supported on the first rotating element, the second rotating element including means defining a processing chamber,
   drive means for rotating the first element at a first preselected fixed rate while keeping the second rotating element rotating in a preselected rotational relationship with the first rotating element,
   means for introducing blood into the processing chamber while rotating for separation into a first region of cellular components, a second region of plasma, and an interface region between the first and second regions, the interface region having a cellular constituent band adjoining the first region and a plasma band adjoining the second region, and.,
   means for monitoring the interface region within the rotating processing element comprising
      sensor means carried on the first rotating element for emitting upon the interface region energy that is absorbed by first region of cellular components and detecting the intensity of the energy that is not absorbed by the interface region to generate an unabsorbed intensity output signal, and
      first means for measuring variations in the unabsorbed intensity output signal over time and generating a time based output.

15. A centrifuge according to claim 14 and further including second means for deriving the physical size of the interface region based upon the time based output.

16. A centrifuge according to claim 14 wherein the sensor means includes a first emitter for emitting upon the interface region energy that is absorbed by the cellular constituent portion of the interface, and a first detector for detecting the intensity of the energy emitted by the first emitter that is not absorbed by the interface region and for generating the unabsorbed intensity output signal.

17. A centrifuge according to claim 16 wherein the first means includes means coupled to the first detector for generating a correction signal to alter the intensity of the energy emitted by the first emitter to keep the unabsorbed intensity output signal constant, and means for registering the first emitter intensities as altered in response to the correction signal over time and generating the time based output of these altered intensities.

18. A centrifuge according to claim 17 wherein means for registering the first emitter intensities converts the intensities to voltage signals and includes circuit means for converting the voltage signals to square wave time pulses.

19. A centrifuge according to claim 18 and further including the second means for deriving the physical dimension of the cellular constituent band of the interface region ($D_I$) as follows:

$$D_I = \frac{P_L \times D_B}{P_P}$$

where:

$P_L$ is the measured length of the time pulse (in seconds);

$P_p$ is the measured period of the time pulse (also in seconds);

$D_I$ is the length of the cellular constituent band of the interface (in inches) to be derived; and $D_B$ is the measured circumference of the blood separation chamber (in inches).

20. A centrifuge according to claim 19 and further including third means for comparing the derived physical measurement of the interface $D_I$ with a control value to generate an error signal.

21. A centrifuge according to claim 20 wherein the third means applies the error signal to alter the position of the cellular constituent band on the interface region.

22. A centrifuge according to claim 17 wherein the first means includes a second emitter coupled to the first emitter for emitting energy at a proportional intensity as the first emitter, a second detector for detecting energy emitted by the second emitter and generating a sensed intensity output signal, first circuit means coupled to the first detector for altering the intensity of the energy emitted by the first and second emitters to keep the unabsorbed intensity output signal of the first detector constant, and second circuit means coupled to the second detector for measuring variations in the sensed intensity output signal of the second detector over time and generating the time based output.

23. A centrifuge according to claim 22 wherein second circuit means converts the sensed intensity output signals to voltage signals and converts the voltage signals to square wave time pulses.

24. A centrifuge according to claim 23 and further including second means for deriving the physical dimension of the cellular constituent band of the interface region ($D_I$) as follows:

$$D_I = \frac{P_L \times D_B}{P_P}$$

where:

$P_L$ is the measured length of the time pulse (in seconds);

$P_p$ is the measured period of the time pulse (also in seconds);

$D_I$ is the length of the cellular constituent band of the interface (in inches) to be derived; and $D_B$ is the measured circumference of the blood separation chamber (in inches).

25. A centrifuge according to claim 24 and further including third means for comparing the derived physical measurement of the interface $D_I$ with a control value to generate an error signal.

26. A centrifuge according to claim 25 wherein the third means applies the error signal to alter the location of the cellular constituent band on the interface region.

27. A centrifuge according to claim 14 wherein the processing chamber includes a low-G side wall and a high-G side wall defining a processing zone between them, at least one of the side walls including an area where the interface region is located that includes a material that is transparent to the energy emitted by the sensor means, and interior wall means extending into the processing zone for displaying the interface region for viewing through the one side wall of the processing chamber.

28. A centrifuge according to claim 14 and further including a stationary frame for supporting the first and second elements during rotation, wherein at least one component of one of the first and second means of the interface monitoring means is carried on the stationary frame, and wherein the interface monitoring means includes first data link means on the first rotating element coupled to the sensor means for emitting energy to the one component on the stationary frame without mechanical contact with the stationary frame, including means for modulating the emitted energy according to variations in the unabsorbed intensity output signal, and second data link means on the stationary frame for receiving the modulated energy emitted by the first data link means including means for demodulating the detected energy to generate a second output signal that also varies according to the variations in the unabsorbed intensity output signal.

29. A centrifuge according to claim 28 wherein the emitted energy is electromagnetic energy.

30. A centrifuge according to claim 29 wherein the electromagnetic energy is light energy.

* * * * *